United States Patent [19]

Kamiya et al.

[11] Patent Number: 4,472,300
[45] Date of Patent: Sep. 18, 1984

[54] AZETIDINONE DERIVATIVES AND PROCESS FOR PREPARATION THEREOF

[75] Inventors: Takashi Kamiya, Suita; Yoshihisa Saito, Takarazuka; Masashi Hashimoto, Toyonaka; Osamu Nakaguti, Osaka; Teruo Oku, Osaka; Youichi Shiokawa, Takatsuki; Takao Takaya, Sakai; Tadaaki Komori, Takatsuki; Tsutomu Teraji, Toyonaka; Keiji Hemmi, Kyoto; Hisashi Takasugi, Osaka, all of Japan

[73] Assignee: Fujisawa Pharmaceutical Co., Ltd., Osaka, Japan

[21] Appl. No.: 130,205

[22] Filed: Mar. 13, 1980

Related U.S. Application Data

[60] Division of Ser. No. 858,375, Dec. 7, 1977, Pat. No. 4,207,234, which is a continuation-in-part of Ser. No. 694,891, Jun. 10, 1976, abandoned, which is a continuation-in-part of Ser. No. 593,668, Jul. 7, 1975, abandoned.

[51] Int. Cl.³ .................. C07D 205/08; C07D 403/12; C07D 409/12; C07D 401/12
[52] U.S. Cl. ............................................... 260/239 A
[58] Field of Search .................... 542/455; 260/239 A

[56] References Cited

U.S. PATENT DOCUMENTS 3,487,072 12/1969 Sheehan .................. 260/239 A
4,178,286 12/1979 Wasserman .............. 260/239 AL
4,195,021 3/1980 Herron .................... 260/239 A

OTHER PUBLICATIONS

Moll et al., Achiv DerPharmazie 303, pp. 831–834 (1970).
"Molecular Modification of Drug Design" (American Chemical Society) p. 23, 1964.
Van Heyningen Journal of Medical Chemistry II, pp. 933–936/1968.
Clark et al., Ed. "The Chemistry of Penicillin", p. 977 (1979).
Duranti et al., I Chem. Abs. 81, 25597k.
Duranti et al., II Chem. Abs. 82, 72678t.
Kamiya et al. 86, 189691r.

*Primary Examiner*—Mark L. Berch
*Attorney, Agent, or Firm*—Dayton R. Stemple

[57] ABSTRACT

New antimicrobial azetidinone derivatives and their salt of the formula:

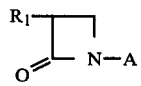

wherein $R_1$ amino or acylamino, and A is selected from a variety of groups.

1 Claim, No Drawings

AZETIDINONE DERIVATIVES AND PROCESS FOR PREPARATION THEREOF

CROSS-REFERENCE TO RELATED APPLICATION

This invention is a division of application Ser. No. 858,375, filed Dec. 7, 1977, now U.S. Pat. No. 4,207,234, which is a continuation-in-part application of copending application Ser. No. 694,891, abandoned filed on June 10, 1976, which is a continuation-in-part application of copending application Ser. No. 593,668, filed on July 7, 1975, abandoned.

BACKGROUND OF THE INVENTION

This invention is based on the success of identification of the chemical structure of FR-1923 substance. That is, FR-1923 substance is a known antibiotic isolated from the fermentation broth of a strain of the genus Nocardia deposited with the American Type Culture Collection under ATCC No. 21806, the details of which are described for example, in German Patent application No. 2,242,699, which corresponds to U.S. Pat. No. 3,923,977 issued on Dec. 2, 1975.

In said prior literature, the FR-1923 substance is defined by the various physico-chemical properties without any disclosure of its chemical structure. As a result of extensive structural determination study, the inventors of this invention have established the structure of the FR-1923 substance as 1-(α-Carboxy-4-hydroxybenzyl)-3-(((2-((4-(3-amino-3-carboxypropoxy)phenyl))-2-hydroxyiminoacetamido)))-2-azetidinone of the following formula.

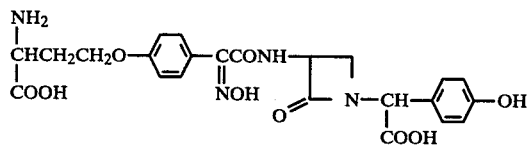

(FR-1923 substance)

The above attractive and unique single β-lactam structure of the antibiotic FR-1923 substance makes the inventors of this invention encouraged to study on chemical syntheses of FR-1923 substance per se and other related new single β-lactam compounds in favour of searching the structure-activity relationship and other active derivatives, analogues or homologues and further any possibility of an industrial synthetic process for the preparation thereof.

From the above viewpoint, the inventors of this invention have synthesized a lot of novel and unique modified compounds of FR-1923 substance and together with have made intensive efforts to prepare some usefull intermediary 3-amino-2-azetidinone compounds, so far as profitable.

For the purpose of illustrating the state of prior arts, the all of limited known related compounds which were synthesized from penicillins by degradative reactions and the relevant literatures are mentioned as follows:

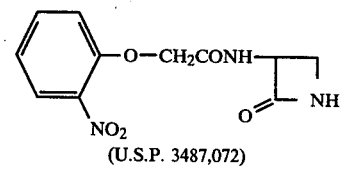

(U.S.P. 3487,072)

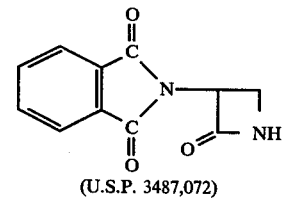

(U.S.P. 3487,072)

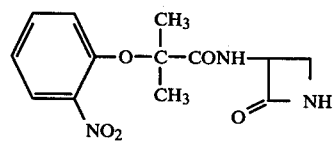

(Journal of Organic Chemistry, Vol. 38, p. 940-943, 1973)

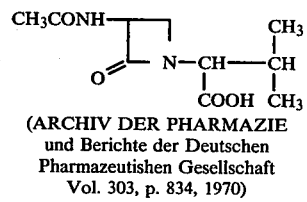

(ARCHIV DER PHARMAZIE und Berichte der Deutschen Pharmazeutishen Gesellschaft Vol. 303, p. 834, 1970)

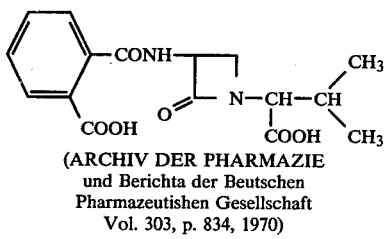

(ARCHIV DER PHARMAZIE und Berichta der Deutschen Pharmazeutishen Gesellschaft Vol. 303, p. 834, 1970)

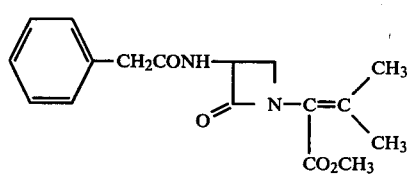

(MOLECULAR MODIFICATION IN DRUG DESIGN, Page 23, 1964, published by American Chemical Society)

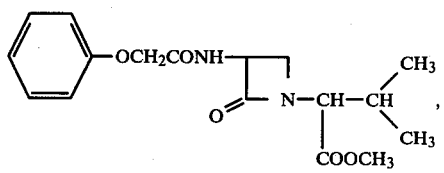

(Journal of Medical Chemistry, Vol. 11 (4), P. 933-936, 1968)

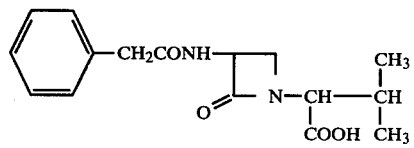

-continued
(The Chemistry of Penicillin,)
P 977

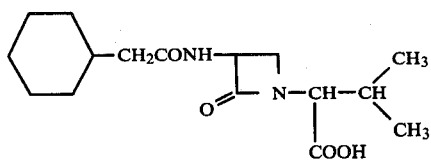

(The Chemistry of Penicillin,)
P 977

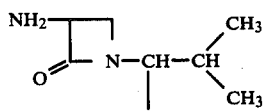

(ARCHIV DER PHARMAZIE un Berichte
der Deutschen Pharmazeutischen
Gesellschaft
Vol. 303, P 832, 1970)

DETAILED DESCRIPTION OF THE PREFERRED EMBODIMENTS OF THE INVENTION

This invention relates to azetidinone derivatives. More particularly, it relates to novel azetidinone derivatives having antimicrobial activities and to process for preparation thereof.

Accordingly, it is an object of this invention to provide azetidinone derivatives having antimicrobial activities.

Another object of this invention is to provide a process for preparation of the azetidinone derivatives.

The azetidinone derivatives of this invention are new compounds in the art and represented by the following general formula (I)

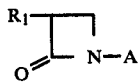

wherein
$R_1$ is amino or acylamino, and
A is hydrogen or a group represented by the formula:

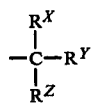

wherein
$R^X$ is hydrogen;
$R^Y$ is hydrogen, alkyl containing up to 6 carbon atoms which may be substituted by one or more groups selected from hydroxy and amino, or phenyl which may be substituted by one or more groups selected from hydroxy, amino, nitro, alkyl containing up to 6 carbon atoms, alkoxy containing up to 6 carbon atoms, aralkoxy in which alkane moiety contains up to 6 carbon atoms, alkylthio containing up to 6 carbon atoms and halogen; or
$R^X$ and $R^Y$ are linked together to form alkylidene containing up to 6 carbon atoms; and
$R^Z$ is carboxy or pharmaceutically acceptable salt thereof, hydroxy, amino, cyano or alkyl containing up to 6 carbon atoms which is substituted by carboxy or pharmaceutically acceptable salt thereof;
provided that when $R_1$ is 2[4-(3-amino-3-carboxypropoxy)phenyl]-2-hydroxyiminoacetamido, A is hydrogen or a group represented by the formula:

wherein
$R^X$ is hydrogen:
$R^{Ya}$ is hydrogen, alkyl containing up to 6 carbon atoms, or phenyl which may be substituted by one or more groups selected from amino, nitro, alkyl containing up to 6 carbon atoms, alkoxy containing up to 6 carbon atoms, aralkoxy in which alkane moiety contains up to 6 carbon atoms, alkylthio containing up to 6 carbon atoms and halogen; or
$R^X$ and $R^{Ya}$ are linked together to form alkylidene containing up to 6 carbon atoms; and
$R^Z$ is carboxy or pharmaceutically acceptable salt thereof, hydroxy, amino, cyano or alkyl containing up to 6 carbon atoms which is substituted by carboxy or pharmaceutically acceptable salt thereof:
when $R_1$ is acetamido, benzamido or phenylacetamido, A is hydrogen or a group represented by the formula:

wherein
$R^X$ is hydrogen;
$R^{Yb}$ is hydrogen or phenyl which may be substituted by one or more groups selected from hydroxy, amino, nitro, alkyl containing up to 6 carbon atoms, alkoxy containing up to 6 carbon atoms, aralkoxy in which alkane moiety contains up to 6 carbon atoms, or alkylthio containing up to 6 carbon atoms and halogen; and
$R^Z$ is carboxy or pharmaceutically acceptable salt thereof, hydroxy, amino, cyano or alkyl containing up to 6 carbon atoms which is substituted by carboxy or pharmaceutically acceptable salt thereof:
When $R_1$ is 2-(2-nitrophenoxy)acetamido or 2-(2-nitrophenoxy)-2-methylpropionamido or phthalimido, A is a group represented by the formula:

wherein
$R^X$ is hydrogen;
$R^Y$ is hydrogen, alkyl containing up to 6 carbon atoms which may be substituted by one or more groups selected from hydroxy and amino, or phenyl which may be substituted by one or more groups selected from hydroxy, amino, nitro, alkyl containing up to 6 carbon atoms, alkoxy containing up to 6 carbon atoms, aralkoxy in which alkane moiety contains up to 6 carbon atoms, alkylthio containing up to 6 carbon atoms and halogen; or $R^X$ and $R^Y$ are linked together to form alkylidene containing up to 6 carbon atoms; and $R^Z$ is carboxy or pharmaceutically acceptable salt thereof, hydroxy, amino, cyano or alkyl containing up to 6 carbon atoms which is substituted by carboxy or pharmaceutically acceptable salt thereof.

With regard to the definition of the compound of the formula (I), "acyl" in acylamino for $R_1$ is intended and restricted to mean "acyl consisting of an organic carbonyl(—CO—) and organic sulfonyl(—SO$_2$—)", more particularly, in other words, "acyl derived from organic carboxylic acid (i.e. organic carboxylic acyl), organic carbamic acid (i.e. organic carbamic acyl), organic carbonic acid (i.e. organic carbonic acyl) and organic sulfonic acid (i.e. organic sulfonic acyl). Further, it is to be understood that the present object compound of the formula (I), within the scope thereof, includes its equivalences such as the conventionally blocked functional derivatives at the carboxy group (e.g. esterified carboxy), the amino group (e.g. conventionally protected amino), and the hydroxy group (e.g. conventionally protected hydroxy) of the molecule of compound (I), respectively. The detail of such equivalences of the compound (I) will be apparent in the descriptions as disclosed hereinafter.

Further, the compound of the present invention includes the compound of the following formula:

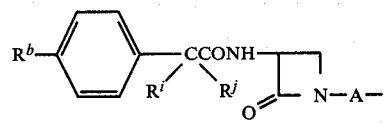

wherein $R^h$ is hydrogen or a radical of the formula:

wherein $R^f$ is hydrogen or lower alkoxycarbonyl; $R^i$ and $R^j$ are each hydrogen or combined to form OXO; and A''' is a radical of the formula:

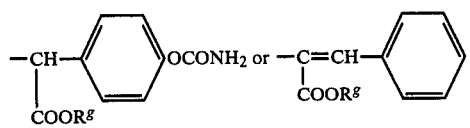

According to this invention, the azetidinone derivatives (I) can be prepared by various synthetic methods, which are illustrated collectively by the following schemes for convenience's sake.

(1) Process 1:

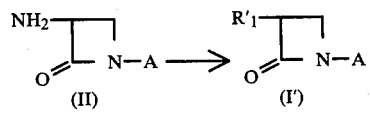

(2) Process 2:

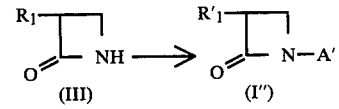

(3) Process 3:

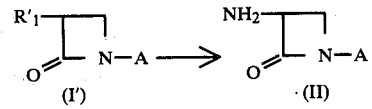

(4) Process 4:

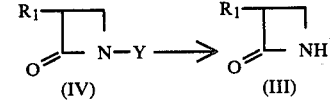

(5) Process 5:

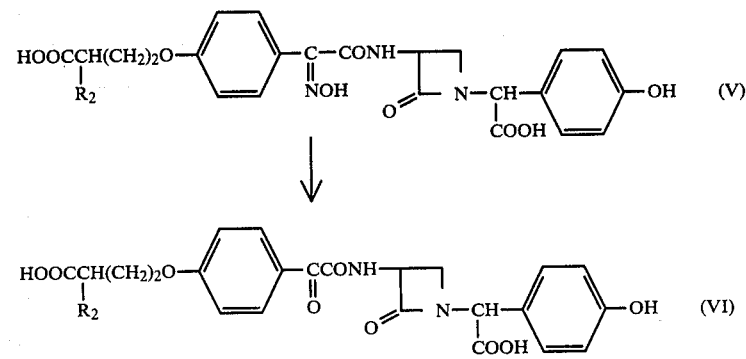

(6) Process 6:

-continued
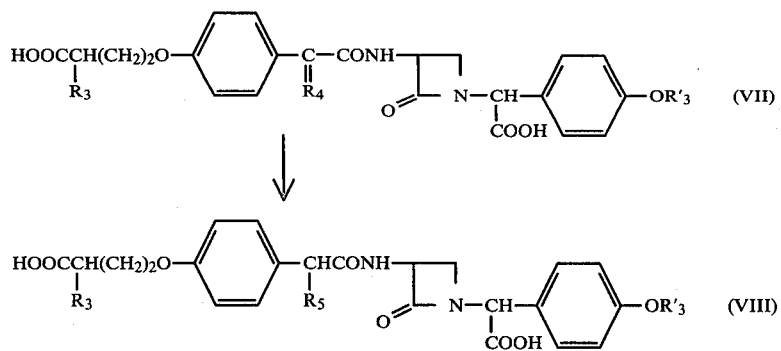
(7) Process 7:
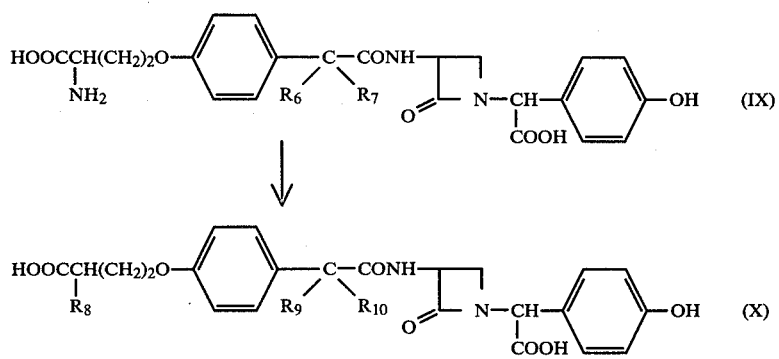
(8) Process 8:
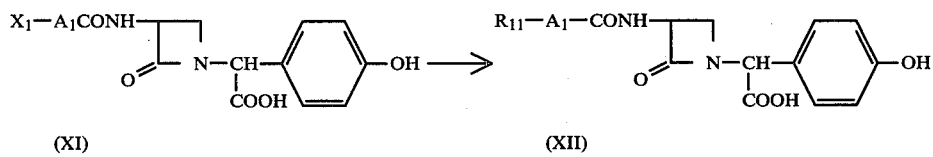
(9) Process 9:
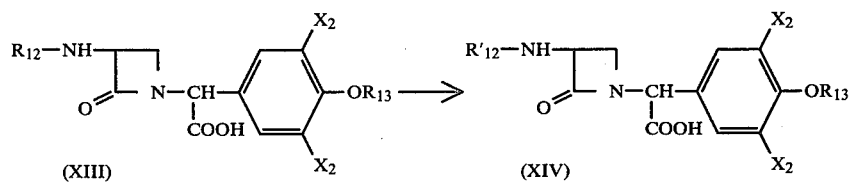
(10) Process 10:
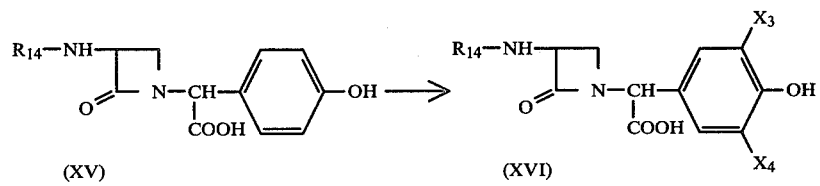
(11) Process 11:
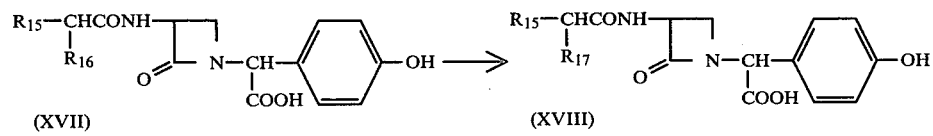
(12) Process 12:

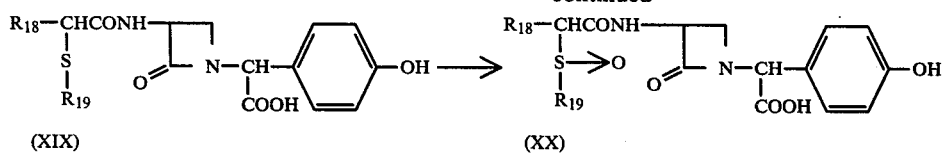
(13) Process 13:
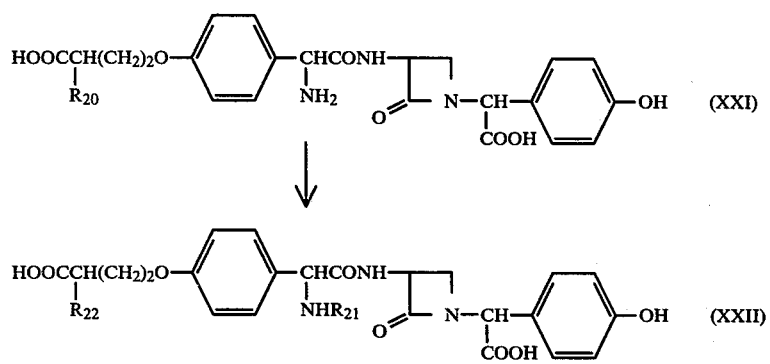
(14) Process 14:
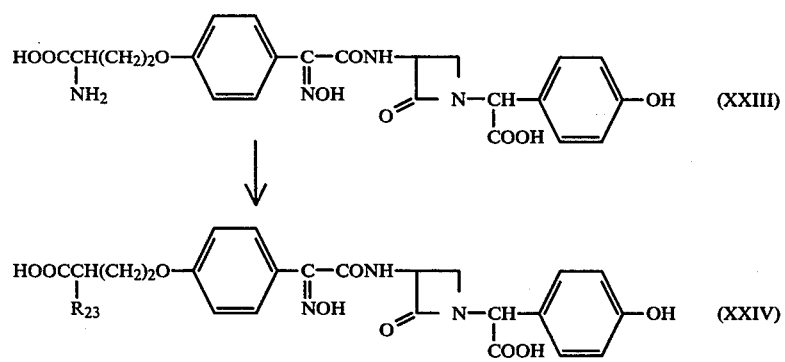
(15) Process 15:
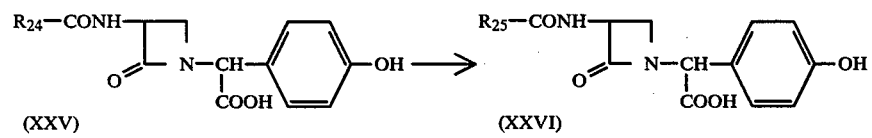
(16) Process 16:
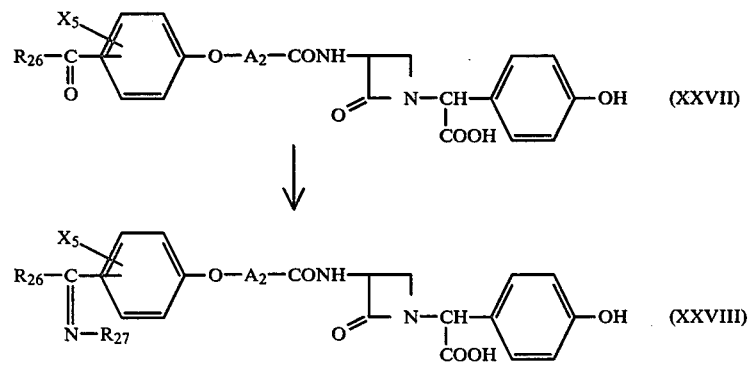
(17) Process 17:

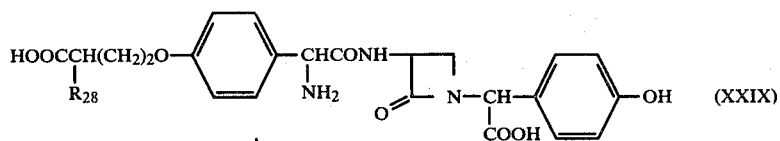 (XXIX)
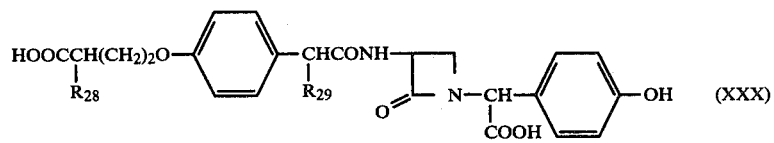 (XXX)
(18) Process 18:
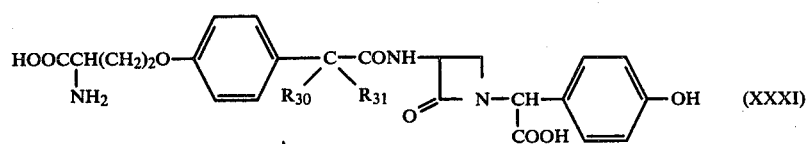 (XXXI)
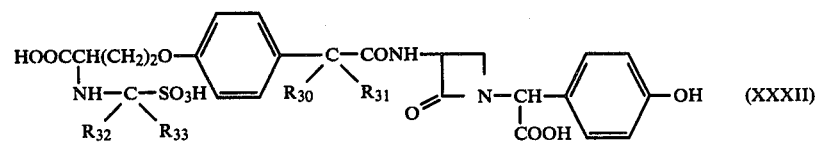 (XXXII)
(19) Process 19:
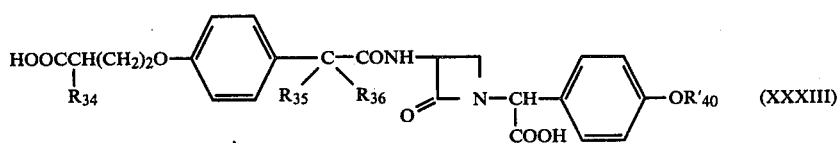 (XXXIII)
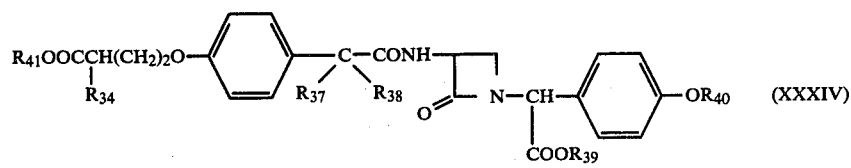 (XXXIV)
(20) Process 20:
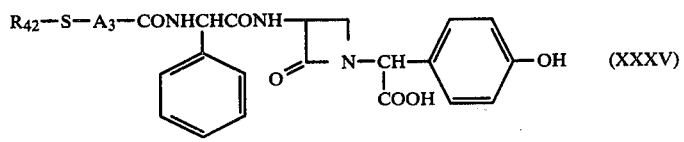 (XXXV)
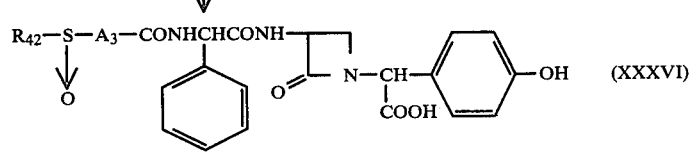 (XXXVI)
(21) Process 21:

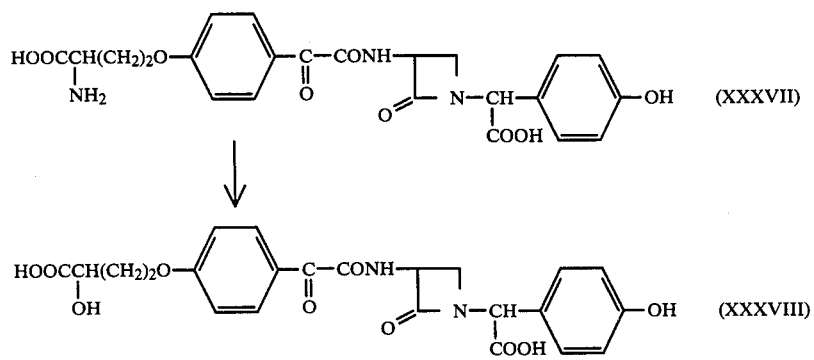 (XXXVII)
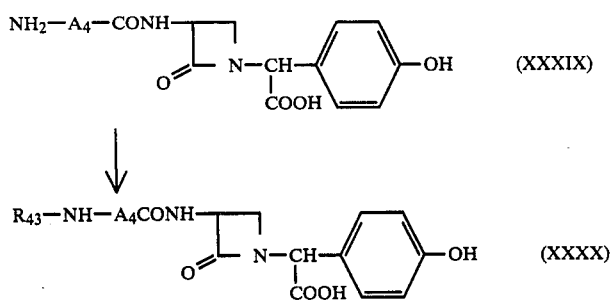 (XXXVIII)
(22) Process 22:
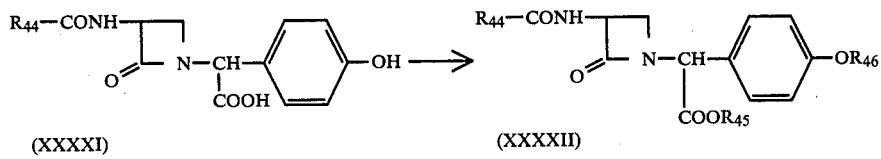
(23) Process 23:
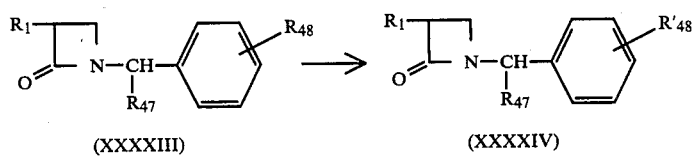
(24) Process 24:
(25) Process 25:      (26) Process 26:
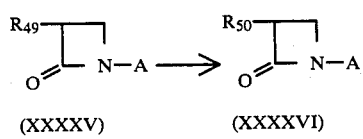    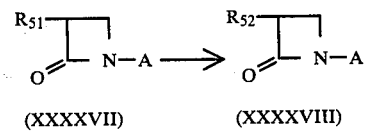
(XXXXV)   (XXXXVI)    (XXXXVII)   (XXXXVIII)
(27) Process 27:      (28) Process 28:
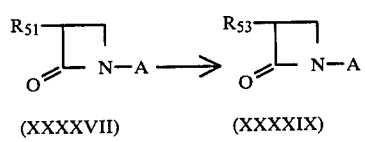    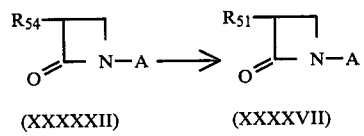
(XXXXVII)   (XXXXIX)    (XXXXXII)   (XXXXVII)
(29) Process 29:
(a) 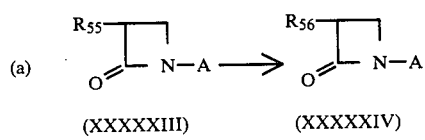
(XXXXXIII)    (XXXXXIV)

(b) 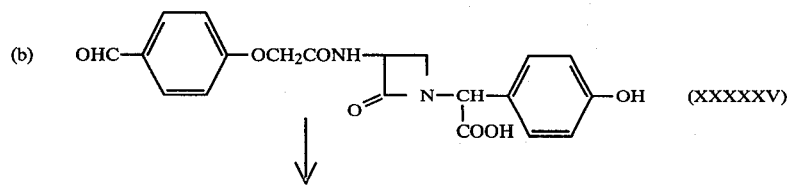 (XXXXXV)
↓
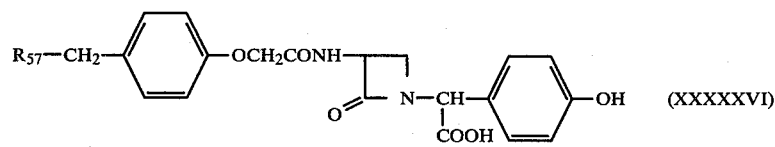 (XXXXXVI)
(30) Process 30:
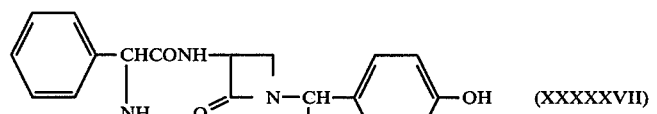 (XXXXXVII)
↓
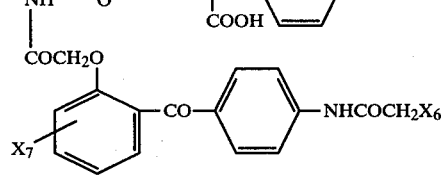 (XXXXXVIII)
(31) Process 31:
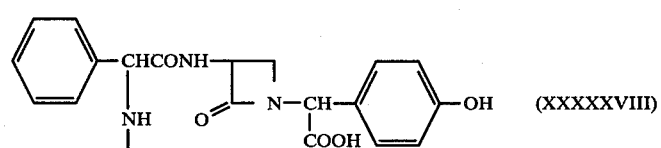
(XXXXX)  (XXXXXI)
(32) Process 32:
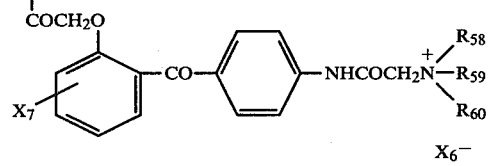
(33) Process 33:

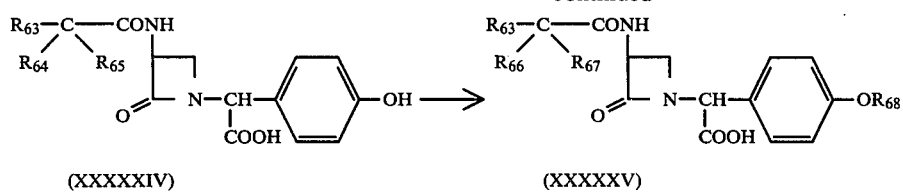
(XXXXXIV) → (XXXXXV)
(34) Process 34:
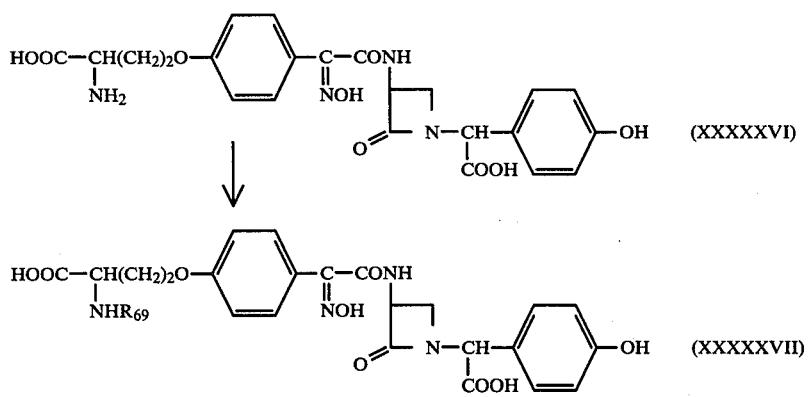
(35) Process 35:
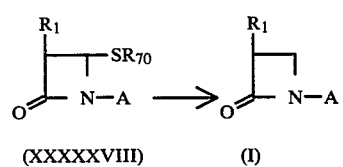
(XXXXXVIII) → (I)
(36) Process 36:
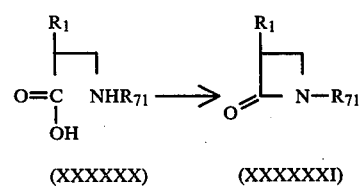
(XXXXXX) → (XXXXXXI)
(37) Process 37:
(38) Process 38:
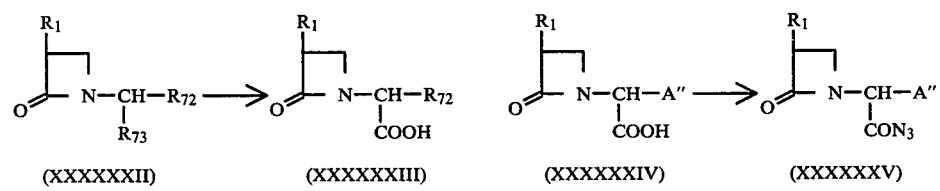
(XXXXXXII) → (XXXXXXIII)    (XXXXXXIV) → (XXXXXXV)
(39) Process 39:
(40) Process 40:
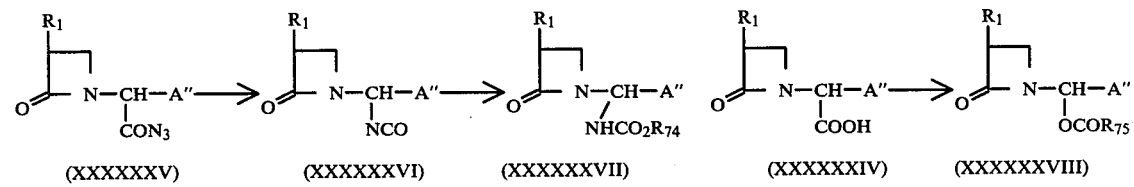
(XXXXXXV) → (XXXXXXVI) → (XXXXXXVII)    (XXXXXXIV) → (XXXXXXVIII)
(41) Process 41:
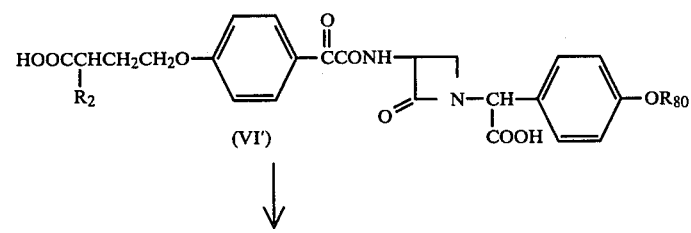
(VI')

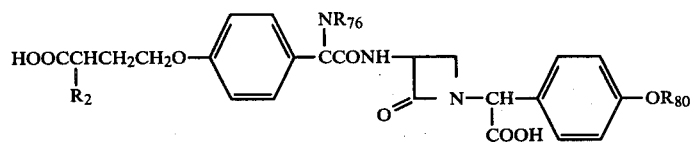
(XXXXXXIX)
(42) Process 42:
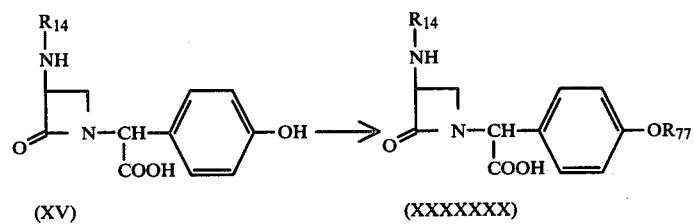
(XV)      (XXXXXXX)
(43) Process 43:
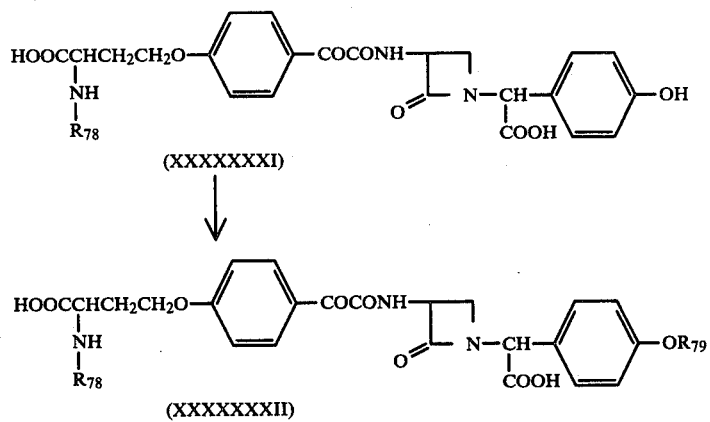
(XXXXXXXI)
↓
(XXXXXXXII)
Process 44:
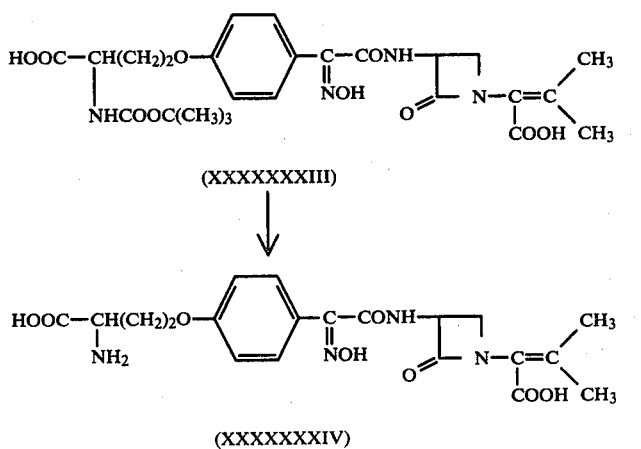
(XXXXXXXIII)
↓
(XXXXXXXIV)
Process 45:
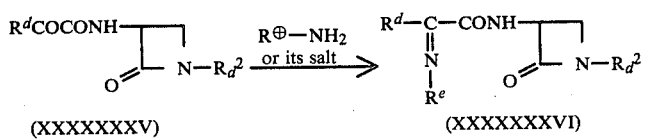
(XXXXXXXV)      (XXXXXXXVI)
Process 46:

-continued
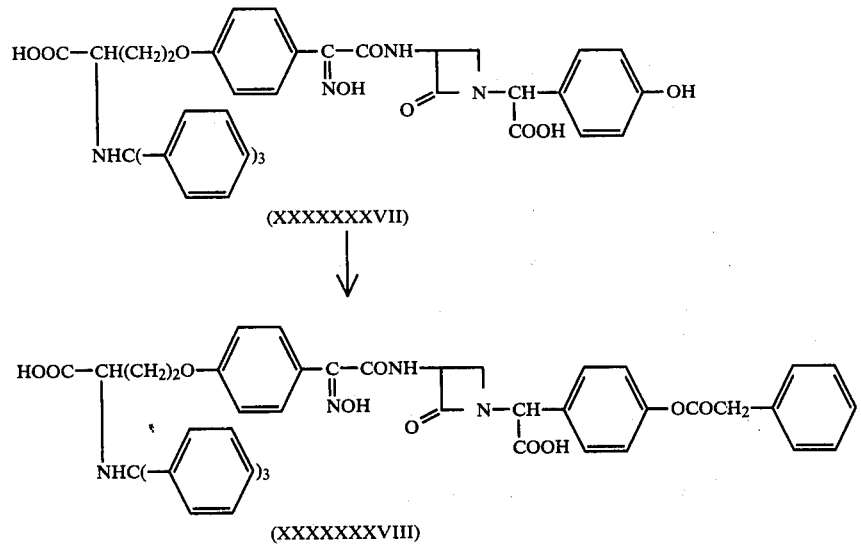
Process 47:
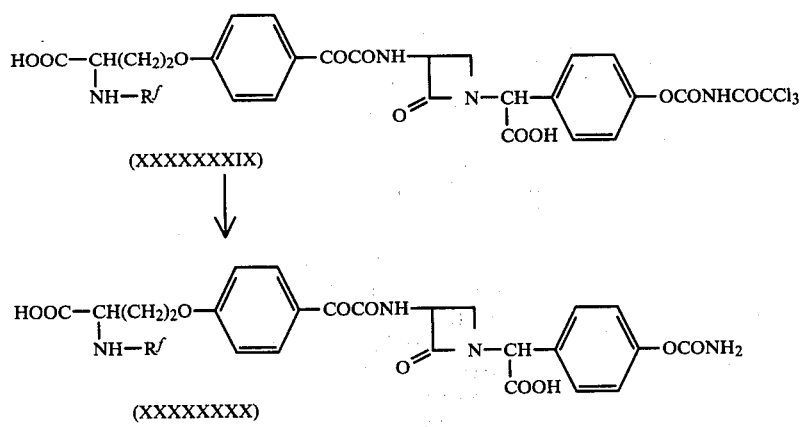
Process 48:
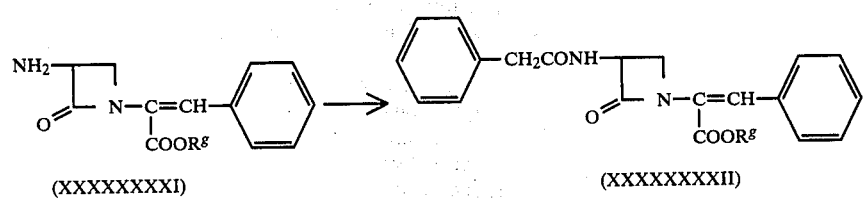
Process 49:
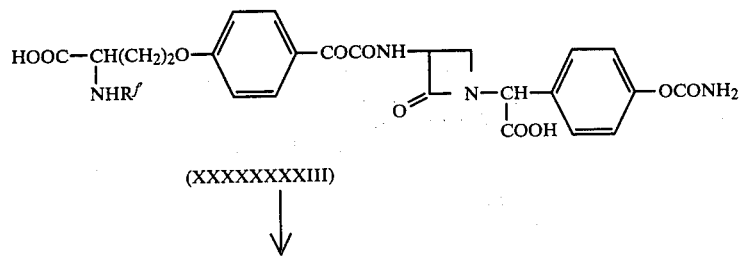

HOOC—CH(CH₂)₂O—⟨phenyl⟩—COCONH—[β-lactam]—N—CH—⟨phenyl⟩—OCONH₂
         |                                              |
         NH₂                                            COOH (XXXXXXXXIV)

With regard to the above processes, it is to be understood that the Process 1 and Process 2 are fundamental processes and the remaining Processes are alternative ones.

The definitions of the symbols used in the above formulae are mentioned in the following:

$R_1$ is as defined above;
A is as defined above;
A' is as defined in the symbol "A" excepting hydrogen;
$R'_1$ is acylamino;
Y is oxalo, esterified oxalo, 1-(protected amino)alkyl or 1-(protected hydroxy)alkyl;
$R_2$ is amino or acylamino;
$R_3$ is amino or acylamino;
$R'_3$ is hydrogen or aralkyl;
$R_4$ is oxo or hydroxyimino;
$R_5$ is amino or hydroxy;
$R_6$ and $R_7$ are combined to form oxo or hydroxyimino, or $R_6$ is hydrogen, and $R_7$ is amino or hydroxy;
$R_8$ is acylamino;
$R_9$ and $R_{10}$ are combined to form oxo or hydroxyimino, or $R_9$ is hydrogen and $R_{10}$ is amino, hydroxy, acylamino or acyloxy;
$X_1$ is acid residue;
$A_1$ is bivalent aliphatic hydrocarbon radical;
$R_{11}$ is residue of nucleophile;
$R_{12}$ is acyl having protected amino, protected hydroxy or protected carboxy function(s);
$R'_{12}$ is acyl having amino, hydroxy or carboxy function(s);
$R_{13}$ is hydrogen, aralkyl, acyl or alkyl;
$X_2$ is hydrogen or halogen;
$R_{14}$ is acyl;
$X_3$ is hydrogen or halogen;
$X_4$ is halogen;
$R_{15}$ is hydrogen, alkyl, aryl, aralkyl, aryloxy, heterocyclic group or heterocyclic alkyl;
$R_{16}$ is amino or hydrocarbon radical having amino;
$R_{17}$ is acylamino or acylamino-substituted-hydrocarbon residue;
$R_{18}$ is hydrogen or aryl;
$R_{19}$ is alkyl, N-arylcarbamoylalkyl or aryl;
$R_{20}$ is amino or acylamino;
$R_{21}$ is aryl substituted by at least one of nitro and esterified carboxy;
$R_{22}$ is acylamino or arylamino whose aryl ring is substituted by at least one of nitro and esterified carboxy;
$R_{23}$ is mono- or di-alkylamino;
$R_{24}$ is nitroaryl;
$R_{25}$ is aminoaryl;
$R_{26}$ is hydrogen, alkyl or aryl;
$X_5$ is hydrogen or halogen;
$A_2$ is bivalent aliphatic hydrocarbon radical;
$R_{27}$ is hydroxy, alkoxy or alkanoyl amino;
$R_{28}$ is acylamino;
$R_{29}$ is acylamino;
$R_{30}$ and $R_{31}$ are combined to form oxo or hydroxyimino, or $R_{30}$ is hydrogen and $R_{31}$ is hydroxy;
$R_{32}$ and $R_{33}$ are hydrogen or alkyl;
$R_{34}$ is acylamino;
$R_{35}$ and $R_{36}$ are combined to form oxo or hydroxyimino, acyloxyimino, or $R_{35}$ is hydrogen and $R_{36}$ is acylamino or hydroxy;
$R_{37}$ and $R_{38}$ are combined to form oxo, hydroxyimino, acyloxyimino, alkoxyimino or substituted alkoxyimino, or $R_{37}$ is hydrogen and $R_{38}$ is acylamino, hydroxy, alkoxy or substituted alkoxy;
$R_{39}$ is alkyl or substituted alkyl;
$R'_{40}$ is hydrogen or acyl;
$R_{40}$ is hydrogen, acyl or substituted or unsubstituted alkyl;
$R_{41}$ is alkyl or substituted alkyl;
$R_{42}$ is alkyl, aryl or aralkyl;
$A_3$ is alkylene;
$A_4$ is bivalent aliphatic hydrocarbon radical;
$R_{43}$ is aromatic heterocyclic group or aryl substituted by at least one of nitro and esterified carboxy;
$R_{44}$ is aralkyl;
$R_{45}$ is alkyl;
$R_{46}$ is hydrogen or alkyl;
$R_{47}$ is carboxy or its derivative;
$R_{48}$ is a protected amino or a protected hydroxy;
$R'_{48}$ is amino or hydroxy;
$R_{49}$ is an acylamino having carboxy or its reactive derivative;
$R_{50}$ is an acylamino having a substituent selected from carbazoyl, N-(hydroxyalkyl)-carbamoyl and N-aralkylcarbamoyl;
$R_{51}$ is an acylamino having amino;
$R_{52}$ is an acylamino having esterified carboxy substituted alkylamino;
$R_{53}$ is an acylamino having esterified carboxy substituted alkenyl amino;
$R_{54}$ is an acylamino having at least one of nitro and azido;
$R_{55}$ is an acylamino having a substituent selected from formyl, alkanoyl and aroyl;
$R_{56}$ is an acylamino having at least one of hydroxyalkyl and α-hydroxyaralkyl;
$R_{57}$ is aralkylamino;
$X_6$ is halogen;
$X_7$ is hydrogen or halogen;
$R_{58}$, $R_{59}$ and $R_{60}$ are each alkyl; and
$R_{61}$ is aralkanoylamino;
$R_{62}$ is aryl;
$A_5$ is alkylene;
$R_{63}$ is aryl or heterocyclic group;
$R_{64}$ and $R_{65}$ are each hydrogen, or both are combined to form hydroxyimino;
$R_{66}$ and $R_{67}$ are each hydrogen, or both are combined to form aroyloxyimino or aralkoxycarbonyloxyimino;
$R_{68}$ is aroyl or aralkoxycarbonyloxyimino;

$R_{69}$ is aralkyl;

$R_{70}$ is alkyl, heterocyclicthio or a radical of the formula:

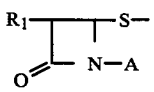

wherein A is as defined above;

$R_{71}$ is alkyl having at least one of carboxy and esterified carboxy;

$R_{72}$ is hydrogen, alkyl, or substituted or unsubstituted aryl;

$R_{73}$ is esterified carboxy;

$A''$ is alkyl, alkenyl or aryl;

$R_{74}$ is alkyl;

$R_{75}$ is lower alkyl;

$R_{76}$ is alkoxy, (carboxy or esterified carboxy)alkoxy, aralkoxy, ureido, thioureido, or amino;

$R_{77}$ is aralkyl;

$R_{78}$ is amino-protecting group;

$R_{79}$ is acyl;

$R_{80}$ is hydrogen, hydroxy, acyloxy, alkyloxy or aralkyloxy;

$R^d$ is 4-(3-amino-3-carboxypropoxy)-3-chlorophenyl, 2-amino-4-thiazolyl, 4-(3-t-butoxycarbonylamino-3-carboxy)-3-chlorophenyl, 3-(3-amino-3-carboxypropoxy)phenyl, 4-(3-carboxypropoxy)phenyl, or 4-(3-t-butoxycarbonylamino-3-carboxypropoxy)phenyl;

$R^e$ is hydroxy, methoxy or 2-t-butoxycarbonylaminoethoxy;

$R_d{}^2$ is a radical of the following formula;

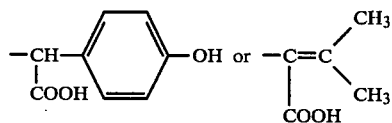

$R^f$ is hydrogen or lower alkoxycarbonyl;

$R^g$ is hydrogen or lower alkyl; and $R^{f'}$ is lower alkoxycarbonyl:

Examples of the definitions for the above symbols are illustrated below, respectively.

(1) With respect to the compound (I)

An acyl moiety in the acylamino for $R_1$ is intended to mean an acyl consisting of carbonyl radical (—CO—) or sulfonyl radical (—SO$_2$—) as stated hereinabove, including an aliphatic acyl, an aromatic acyl, a heterocyclic acyl and an aliphatic acyl whose aliphatic moiety is substituted by aromatic group or heterocyclic group. Examples of such acyl are illustrated in the following:

An aliphatic moiety in said aliphatic acyl may include saturated or unsaturated acyclic or cyclic hydrocarbon residue, in which the acyclic hydrocarbon residue may be branched and partially cyclized.

Suitable examples of said acyclic or alicyclic hydrocarbon residue (hereinafter referred to aliphatic-hydrocarbon residue) are mentioned in more concrete as follows:

alkyl (e.g., methyl, ethyl, propyl, butyl, isobutyl, pentyl, neopentyl, octyl, undecyl, tridecyl, pentadecyl, cyclohexylmethyl, cyclohexylethyl, bornanyl, etc.);

alkenyl (e.g., vinyl, propenyl, isopropenyl, 3-methylbutenyl, butenyl, 2-methylpropenyl, pentenyl, octadecenyl, 3-cyclohexenylmethyl, etc.);

alkynyl (e.g., ethynyl, Z-propynyl, etc.);

cycloalkyl (e.g., cyclopropyl, cyclopentyl, cyclohexyl, indenyl, borayl, adamantyl, etc.); and cycloalkenyl (e.g., 1-cyclopenten-1-yl, 2-cyclopenten-1-yl, 3-cyclohexene-1-yl, bornenyl etc.)

A suitable aromatic group in said aromatic acyl may include aryl such as phenyl, tolyl, naphthyl and the like.

A heterocyclic group in said heterocyclic acyl may include monocyclic or polycyclic heterocyclic group containing at least one hetero-atom selected from oxygen, sulfur nitrogen and the like. Suitable examples of said heterocyclic group are mentioned in more concrete as follows:

a 3- to 8-membered monocyclic heterocyclic group containing at least one sulfur atom (e.g., thienyl dihydrothiopyranyl, etc.);

a 3- to 8-membered monocyclic heterocyclic group containing at least one oxygen atom (e.g., oxiranyl, furyl, dihydrofuryl, pyranyl, dihydropyranyl, tetrahydropyranyl, dioxanyl, etc.);

a 3- to 8-membered monocyclic heterocyclic group containing at least one nitrogen atom (e.g., aziridinyl, azetidinyl, pyrrolyl, 2- or 3H-pyrrolyl, 2 or 3 pyrrolinyl, pyrrolidinyl, imidazolyl, imidazolidinyl, pyrazolyl, pyridyl, pyrimidyl, pyrazinyl, piperidinyl, pyridazinyl, tetrazolyl, etc.);

a 3- to 8-membered monocyclic heterocyclic group containing at least one oxygen atom and at least one nitrozen atom (e.g., oxazolyl, isoxazolyl, oxadiazolyl, sydnonyl, etc.);

a 3- to 8-membered monocyclic heterocyclic group containing at least one sulfur atom and at least one nitrogen atom (e.g., thiazolyl, isothiazolyl, thiadiazolyl, etc.);

a polycyclic heterocyclic group containing at least one sulfur atom (e.g., benzene-fused heterocyclic group such as benzothienyl, benzothiopyranyl, etc.);

a polycyclicheterocyclic group containing at least one nitrogen atom (e.g., indolyl, isoindolyl, indolizinyl, benzimidazolyl, quinolyl, isoquinoyl, dihydroisoqunolyl, quinazolyl, 1 or 2H-indazolyl, 1 or 2H-benzotriazolyl, purinyl, carbazolyl, etc.);

a polycyclic heterocyclic group containing at least one oxygen atom and at least one nitrogen atom (e.g. benzoxazolyl, benzoxadiazolyl, etc.); and a polycyclic heterocyclic group containing at least one sulfur atom and at least one nitrogen atom (e.g., benzothiazolyl, benzothiadiazolyl, etc.).

An aliphatic moiety in said aliphatic acyl whose aliphatic moiety is substituted by aromatic group or heterocyclic group is intended to mean the same meaning as defined in the above explanation of the aliphatic moiety in the aliphatic acyl, and include the same suitable examples thereof as stated in more concrete above. And in the same manner, each of the aromatic group and an heterocyclic group also are intended to mean the same meaning as defined in the above explanation of the aromatic group in the aromatic acyl and of the heterocyclic group in the heterocyclic acyl as well, and include the same suitable examples thereof as stated in more concrete above, respectively.

The optional carbon atom of the aliphatic acyl as defined above may be replaced and/or interrupted by one or more radicals selected from a bivalent aromatic radical, a bivalent heterocyclic radical, —O—, —N═, —S—, —SO—, —SO$_2$—, and —NH— whose hydrogen atom may be replaced by alkyl or aryl.

Each of the aliphatic moiety, aromatic group and heterocyclic group in the aliphatic acylamino, the aromatic acylamino, the heterocyclic acylamino and the aliphatic acylamino whose aliphatic moiety is substituted by aromatic group or heterocyclic group as defined above may optionally be substituted by one or more substituents selected from halogen, nitro, amino, carboxy, esterified carboxy, hydroxy, —N$_3$, —CN, —NHNH$_2$, ═O, ═NH, ═S, sulfo and ═NOH whose hydrogen atom may be replaced by alkyl or aralkyl, and the said heterocyclic group in the foregoing acylamino group may optionally be substituted by alkyl and/or an aromatic group.

Particularly, preferred examples of the aforementioned acylamino for R$_1$ may be illustrated as follows. As acylamino, the acyl moiety consisting of carbonyl radical (—CO—), i.e. organic carboxylic acylamino:
  alkanoylamino;
  alkenoylamino;
  aroylamino;
  heterocycle carboxamino;
  alkanoylamino substituted by aryl or heterocyclic group;
  alkenoylamino substituted by aryl or heterocyclic group;
  alkanoyl or alkenoyl amino, whose optional carbon chain(s) is interrupted by bivalent-aromatic radical and/or bivalent-heterocyclic radical;
  alkanoyl or alkenoyl amino substituted by aryl and/or heterocyclic group, in which an optional carbon chain(s) of the acyclic hydrocarbon moiety is interrupted by bivalent-aromatic radical and/or bivalent-heterocyclic radical;
  alkanoyl or alkenoyl amino substituted by aryl and/or heterocyclic group, in which an optional carbon chain(s) of the-acyclic hydrocarbon moiety is interrupted by one or more radicals selected from —O—, —N═,

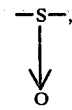

—SO$_2$—, and —NH— whose hydrogen atom may be replaced by alkyl or aryl;
  alkanoyl or alkenoyl amino substituted by aryl and/or heterocyclic group, in which an optional carbon chain(s) of the acyclic hydrocarbon moiety is interrupted by aromatic radical and/or bivalent heterocyclic radical, and further is interrupted by one or more radicals selected from —O—, —N═, —S—,

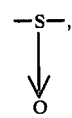

—SO$_2$—, and —NH— whose hydrogen atom may be replaced by alkyl or aryl;

alkanoyl or alkenoyl amino whose optional carbon chain is interrupted by one or more radicals selected from —O—, —N═, —S—,

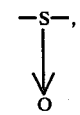

—SO$_2$—, and —NH— whose hydrogen atom may be replaced by alkyl or aryl;
alkanoyl or alkenoylamino whose optional carbon chain is interrupted to bivalent-aromatic radical and/or bivalent-heterocyclic radical and further interrupted by one or more radicals selected from —O—, —N═, —S—,

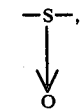

—SO$_2$—, and —NH— whose hydrogen atom may be replaced by alkyl or aryl;
aroylamino or heterocycle carboxamino, in which the bond between the ring and the carbonyl is interrupted by one or more radicals selected from —O—, —N═, —S—,

—SO$_2$—, and —NH—, whose hydrogen atom may be replaced by alkyl or aryl;
alkanoyl or alkenoyl amino substituted by cycloalkyl, aryl and/or heterocyclic group, in which the bond between the ring and the acyclic hydrocarbon moiety is interrupted by one or more radicals selected from —O—, —N═, —S—,

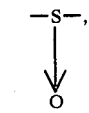

—SO$_2$—, and —NH—, whose hydrogen atom may be replaced by alkyl or aryl;
alkanoyl or alkenoyl amino substituted by cycloalkyl, aryl and/or heterocyclic group, in which each of the bond between the ring and the acyclic hydrocarbon moiety, and an optional carbon chain of the acyclic hydrocarbon moiety is interrupted by bivalent-aromatic radical and/or bivalent-heterocyclic radical, and/or one or more radicals selected from —O—, —N═, —S—, —SO₂— and —NH—, whose hydrogen atom may be replaced by alkyl or aryl;

aroylamino or heterocycle carboxamino in which the bond between the ring and the carbonyl is interrupted by one or more bivalent-aromatic radical and/or bivalent-heterocyclic radical;

alkanoyl or alkenoyl amino substituted by aryl and/or heterocyclic group, in which the bond between the ring and the acyclic hydrocarbon moiety are interrupted by bivalent-aromatic radical and/or bivalent-heterocyclic radical, and further one or more radicals selected from —O—, —N=, —S—,

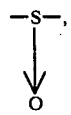

—SO₂— and —NH—, whose hydrogen atom may be replaced by alkyl or aryl, and alkanoyl or alkenoyl amino substituted by aryl and/or heterocyclic group, in which the bond between the ring and the acyclic hydrocarbon moiety is interrupted by one or more bivalent-aromatic radicals and/or bivalent-heterocyclic radicals;

An optional carbon atom of above defined acylamino group may be substituted by one or more substituents selected from halogen, nitro, amino, carboxy, esterified carboxy, hydroxy, —N₃, —CH, —NHNH₂, =O, =NH, =S, sulfo, =NOH whose hydrogen atom may be replaced by alkyl or aralkyl, and the heterocyclic group in the foregoing acylamino group may optionally be substituted by alkyl.

As acylamino, the acyl moiety consisting of sulfonyl radical (—SO₂—), i.e. organic sulfonic acylamino: Preferred examples of the organic sulfonic acylamino can be exemplified by an acylamino, in which "carbonyl radical (—CO—)" in the preferred examples of the acylamino as exemplified above is replaced by "sulfonyl radical (—SO₂—)". Accordingly, preferred examples of the organic sulfonic acylamino are to be referred to the preferred examples of the organic carboxylic acylamino by changing "oylamino" in the terms of the preferred examples to read as—e(or ene)sulfonylamino—, for example, "alkanoylamino" to read as—alkanesulfonylamino—, "alkenoylamino" to—alkenesulfonylamino—, "aroylamino" to—arenesulfonylamino and so on.

alkanoylamino, in which an optional carbon chain is interrupted by one phenylene and further optional carbon atoms are substituted by one halogen and one oxo;

phenylalkanoylamino, in which an optional carbon atom may be substituted by one substituted selected from amino, carboxy, esterified carboxy, hydroxy, halogen, nitro, sulfo, oxo, hydroxyimino and benzyloxyimino;

naphthylalkanoylamino;

dihydropyranylalkanoylamino, in which an optional carbon atom is substituted by one hydroxy;

morpholinoalkanoylamino;

thienylalkanoylamino in which an optional carbon atom may be substituted by one substituent selected from amino, hydroxy, oxo and hydroxyimino;

furylalkanoylamino;

tetrazolylalkanoylamino;

indolylalkanoylamino, in which an optional carbon atom is substituted by one amino;

diphenylalkanoylamino;

alkanoylamino substituted by phenyl and thienyl;

3-alkyl-1,2,5-oxadiazol-4-yl-alkanoylamino;

phenylalkenoylamino;

phenylalkanoylamino, in which an optional carbon chain of the alkane moiety is interrupted by one phenylene;

phenylalkanoylamino, in which an optional carbon chain of alkane moiety is interrupted by one or two bivalent radicals selected from —O—, —N=, —S—, —NH—,

and

and further an optional carbon atom(s) of the group thus defined may be substituted by one to four substituents selected from amino, carboxy, esterified carboxy, halogen, oxo and =NH;

thienylalkanoylamino, in which an optional carbon chain(s) of the alkane moiety is interrupted by one of two bivalent radicals selected from —O—, —S— and —NH—, and further an optional carbon atom(s) of the group thus defined is substituted by one to four substituents selected from amino, carboxy, halogen and oxo;

dihydropyranylalkanoylamino, in which an optional carbon chain of the alkane moiety is interrupted by —NH— and an optional carbon atom of the group thus defined is substituted by halogen;

diphenylalkanoylamino, in which an optional carbon chain(s) of the alkane moiety is interrupted by one to three bivalent radicals selected from —O—, —N= and —NH—, and further an optional carbon atom(s) of the group thus defined may be substituted by one or two substituents selected from carboxy, hydroxy and oxo;

alkanoylamino substituted by phenyl and thienyl, in which an optional carbon chain(s) of the alkane moiety is interrupted by one to two bivalent radicals selected from —O—, —N= and —NH—, and further an optional carbon atom(s) of the group thus defined may be substituted by one to five substituents selected from amino, halogen, oxo and thioxo;

alkanoylamino substituted by phenyl and indolyl, in which an optional carbon chain(s) of the alkane moiety is interrupted by one —O— and one —NH—, and further an optional carbon atom of the group thus defined is substituted by one oxo;

alkanoylamino substituted by phenyl and benzo[d]isoxazolyl, in which an optional carbon chain(s) of the alkane moiety is interrupted by one —O— and one —NH—, and further an optional carbon atom of the group thus defined is substituted by one oxo;

phenylalkanoylamino, in which an optional carbon chain(s) of the alkane moiety is interrupted by one or two bivalent radicals selected from phenylene, 2-oxo-azetidin-1, 3-diyl, 1,3,4-thiadiazol-1,5-diyl and 1,3-oxazolidin-3,4-diyl and one to four bivalent radicals selected from —O—, —N═, —S—, —NH— and

and further an optional atom(s) of the group thus defined may be substituted by one to six substituents selected from amino, halogen, hydroxy, esterified carboxy, oxo, hydroxyimino, benzyloxyimino and hydrazino;

thienylalkanoylamino, in which an optional carbon chain(s) of the alkane moiety is interrupted by one phenylene, and two bivalent radicals of selected from —O— and —NH— and further an optional carbon atom(s) of the group thus defined is substituted by carboxy, oxo and hydroxyimino.

benzo[c]pyrrolidinylalkanoylamino, in which an optional carbon chain of the alkane moiety is interrupted by one phenylene and one —O—, and further optional carbon atoms of the group thus defined are substituted by four substituents selected from amino, carboxy, hydroxy, esterified carboxy, oxo, hydroxyimino and methoxyimino;

diphenylalkanoylamino, in which optional carbon chain(s) of the alkane moiety are interrupted by one phenylene and one —O— and one —NH—, and further an optional carbon atom(s) of the group thus defined is substituted by two to four substituents selected from amino, halogen, nitro, oxo and hydroxyimino;

alkanoylamino substituted by phenyl and furyl, in which optional carbon chains of the alkane moiety are interrupted by one phenylene and one —NH— and one —O— and further an optional carbon atom(s) of the group thus defined is substituted by three substituents selected from halogen and oxo;

alkanoylamino, in which an optional carbon chain(s) is interrupted by one or two bivalent radicals selected from —O—, —S—, —NH—, —SO₂— and

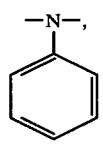

and further an optional carbon atom(s) of the group thus defined may be substituted by one to two substituents selected from amino, azido, carboxy, hydroxy, oxo, thioxo and ═NH;

alkenoylamino, whose optional carbon chain is interrupted by one —S—;

alkanoylamino, in which an optional carbon chain(s) is interrupted by one or two phenylenes and one to five bivalent radicals selected from —O—, —N═, —S—, —NH— and

and further an optional carbon atom(s) of the group thus defined may be substituted by one to seven substituents selected from amino, carboxy, hydroxy, halogen, azido, sulfo, esterified carboxy, oxo, thioxo, hydroxyimino and methoxyimino;

alkanoylamino, in which an optional carbon chain is interrupted by one 1,3,4-thiadiazol-2,5-diyl and one or two bivalent radicals selected from —S— and —NH—, and further an optional carbon atom(s) of the group thus defined is substituted by one or six substituents selected from amino, hydroxy and oxo;

alkenoylamino, in which an optional carbon chain is interrupted by one phenylene and one or two bivalent radicals selected from —O— and —NH—, and further an optional carbon atom(s) of the group thus defined is substituted by one or three substituents selected from carboxy, esterified carboxy, nitro, oxo and hydroxyimino;

1,2-oxazolidinylcarbonylamino, in which the bond between the 1,2-oxazolidinyl and the carbonyl is interrupted by —NH—, and further an optional carbon atom of the group thus defined is substituted by one oxo;

bicyclo[2,2,1]heptylalkanoylamino, in which the bond between the bicyclo[2,2,1]heptyl and the alkane moiety is interrupted by one —O—, and further an optional carbon atom(s) of the bicyclo[2,2,1]heptane ring is substituted by three alkyl;

phenylalkanoylamino in which the bond between the phenyl and the alkane moiety is interrupted by one or two bivalent radicals selected from —O—, —S—, —NH— and —SO₂—, and further an optional carbon atom of the group thus defined may be substituted by one substituent selected from halogen and nitro;

naphthylalkanoylamino, in which the bond between the naphthyl and the alkane moiety is interrupted by bivalent radical selected from —O— and —NH—;

pyridylalkanoylamino, in which the bond between the pyridyl and the alkane moiety is interrupted by one —O—;

1,3,4-thiadiazolylalkanoylamino, in which the bond between the 1,3,4-thiadiazolyl and the alkane moiety is interrupted by one —S—;

1H-1,2,3-benzotriazolylalkanoylamino, in which the bond between the 1H-1,2,3-benzotriazolyl and the alkane moiety is interrupted by one —O—;

pyridyl-1-oxidealkanoylamino, in which the bond between the pyridyl-1-oxide and the alkane moiety is interrupted by one —S—;

diphenylalkanoylamino, in which the bond between the one or two phenyl and the alkane moiety is interrupted by one or two bivalent radicals selected from —O—, —S—, —NH— and —SO₂—, and further an optional carbon atom(s) of the group thus defined is substituted by one or two substituents selected from nitro, carboxy, halogen, hydroxy and oxo;

alkanoylamino substituted by phenyl and naphthyl, in which the bond between the naphthyl and the alkane moiety is interrupted by one —O—;

alkanoylamino substituted by phenyl and pyrimidinyl, in which the bond between the pyrimidinyl and the alkane moiety is interrupted by —S—, and further an optional carbon atom(s) of the group thus defined is substituted by one amino and one hydroxy;

alkanoylamino substituted by bicyclo[2,2,1]heptyl and phenyl, in which the bond between the bicyclo[2,2,1]-heptyl and the alkane moiety is interrupted by one —O— and an optional carbon chain of the alkane moiety is interrupted by one —NH—, and further an optional carbon atom of the alkane moiety is substituted by oxo and optional carbon atoms of the bicyclo[2,2,1]heptane ring are substituted by three alkyl;

diphenylalkanoylamino, in whcih the bond between one of the diphenyl and the alkane moiety is interrupted by one or two bivalent radicals selected from —O—, —NH—, —S—,

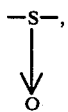

—SO$_2$— and

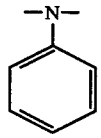

and an optional carbon chain of the alkane moiety is interrupted by one or two bivalent radicals selected from —NH— and —S—, and further an optional carbon atom(s) of the group thus defined is substituted by one to three substituents selected from carboxy, esterified carboxy, halogen, nitro and oxo;

alkanoylamino substituted by 9H-purinyl and phenyl, in which the bond between the 9H-purinyl and the alkane moiety is interrupted by one —S— and an optional carbon chain of the alkane moiety is interrupted by one —NH—, and further an optional carbon atom of the group thus defined is substituted by one oxo;

alkanoylamino substituted by phenyl and thienyl, in which the bond between the phenyl and the alkane moiety is interrupted by one bivalent radical selected from —O— and —NH— and an optional carbon chain of the alkane moiety is interrupted by one —NH—, and further optional carbon atoms of the group thus defined are substituted by three substituents selected from esterified carboxy, halogen, nitro and oxo;

alkanoylamino substituted by phenyl and pyridyl-1-oxide, in which the bond between the pyridyl-1-oxide and the alkane moiety is interrupted by one —S— and an optional carbon chain of the alkane moiety is interrupted by one —NH—, and further an optional carbon atom of the group thus defined is substituted by oxo;

alkanoylamino substituted by naphthyl and phenyl, in which the bond between the naphthyl and the alkane moiety is interrupted by one bivalent radical selected from —O— and —NH— and an optional carbon chain of the alkane moiety is interrupted by one or two bivalent radicals selected from —O—, —S—, —NH— and

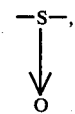

and further an optional carbon atom of the group thus defined is substituted by oxo;

alkanoylamino substituted by phenyl and pyrimidinyl, in which the bond between the pyrimidinyl and the alkane moiety is interrupted by one —S— and an optional carbon chain of the alkane moiety is interrupted by one —NH—, and further optional carbon atoms of the group thus defined are substituted by one amino, one hydroxy and one oxo;

triphenylalkanoylamino, in which the bond between the one or two phenyls and the alkane moiety is interrupted by one or two bivalent radicals selected from —O— and —NH— and an optional carbon chain of the alkane moiety is interrupted by one —NH—, and further an optional carbon atom(s) of the group thus defined is substituted by one or two substituents selected from halogen and oxo;

alkanoylamino substituted by naphthyl and diphenyl, in which the bond between the naphthyl and the alkane moiety is interrupted by one —O— and an optional carbon chain of the alkane moiety is interrupted by one —NH—, and further an optional carbon atom of the group thus defined is substituted by oxo;

alkanoylamino substituted by dinaphthyl and phenyl, in which the bond between the two naphthyl and the alkane moiety is interrupted by one —O— and an optional carbon chain of the alkane moiety is interrupted by one —NH—, and further an optional carbon atom of the group thus defined is substituted by oxo;

phenylalkanoylamino, in which the bond between the phenyl and the alkane moiety is interrupted by one bivalent radical selected from —O—, —NH— and —S— and optional carbon chains of the alkane moiety are interrupted by one phenylene and one to three bivalent radicals selected from —O— and —NH—, and further an optional carbon atom(s) of the group thus defined is substituted by one to five substituents selected from carboxy, esterified carboxy, halogen, nitro, oxo, thioxo and hydroxyimino;

naphthylalkanoylamino, in which the bond between the naphthyl and the alkane moiety is interrupted by one —NH— and optional carbon chains of the alkane moiety are interrupted by one phenylene and three bivalent radicals selected from —O— and —NH—, and further optional carbon atoms of the group thus defined are substituted by one carboxy, one oxo and one thioxo;

alkanoylamino substituted by pyridyl and phenyl, in which the bond between the pyridyl and the alkane moiety is interrupted by one —S— and the optional carbon chains of the alkane moiety are interrupted by two phenylenes and three bivalent radicals selected from —O— and —NH—, and further optional carbon atoms of the group thus defined are substituted by four substituents selected from halogen and oxo;

alkanoylamino substituted by phenyl and benzo[c]pyrrolidinyl, in which the bond between the phenyl and the alkane moiety is interrupted by one —NH— and an optional carbon chain(s) of the alkane moiety is interrupted by one phenylene and one —O—, and further optional carbon atoms of the group thus defined are substituted by five substituents selected from carboxy, esterified carboxy, nitro and oxo;

diphenylalkanoylamino, in which the bond between the one or two phenyls and the alkane moiety is interrupted by one or two —NH— and an optional carbon chain(s) of the alkane moiety is interrupted by one phenylene and one to three bivalent radicals selected from —O— and —NH—, and further an optional carbon atom(s) of the group thus defined is substituted by one to five substituents selected from carboxy, nitro, esterified carboxy, oxo and thioxo;

dinaphthylalkanoylamino, in which bonds between the two naphthyl and the alkane moiety are interrupted by one —NH— and optional carbon chains of the alkane moiety are interrupted by one phenylene and three bivalent radicals selected from —O— and —NH—, and further optional carbon atoms of the group thus defined are substituted by three substituents selected from carboxy and thioxo;

alkanoylamino substituted by phenyl and thienyl, in which the bond between the thenyl and the alkane moiety is interrupted by one tetrazol-1,5-diyl and an optional carbon chain of the alkane moiety is interrupted by one —NH—, and further an optional carbon atom of the group thus defined is substituted by one oxo;

phenylalkanoylamino, in which the bond between the phenyl and the alkane moiety is interrupted by one —O— and an optional carbon chain of the alkane moiety is interrupted by one —NH—, and further the optional carbon atoms of the group thus defined are substituted by one halogen, one nitro and one oxo;

diphenylalkanoylamino, in which the bond between the phenyl and the alkane moiety is interrupted by one phenylene and one —O— and an optional carbon chain of the alkane moiety is interrupted by one —NH—, and further an optional carbon atom of the group thus defined is substituted by one oxo;

diphenylalkanoylamino, in which the bond between the phenyl and the alkane moiety is interrupted by one isoxazol-3,4-diyl which is substituted by one alkyl and an optional carbon chain of the alkane moiety is interrupted by one —NH—, and further an optional carbon atom of the group thus defined is substituted by one oxo;

benzamido, in which the bond between the phenyl and the carbonyl is interrupted by isoxazol-3,4-diyl which is substituted by one alkyl, and further an optional carbon atom of the group thus defined is substituted by halogen;

phenylalkanoylamino, in which the bond between the phenyl and the alkane moiety is interrupted by one bivalent radical selected from phenylene and 1,3,5-oxadiazol-2,4-diyl and one or two bivalent radicals selected from —O—, —NH— and —SO$_2$—, and further the optional carbon atom of the group thus defined may be substituted by one carboxy and one hydroxy;

phenylalkanoylamino, in which the bond between the phenyl and the alkane moiety is interrupted by one 4,5-dihydro-1,2,4-oxadiazol-3,4-diyl, and an optional carbon atom of the group thus defined is substituted by one oxo;

thienylalkanoylaimo, in which the bond between the thienyl and the alkane moiety is interrupted by 1H-tetrazol-1,5-diyl.

As acylamino, the acyl moiety consisting of sulfonyl radical (—SO$_2$—), i.e. organic sulfonic acylamino: Preferred examples of the organic sulfonic acylamino can be exemplified by an acylamino, in which "carbonyl radical (—CO—)" in the preferred examples of the acylamino as exemplified above is replaced by "sulfonyl radical (—SO$_2$—)". Accordingly, preferred examples of the organic sulfonic acylamino are to be referred to the preferred examples of the organic carboxylic acylamino by changing "oylamino" in the terms of the preferred examples to read as—e(or ene)sulfonylamino—, for example, "alkanoylamino" to read as—alkanesulfonylamino—, "alkenoylamino" to—alkenesulfonylamino—, "aroylamino" to—arenesulfonylamino and so on.

(2) With respect to the compounds [I],[I'] and [II]:

Suitable examples of alkyl containing up to 6 carbon atoms in the definition for $R^Y$ may include methyl, ethyl, propyl, butyl, pentyl and isopropyl.

Suitable examples of alkoxy containing up to 6 carbon atoms in the definition for $R^Y$ may include methoxy, ethoxy, propoxy, butoxy, pentyloxy and isopropoxy.

Suitable examples of aralkoxy containing up to 12 carbon atoms in the definition for $R^Y$ may include benzyloxy, phenethyloxy, phenylpropoxy, phenylbutoxy and the like.

Suitable examples of alkylthio containing up to 6 carbon atoms in the definition for $R^Y$ may include methylthio, ethylthio, propylthio, butylthio, pentylthio and the like.

Suitable examples of halogen in the definition for $R^Y$ may include chlorine, bromine, iodine and the like.

Suitable examples of alkylidene containing up to 6 carbon atoms in the definitions for $R^X$ and $R^Y$ may include methylene, ethylidene, propylidene, butylidene and the like.

Suitable examples of pharmaceutically acceptable salts may include salt with inorganic base (e.g., sodium salt, potassium salt, magnesium salt, ammonium salt, etc.), and organic base (e.g., dicyclohexylamine salt, pyridine salt, ethanolamine salt, etc.).

Suitable examples of the derivative of the carboxy for $R^Z$ which is to be understood to be included within the scope of this invention may include an ester and an acid amide, and are exemplified as follows.

(a) Ester:

Esters are conventional ones, including silyl esters, aliphatic esters and esters containing an aromatic or a heterocyclic ring.

The suitable silyl esters may be illustrated by examples of tri(lower)alkylsilyl (e.g., trimethylsilyl, triethylsilyl, etc.) esters, etc.

The suitable aliphatic esters may include saturated or unsaturated acyclic or cyclic aliphatic esters which may be branched or which may contain a cyclic ring, such as aliphatic esters, for example, lower alkyl (e.g., methyl, ethyl, propyl, isopropyl, 1-cyclopropylethyl, butyl, tertbutyl, octyl, nonyl, undecyl, etc.) esters; alkenyl (e.g., vinyl, 1-propenyl, allyl, 3-butenyl, etc.) esters; alkynyl (e.g., 3-butynyl, 4-pentynyl, etc.) esters; cycloalkyl (e.g., cyclopentyl, cyclohexyl, cycloheptyl, etc.) esters; etc., and aliphatic esters containing at least one heteroatom of nitrogen, sulfur or oxygen atom, for example, lower alkoxyalkyl (e.g., methoxymethyl, ethoxyethyl, methoxyethyl, etc.) esters; lower alkanoyloxyalkyl (e.g., acetoxymethyl, propionyloxymethyl, pivaloyloxymethyl) esters; alkylthioalkyl (e.g., methylthiomethyl, ethylthioethyl, methylthiopropyl, etc.) esters; lower alkylsulfinyl(lower)alkyl (e.g., methylsulfinylmethyl, ethylsulfinylmethyl, etc.) esters, etc.

The suitable esters containing an aromatic ring may include, for example, aryl (e.g., phenyl, xylyl, tolyl, naphthyl, indanyl, dihydroanthryl, etc.) esters; aralkyl (e.g., benzyl, phenethyl) esters; aryloxyalkyl (e.g., phenoxymethyl, phenoxyethyl, phenoxypropyl, etc.) esters; arylthioalkyl (e.g., phenylthiomethyl, phenylthioethyl, phenylthiopropyl, etc.) esters; arylsulfinylalkyl (e.g., phenylsulfinylmethyl, phenylsulfinylethyl, etc.) esters; aryloxyalkyl (e.g., benzoylmethyl, toluoylethyl, etc.) esters; aryloylamino (e.g., phthalimido, etc.) esters; etc.;

The suitable esters containing an heterocyclic ring may include, for example, heterocyclic esters, heterocyclicalkyl esters, etc.; in which the suitable heterocyclic ester may include, for example, saturated or unsaturated, condensed alkanesulfonylphenyl (e.g., 4-methanesulfonylphenyl, 2-ethanesulfonylphenyl, etc.) esters, 2-(or 3 or 4-)phenylazophenyl esters, mono(or di or tri)nitrophenyl (e.g., 4-nitrophenyl, 2,4-dinitrophenyl, 3,4,5-trinitrophenyl, etc.) esters, mono(or di or tri or tetra or penta)halophenyl(lower)alkyl (e.g., 2-chlorobenzyl, 2,4-dibromobenzyl, 3,4,5-trichlorobenzyl, pentachlorobenzyl, etc.) esters, mono(or di or tri)nitrophenyl(lower)alkyl (e.g., 2-nitrobenzyl, 2,4-dinitrobenzyl, 3,4,5-trinitrobenzyl, etc.) esters, mono(or di or tri)(lower)alkoxyphenyl(lower)alkyl (e.g., 2-methoxybenzyl, 3,4-dimethoxybenzyl, 3,4,5-trimethoxybenzyl, etc.) esters, hydroxy and di(lower)alkylphenyl(lower)alkyl (e.g., 3,5-dimethyl-4-hydroxybenzyl, 3,5-ditert-butyl-4-hydroxybenzyl, etc.) esters, etc.

(b) Acid amide:

The suitable acid amides may include, for example, N-unsubstituted acid amide, N-lower alkyl acid amide (e.g., N-methyl acid amide, N-ethyl acid amide, etc.), N,N-di(lower)alkyl acid amide (e.g, N,N-dimethyl acid amide, N,N-diethyl acid amide, N-methyl-N-ethyl acid amide, etc.), N-phenyl acid amide, or an acid made with pyrazole, imidazole, 4-lower alkylimidazole (e.g., 4-methylimidazole, 4-ethylimidazole, etc.), etc.

(3) With respect to the compound (IV):

Suitable examples of alkyl moiety in the definition for "Y" may include methyl, ethyl, propyl, butyl, pentyl, isopropyl, isobutyl, t-butyl and the like.

Suitable examples of the protected group in protected amino or protected hydroxy in the definition for "Y" may include a conventional acyl such as alkanoyl (e.g., formyl, acetyl, etc.), haloalkanoyl (e.g., dichloroacetyl, trifluoroacetyl, etc.), aroyl (e.g., benzoyl, toluoyl, etc.), alkoxycarbonyl (e.g., ethoxycarbonyl, tertbutoxycarbonyl, adamantyloxycarbonyl, etc.), haloalkoxycarbonyl (e.g., trichloroethoxycarbonyl, etc.), substituted or unsubstituted aralkoxycarbonyl (e.g., benzyloxycarbonyl, p-nitrobenzyloxycarbonyl, etc.) and the like.

(4) With respect to the compounds (VII) and (VIII):

Suitable examples of aralkyl for $R'_3$ may include benzyl, diphenylmethyl, trityl, phenethyl, phenylpropyl and the like.

(5) With respect to the compound (I'), (XXXXXVIII), (XXXXXIX), (XXXXXX), (XXXXXXI), (XXXXXXII) and (XXXXXXIII):

Suitable examples of acyl in the acylamino for $R_1$ may include the same ones as illustrated before for the acyl in the definition for $R_1$.

(6) With respect to the compound (I'):

Suitable examples of groups for "A" may include the same ones as illustrated for the groups in the definition for "A" excepting hydrogen.

(7) With respect to the compounds (V), (VI), (VII), (VIII), (X), (XXI), (XXIX), (XXX), (XXXIII) and (XXXIV):

A suitable acyl moiety in the acyl amino for $R_2$, $R_3$, $R_8$, $R_{10}$, $R_{20}$, $R_{22}$, $R_{28}$, $R_{29}$, $R_{34}$, $R_{36}$ and $R_{38}$, and in the acyloxy for $R_{10}$ and in the acyloxyimino for $R_{35}$, $R_{36}$, $R_{37}$ and $R_{38}$ may include the same aliphatic acyl, aromatic acyl, heterocyclic acyl and aliphatic acyl whose aliphatic moiety is substituted by aromatic group or heterocyclic group as illustrated for the acyl in the acylamino for $R_1$. Accordingly, the detail of explanation, preferred examples, etc. of said acyl moiety is to be referred to the descriptions for the acyl in the acylamino for $R_1$ as made hereinabove.

Preferred examples of the above acyl may be: alkanoyl or cycloalkanoyl (e.g., formyl, acetyl, propionyl, butyryl, isobutyryl, pivaloyl, cyclohexanecarbonyl, etc.); aralkanoyl (e.g., phenylacetyl, phenylpropionyl, naphthylacetyl, etc.); heterocyclic alkanoyl (e.g., thienylacetyl, tetrazolylacetyl, furylacetyl, thiadiazolylacetyl, thiazolylacetyl, morpholinoacetyl, piperazinoacetyl, benzothiazolylacetyl, thienylpropionyl, etc.); aroyl (e.g., benzoyl, toluoyl, xyloyl, naphthoyl, phthaloyl, etc.); heterocyclic carbonyl (e.g., thenoyl, furoyl, prolyl, nicotinoyl, isonicotinoyl, benzodioxanecarbonyl, etc.) or cycloalkylalkanoyl (e.g., cyclopentylacetyl, cyclohexylacetyl, etc.).

In the above examples; the optional bond of the alkylene moiety, the bond between the carbonyl and the aliphatic, aromatic or heterocyclic group, and/or the bond between the alkylene and the cycloalkyl, aryl or heterocyclic group may be interrupted by a bivalent radical —O—, —S— or —NH—. Suitable examples of such acyl may be alkoxycarbonyl (e.g., methoxycarbonyl, ethoxycarbonyl, propoxycarbonyl, tertbutoxycarbonyl, etc.); cycloalkoxycarbonyl (e.g., cyclopropoxycarbonyl, cyclohexyloxycarbonyl, bornyloxycarbonyl, adamantyloxycarbonyl, etc.); aralkoxycarbonyl (e.g., benzyloxycarbonyl, phenethyloxycarbonyl, etc.); heterocyclic alkoxycarbonyl (e.g., furfuryloxycarbonyl, pyrrolidinyloxycarbonyl, pyridylmethoxycarbonyl, etc.); aryloxycarbonyl (e.g., phenoxycarbonyl, naphthoxycarbonyl, etc.); alkoxythiocarbonyl (e.g., methoxythiocarbonyl, ethoxythiocarbonyl, propoxythiocarbonyl, etc.); alkoxyalkanolyl (e.g., methoxyacetyl, ethoxypropionyl, etc.); cycloalkoxyalkanoyl (e.g., cyclohexyloxyacetyl, bornyloxyacetyl, adamantyloxyacetyl, etc.); alkylthioalkanoyl (e.g., methylthioacetyl, ethylthioacetyl, isopropylthioacetyl, butylthioacetyl, etc.); arylthioalkanoyl (e.g., phenylthioacetyl, etc.); heterocyclothioalkanoyl (e.g., thienylthioactyl, thienylthiopropionyl, thiazolylthioacetyl, thiadiazolylthioacetyl, oxazolylthioacetyl, oxadiazolylthioacetyl, triazolylthioacetyl, tetrazolylthioacetyl, benzothiazolylthioacetyl, etc.); N-alkylcarbamoyl (e.g., N- methylcarbamoyl, N-ethylcarbamoyl etc.); N-arylcarbamoyl (e.g., N-phenylcarbamoyl, N-naphthylcarbamoyl, etc.); N-alkylthiocarbamoyl (e.g., N-methylthiocarbamoyl, N-ethylthiocarbamoyl, etc.), N-arylthiocarbamoyl (e.g., N-phenylthiocarbamoyl, etc.) and the like.

The optional carbon atom of said acyl group may be substituted by one or more suitable substituents such as a halogen atom (e.g., chlorine, bromine, etc), nitro or formyl.

(8) With respect to the compound (XI):

Suitable examples of acid residue for $X_1$ may include an acid residue of:

an inorganic acid (e.g., hydrochloric, hydrobromic, hydroiodic, sulfuric acid, etc.), an organic acid such as organic sulfonic acid (e.g., methanesulfonic, benzenesulfonic or toluenesulfonic acid), an organic carbamic acid (e.g., dimethylcarbamic or diethylcarbamic acid, etc.).

Suitable examples of bivalent aliphatic hydrocarbon radial in the definition for "$A_1$" may include alkylene or alkenylene (e.g., methylene, ethylene, trimethylene, propylene, propenylene, butenylene, hexamethylene, etc.), in which the optional carbon atom may be replaced by at least one radicals selected from —NH—, —O—, and

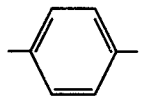

and further may be substituted by oxo, aryl such as phenyl, naphthyl, etc. or heterocyclic group such as thienyl.

(9) With respect to the compound (XII):

Suitable examples of residue of nucleophile in the definition for $R_{11}$ may include (a) the residue S-nucleophile such as substituted or unsubstituted alkylthio (e.g., methylthio, ethylthio, propylthio, isopropylthio, etc.); alkenylthio (e.g., vinylthio, propenylthio, isopropenylthio, butenylthio, etc.); alkynylthio (e.g., 2-propynylthio, etc.); arylthio (e.g., phenylthio, naphthylthio, etc.); substituted or unsubstituted aralkylthio (e.g., benzylthio, phenethylthio, phenylpropylthio, phenylbutylthio, etc.), in which the optional carbon atom of said alkyl moiety may be replaced by at least one radical selected from —O—, —NH— and further may be substituted by oxo; substituted or unsubstituted heterocyclicthio (e.g., morpholinylthio, thiadiazolylthio, oxadiazolylthio, triazolylthio, pyrimidinylthio, oxazolylthio, tetrazolylthio, purinylthio, pyridin-1-oxide-2-ylthio, 5-methyl-1,3,4-thiadiazolylthio, 5-ethyl-1,3,4-thiadiazolylthio, 1-methyltetrazolylthio, 2-aminothiazolylthio, 1-methyltriazolylthio, etc.); (b) the residue of O-nucleophile such as substituted or unsubstituted aryloxy 8e.g., phenoxy, tolyloxy, chlorophenoxy, biphenylyloxy, naphthoxy, methoxyphenoxy, phenoxyphenoxy, vinylphenoxy, propenylphenoxy, acetylpheenoxy, benzoylphenyloxy, benzoylnaphthoxy, etc.); and (c) the residue of N-nucleophile such as substituted or unsubstituted arylamino (e.g., anilino, N-methylanilino, naphthylamino, etc.) or substituted or unsubstituted aralkylamino (e.g., benzylamino, N-methylbenzylamino, phenethylamino, naphthylmethylamino, etc.).

In the above, the residue of nucleophile may be substituted by at least one substituent selected from carboxy, esterified carboxy (e.g., methoxycarbonyl, ethoxycarbonyl, propoxycarbonyl, etc.), halogen (e.g., bromine, chlorine, etc.), nitro, formyl amino, hydroxy, protected amino or protected hydroxy and the like.

(10) With respect to compounds (XIII) and (XIV):

Suitable example of acyl moiety in an acyl having protected amino, protected hydroxy and/or protected carboxy for $R_{12}$ may include the same ones as defined and illustrated before for the acyl in the acylamino for $R_1$.

Suitable example of acyl moiety of an acyl having amino, hydroxy or carboxy function in $R'_{22}$ may include the same ones as defined and illustrated before for the acyl in the acylamino for $R_1$.

Suitable examples of alkyl in the definition for $R_{13}$ may include methyl, ethyl, propyl and the like.

Suitable example of acyl for $R_{13}$ may include the same ones as defined and illustrated for the acyl in the acylamino for $R_1$, and suitable examples of aralkyl for $R_{13}$ may include benzyl and phenethyl.

Suitable halogen in the definition for $X_2$ may include bromine, chlorine and the like.

(11) With respect to compounds (XV) and (XVI):

Suitable example of acyl for $R_{14}$ may include the same ones as defined and illustrated for the acyl in the acylamino for $R_1$, and more particularly aroyl (e.g., benzoyl, naphthoyl, etc.), aralkanoyl (e.g., phenylacetyl, phenylpropionyl, etc.); heterocyclic-alkanoyl such as thienylalkanoyl (e.g., thienylacetyl, thienylpropionyl, thienylbutyryl, etc.); an alkoxyaralkanoyl, in which the optional carbon atom is substituted by at least one substituent selected from hydroxyimino, carboxy, amino, protected amino and the like, the examples of which are illustrated as follows.

2-[4-(3-carboxy-3-acetamidopropoxy)phenyl]-2-hydroxyiminoacetyl,

2-[4-{3-carboxy-3-(3-phenylureido)propoxy}phenyl]-2-hydroxyiminoacetyl,

2-[4-{3-(2,2,2-trifluoroacetamido)-3-carboxypropoxy} phenyl]-2-hydroxyiminoacetyl, etc.

Suitable examples of halogen for $X_3$ and $X_4$ may be the same ones as illustrated before for the halogen for $X_2$.

(12) With respect to the compounds (XVII) and (XVIII):

Suitable examples for the definition for $R_{15}$ are as follows: alkyl (e.g., methyl, ethyl, propyl, etc.); aryl (e.g., phenyl, naphthyl, etc.); aralkyl (e.g., benzyl, phenylpropyl, etc.); aryloxy (e.g., phenoxy, naphthoxy, etc.); heterocyclic group (e.g., thienyl, pyranyl, 5,6-dihydro-2H-pyranyl, isobenzofuranyl, indolyl, etc.); heterocyclicalkyl (e.g., thienylmethyl, thienylpropyl, furylmethyl, furylethyl, furylpropyl, indolylethyl, thiadiazolylmethyl, thiadiazolylethyl, oxazolylmethyl, etc.).

Suitable examples of hydrocarbon residue having amino in the definition for $R_{16}$ may include aminoalkyl (e.g., aminomethyl, aminoethyl, aminopropyl, etc.), and aminoaryl (e.g., aminophenyl, aminonaphthyl, etc.), and the like.

Suitable examples for the definition for $R_{17}$ are as follows.

The hydrocarbon moiety in acylamino-substituted-hydrocarbon residue for $R_{17}$ may include alkyl (e.g., methyl, ethyl, propyl, butyl, pentyl, hexyl, etc.); alkenyl (e.g., vinyl, propenyl, isopropenyl, etc.); aryl (e.g., phenyl, naphthyl, etc.); aralkyl (e.g., benzyl, phenethyl, phenylpropyl, phenylbutyl, etc.), and the optional carbon atom of said hydrocarbon moiety may be substituted by at least one substituent selected from halogen (e.g., bromine, chlorine, etc.), hydroxy, carboxy, and the like, and further optional carbon atom of said hydrocarbon moiety may be replaced by at least one radical selected from oxygen, nitrogen, sulfur, imino, carbonyl, thiocarbonyl and carbamoyl.

And suitable examples of the acyl moiety in acylamino and acylamino-substituted-hydrocarbon residue for $R_{17}$ are the same ones as defined and illustrated before for the acyl in the acylamino for $R_1$.

(13) With respect to compounds (XIX) and (XX):

Suitable examples of aryl for $R_{18}$ may be the same as mentioned above.

Suitable examples of the alkyl and aryl for $R_{19}$ may be the same as mentioned above.

Suitable examples of N-arylcarbamoylalkyl for $R_{19}$ may include N-phenylcarbamoylmethyl, N-phenylcarbamoylethyl, N-naphthylcarbamoylmethyl, N-naphthylcarbamoylethyl, and the like.

(14) With respect to the compound (XXII):

Suitable examples of "aryl substituted by at least one substituent of nitro and esterified carboxy" for $R_{21}$ may include p-nitrophenyl, 2,4-dinitrophenyl, 2-nitro-4-methoxycarbonyl phenyl and the like, and suitable examples of substituted aryl moiety in aryl amino whose aryl ring is substituted by at least one substituent of nitro and esterified carboxy for $R_{22}$ may be the same as illustrated for the definition for $R_{21}$.

(15) With respect to the compound (XXIV):

Suitable examples of mono- or di-alkylamino for $R_{23}$ may include mono-alkylamino such as methylamino, ethylamino, propylamino, isopropylamino, butylamino, etc. and dialkylamino such as dimethylamino, diethylamino, methyl-propylamino, etc., and the optional carbon atom of said mono- or di-alkylamino may be substituted by esterified carboxy such as alkoxycarbonyl (e.g., methoxycarbonyl, ethoxycarbonyl, etc.), and the like.

(16) With respect to the compound (XXV):

Suitable examples of nitroaryl for $R_{24}$ may include mono- or di-nitrophenyl, mono or dinitronaphthyl, and the like.

(17) With respect to the compound (XXVI):

Suitable examples of aminoaryl for $R_{25}$ may include mono or diaminophenyl, mono or diaminonaphthyl and the like.

(18) With respect to the compounds (XXVII) and (XXVIII):

Suitable examples of aryl for $R_{26}$ may include phenyl, tolyl and naphthyl and the like.

A suitable example of bivalent aliphatic hydrocarbon residue for "$A_2$" is the same as illustrated before in the definition for "$A_1$".

Suitable examples of halogen atom for $X_5$ may include bromine, chlorine and the like.

Suitable examples of alkoxy for $R_{27}$ may include methoxy, ethoxy, propoxy, tert-butoxy, etc., whose alkyl moiety may be substituted by suitable substituent such as carboxy, esterified carboxy and the like, for example, carboxymethoxy, methoxycarbonylmethoxy, tert-butoxycarbonylethoxy, etc.

Suitable examples of alkanoylamino for $R_{27}$ may include formamido, acetamido, propionamido, butyramido, etc.), whose alkyl moiety may be substituted by ammonio radical (e.g., N,N,N-trimethylammonio, N,N,N-triethylammonio or pyridinio, etc.) which bears an anion such as chloro, bromo, iodo, hydroxy, sulfoxy, methylsulfoxy, ethylsulfoxy, formyloxy or p-toluenesulfonyloxy, and the like.

(19) With respect to the compound (XXXII):

A suitable example of alkyl for $R_{32}$ and $R_{33}$ is the same as illustrated before for the alkyl for $R_{13}$.

(20) With respect to the compounds (XXXIII) and (XXXIV):

Suitable examples of acylamino in the definitions for $R_{38}$ is the same as illustrated before for the acylamino for $R_{36}$.

A suitable example of alkyl for $R_{39}$, $R_{40}$ and $R_{41}$ and alkyl moiety in alkoxy and substituted alkoxy for $R_{38}$ is the same as illustrated before for the alkyl for $R_{13}$.

Suitable examples of substituent in substituted alkoxy for $R_{38}$ is a conventional alkanoyl (e.g., acetyl, propionyl, butyryl, isobutyryl, pivaloyl, etc.), etc. as illustrated before for the protected group for Y.

Suitable examples of substituted-alkyl in the definitions for $R_{39}$ and $R_{41}$ may include acyloxyalkyl such as alkanoyloxyalkyl (e.g., acetoxymethyl, acetoxyethyl, acetoxypropyl, propionyloxymethyl, propionyloxyethyl, butyryloxymethyl, pivaloyloxymethyl, etc.) and haloalkyl such as monohaloalkyl (e.g., fluoromethyl, chloromethyl, bromomethyl, chloroethyl, bromoethyl, chloropropyl, bromopropyl, etc.), dihaloalkyl (e.g., dichloroethyl, 2,3-dichloropropyl, etc.) and trihaloalkyl (e.g., trichloromethyl, etc.), and the like.

(21) With respect to the compounds (XXXV) and (XXXVI):

Suitable aryl in the definition for $R_{42}$ may include aryl which may be substituted by suitable substituent such as carboxy, etc., the examples of which are phenyl, carboxyphenyl, tolyl, naphthyl and the like.

A suitable example of alkylene for "$A_3$" may include methylene, ethylene, propylene, etc.

(22) With respect to the compounds (XXXIX) and (XXXX):

Suitable examples of aryl substituted by at least one substituent of nitro and esterified carboxy for $R_{43}$ are the same as illustrated for the same group for $R_{21}$.

Suitable examples of aromatic heterocyclic group for $R_{43}$ may include the same as illustrated in the explanation of the heterocyclic group for $R_1$ of the compound (I), and the more particular examples thereof are pyridyl, pyridyl-1-oxide, pyrimidynyl, oxadiazolyl, etc., which may be substituted by an aryl such as phenyl, tolyl, naphthyl and the like.

(23) With respect to the compounds (XXXXI) and (XXXXII):

Suitable examples of aralkyl for $R_{44}$ are the same as illustrated for $R_{15}$.

Suitable examples of alkyl for $R_{45}$ and $R_{46}$ are the same as illustrated for $R_{13}$.

(24) With respect to the compounds (XXXXIII) and (XXXXIV):

Suitable examples of the derivative in "carboxy or its derivative" for $R_{47}$ are the same as illustrated before in the explanation for the derivative of the carboxy for $R^Z$.

Suitable examples of protected group in the protected amino for $R_{48}$ may include the same as illustrated in the explanation for Y.

(25) With respect to the compounds (XXXXV), (XXXXVI), (XXXXVII), (XXXXVIII), (XXXXIX), (XXXXII), (XXXXIII) and (XXXXIV):

Suitable examples of acyl moiety in the acylamino group in the definition for $R_{49}$, $R_{50}$, $R_{51}$, $R_{52}$, $R_{53}$, $R_{54}$, $R_{55}$ and $R_{56}$ may include the same ones as illustrated in the acylamino for $R_1$.

Suitable examples of the reactive derivative in "carboxy or its reactive derivative" moiety in the definition for $R_{49}$ are the same as illustrated in explanation of the derivative of the carboxy for $R^Z$, and there may be also exemplified aryl (e.g., phenyl, naphthyl, etc.) esters.

Suitable examples of "N-(hydroxyalkyl)carbamoyl" moiety in the definition for $R_{50}$ may include N-(hydroxymethyl)carbamoyl, N-(hydroxyethyl)carbamoyl, N-(hydroxypropyl)carbamoyl, etc.

Suitable examples of "N-aralkylcarbamoyl" moiety in the definition for $R_{50}$ may include N-benzylcarbamoyl, N-phenethylcarbamoyl, etc., in which aryl moiety may be substituted by suitable substituent(s).

Suitable examples of the esterified carboxy in "esterified carboxyalkylamino and esterified carboxyalkenylamino" moieties in the definition for $R_{52}$ and $R_{53}$ may include the same ones as illustrated in the explanation of ester in the derivative of the carboxy for $R^Z$, and suitable examples of alkylamino moiety therein are methylamino, ethylamino, propylamino and the like; and further suitable examples of alkenylamino moiety therein are vinylamino, propenylamino, 1-methylvinylamino, 2-propenylamino and the like, respectively.

Suitable examples of alkanoyl in the definition for $R_{55}$ and aroyl moiety in the definition for $R_{55}$ may include the same ones as those illustrated in the explanation of an acyl moiety in the acylamino for $R_1$, respectively.

Suitable examples of alkyl moiety in the definition for $R_{56}$ is the same as illustrated for $R_{13}$.

Suitable examples of α-hydroxy aralkyl moiety in the definition for $R_{56}$ may include α-hydroxybenzyl, 1-hydroxy-1-(1-naphthyl)methyl, etc.

(26) With respect to the compound (XXXXXVI):
Suitable examples of aralkyl moiety in aralkylamino for $R_{57}$ may include the same as illustrated for $R_{15}$.

(27) With respect to the compounds (XXXXXVI) and (XXXXXVII):
Suitable examples of halogen for $X_6$ may include the same as illustrated in the definition for $X_2$.

Suitable examples of alkyl for $R_{58}$, $R_{59}$ and $R_{60}$ are the same as illustrated for $R_{13}$.

(28) With respect to the compound (XXXXXI):
Suitable examples of aralkanoyl moiety in aralkanoylamino for $R_{61}$ may include the same as illustrated in the explanation of the acyl moiety in the acylamino for $R_1$.

(29) With respect to compounds (XXXXXII) and (XXXXXIII):
Suitable examples of aryl in the definition for $R_{62}$ may include the same ones as illustrated for $R_{15}$, and suitable examples of alkylene for $A_5$ may include the same ones as illustrated for $A_3$.

(30) With respect to compounds (XXXXXIV) and (XXXXXV):
Suitable examples of aryl and heterocyclic group for $R_{63}$ may include the same examples as those illustrated for $R_{15}$, respectively.

Suitable examples of aroyl moiety and aroyl for $R_{66}$, $R_{67}$ and $R_{68}$ may include benzoyl, toluoyl, xyloyl and the like, and suitable examples of aralkoxy for the same may include benzyloxy, phenethyloxy, phenylpropionyloxy, tolylmethoxy, diphenylmethoxy, trityloxy and the like.

(31) With respect to the compound (XXXXXVII):
Suitable examples of aralkyl for $R_{69}$ may include the same examples as illustrated for $R_{15}$.

(32) With respect to the compound (XXXXXVIII):

Suitable examples of alkyl for $R_{70}$ may include the same examples as illustrated for $R_{13}$, and suitable examples of heterocyclic moiety in the definition for $R_{70}$ may include the same examples as illustrated for $R_{15}$.

(33) With respect to the compounds (XXXXXX) and (XXXXXXI):
Suitable examples of esterified carboxy moiety in the definition for $R_{71}$ may include the same examples as illustrated in the explanation of ester in the derivative of the carboxy for $R^Z$, and suitable ones of alkyl moiety for $R_{71}$ may include the same examples as illustrated for $R_{13}$.

(34) With respect to the compounds (XXXXXXII) and (XXXXXXIII):
Suitable examples of aryl for $R_{72}$ may include the same examples as illustrated for $R_{15}$, and suitable ones of alkyl for $R_{72}$ may include the same examples as illustrated for $R_{13}$, and further suitable ones of esterified carboxy moiety in the definition for $R_{73}$ may include the same ones as illustrated in the explanation of ester in the derivative of the carboxy for $R^Z$.

(35) With respect to the compounds (XXXXXXIV), (XXXXXXV), (XXXXXXVI) and (XXXXXXVII):
Suitable examples of alkyl, alkenyl and aryl for $A''$ and $R_{74}$ may include the same examples as those of illustrated in the alkyl for $R_{13}$, in the alkenyl for $R_1$, and in the aryl for $R_{15}$, respectively.

(36) With respect to the compound (XXXXXXVIII):
Suitable examples of lower alkyl for $R_{75}$ may include methyl, ethyl, propyl and the like.

(37) With respect to the compound (XXXXXXIX):
Suitable examples of alkoxy for $R_{76}$ may include methoxy, ethoxy, propoxy, butoxy and the like, and suitable ones of aralkyl moiety in aralkoxy for $R_{76}$ may include the same examples as illustrated for $R_{15}$.

Suitable examples of alkyl, acyl and aralkyl for $R_{80}$ may include the same examples as those illustrated for $R_{13}$, respectively.

(38) With respect to the compound (XXXXXXX):
Suitable examples of aralkyl for $R_{77}$ may include the same examples as illustrated for $R_{15}$.

(39) With respect to the compounds (XXXXXXXI) and (XXXXXXXII):
Suitable examples of the protecting group on amino group for $R_{78}$ may include the same examples as illustrated for Y, and suitable ones of acyl for $R_{79}$ may include the same examples as ones of acyl moiety in the acylamino for $R_2$.

(40) With respect to the compounds (XXXXXXXIX), (XXXXXXXX), (XXXXXXXXI), (XXXXXXXXII) and (XXXXXXXXIII):
Suitable examples lower alkyl for $R^g$, and alkyl moiety in lower alkoxycarbonyl for $R^f$ and $R^f$ may include methyl, ethyl, propyl, tert-buthyl and the like.

As previously mentioned, the compounds produced by the processes according to this invention are new. Particularly, the compounds represented by the following formula are preferred compounds of the present invention.

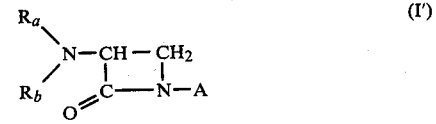

in which
(1) $R_a$ and $R_b$ are each hydrogen;

(2) $R_a$ is hydrogen and $R_b$ is arenesulfonyl,
(3) $R_a$ and $R_b$ together form a imido group derived from a dicarboxylic acid; or
(4) $R_a$ is hydrogen and $R_b$ is an acyl group selected from the following groups:

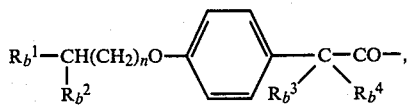 (i)

wherein
n is an integer 0–4
$R_b{}^1$ is hydrogen: or carboxy
$R_b{}^2$ is hydroxy; halogen; azido; amino; mo- or dialkylamino; alkenylamino; cycloalkylamino; arylamino; aralkylamino; alkanoylamino; alkoxy(thiocarbonyl)amino; alkoxycarbonylamino; aryloxyalkanoylamino; aralkanoylamino; heterocyclic alkanoylamino; aroylamino; N'-arylureido; N'-arylthioureido; or arylthio;
$R_b{}^3$ is hydrogen; hydroxy; amino; arylamino; alkanoylamino; alkoxy(thiocarbonyl)amino; alkoxycarbonylamino; aroylamino; aralkanoylamino; N'-arylureido; or N'-arylthioureido;
$R_b{}^4$ is hydrogen, or
$R_b{}^3$ and $R_b{}^4$ together form oxo; hydroxyimino; alkoxyimino; or alkanoyloxyimino;
in which the alkane or alkene moiety may be substituted by at least one suitable substituent of carboxy, halogen, sulfo, and the aryl and heterocyclic ring may be substituted by at least one suitable substituent of nitro, halogen or carboxy;

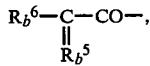 (ii)

wherein
$R_b{}^5$ is oxo hydroxyimino; alkoxyimino; aralkoxyimino; or aroyloxyimino;
$R_b{}^6$ is cyano; alkyl; aryl; heterocyclic radical; alkylamino; aralkylamino; aralkoxyaryl; alkenyloxyaryl; or alkoxyaryl;
in which the alkane moiety may be substituted by at least one suitable substituent such as hydroxy or carboxy;
(iii) $R_b{}^7$—CO—,
wherein
$R_b{}^7$ is hydrogen; aryl; alkoxyaryl; aryloxy; alkenyl; (arylaminoalkylaryloxy)alkyl; alkylthioalkenyl; aralkyloxy; aralkenyl; arylamino; alkyl-and(or)aryl-substituted heterocyclic radical; aryloxyalkanamido; heterocyclic-amino; guanidino; or 3-aralkanoylguanidino;
in which each of aryl and heterocyclic rings may have at least one suitable substituent such as nitro, halogen, oxo or amino;

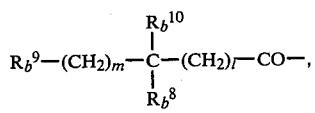 (iv)

wherein
m and l are each an integer of 0–4, $R_b{}^8$ is hydrogen; alkyl; aryl; aryloxy; heterocyclic radical; N-arylcarbamoyl; or N-(aralkanamidoalkyl)carbamoyl;
in which each of aryl and heterocyclic rings may be substituted by hydroxy;
$R_b{}^9$ is hydrogen; amino; azido; halogen; hydroxy; carboxy; sulfo; or arenesulfonyloxy; alkyl; or alkenyl
in which alkyl and alkenyl may have at least one substituent selected from amino, azido, halogen, hydroxy, carboxy, sulfo, aroyl, substituted or unsubstituted aryl and substituted or unsubstituted heterocyclic radical; aryl
which may have at least one substituent selected from hydroxy, nitro, carboxy, halogen, alkanoyl, arenesulfonamido and carboxy- or hydroxy-substituted arenesulfonamido; heterocyclic radical; alkylheterocyclic radical; aryl- and oxo-substituted heterocyclic radical; aralkoxy- and oxo-substituted heterocyclic radical; biheterocyclic radical; (heterocyclicalkanamido)heterocyclic radical; oxo-aralkanamidoheterocyclic radical; aroyl; heterocyclicalkanoyl which may be substituted by alkyl, halogen, heterocyclic group, amino, aryl or haloaryl; alkoxy; cycloalkoxy;
aryloxy whose aryl ring may have at least one substituent selected from nitro, halogen, alkanoyl, alkanoylamino, aryl, halo- and nitroaryloxy, aralkylamino, alkyl and alkenyl, alkyl and alkenyl may be further substituted by at least one substituent selected from carboxy, amino, hydroxy, nitro, hydroxyimino, alkoxyimino, carboxyalkoxyimino, (N-halo-N,N,N-trialkylammonioalkanoyl)hydrazono, alkylthioalkanamido of which alkyl moiety may be substituted by at least one substituent of amino and carboxy; aralkylaminoalkyl which may be substituted by esterified carboxy or carboxyalkoxy; heterocyclicoxy;
alkylthio, alkenylthio, aryloxyalkananidoalkylthio, aroylalkylthio and N-arylcarbamoylalkylthio, of which arene moieties may have at least one substituent of halogen, nitro, amino and carboxy;
alkanesulfinyl; N-arylcarbamoylalkanesulfinyl;
carboxyarylthio; heterocyclicthio which may have hydroxy; aminoalkylheterocyclicthio; (alkanamidoalkyl)heterocyclic thio, of which heterocyclic moiety may have hydroxy;
substituted or unsubstituted arylamino;
heterocyclicamino which may have at least one substituent selected from oxo and aryl;
aralkylamino; imino substituted or unsubstituted-N-aralkylamino; N-alkyl-N-aralkylamino; alkylamino; N-aryl-alkanamido; N-alkyl-N-arylamino in which alkyl moiety may have at least one substituent of azido and carboxy; N-alkanesulfonyl-N-arylamino;
alkanamido of which alkane moiety may be substituted by at least one substituent of halogen, amino and azido; substituted or unsubstituted cycloalkoxyalkanoylamino; alkylthioalkanamido, in which alkyl moiety may be substituted by at least one substituent of amino, halogen and carboxy;
aralkanamido; alkoxyaralkanamido or aryloxyaralkanamido, in which alkane moiety and aryl ring may have at least one substituent of halogen, aralkoxyimino, arylamino, amino, and hydroxy;
arylaminoalkanamido, in which aryl ring and alkane moiety may be substituted by at least one substituent of halogen, carboxy, nitro and amino;

(N-arenesulfonylarylamino)alkanamido; aryloxyalkanamido, which may be substituted by at least one substituent of halogen, nitro, carboxy, formyl and carbazoyl;

alkylaryloxyalkanamido, which may be substituted by hydroxy; arylaryloxyalkanamido, which may be substituted by at least one substituent of halogen and nitro;

aralkylaryloxyalkanamido, which may be substituted by at least one substituent of hydroxyimino and halogen; aralkylaminoalkylaryloxyalkanamido, which may be substituted by at least one substituent of carboxymethoxy and carboxy derivative; alkanoyl-aryloxyalkanoylamino;

aroylaryloxyalkanamido, which may be substituted by at least one substituent of nitro, amino and halogen; (alkylthioalkanamidoaroyl)aryloxyalkanamido, which may be substituted by at least one substituent of halogen, amino and carboxy; (alkylthioalkylaminoaroyl)aryloxyalkanamido, which may be substituted by at least one substituent of amino and halogen; (alkanamidoaroyl)aryloxyalkanamido, which may be substituted by halogen; [(N-halo-N,N,N-trialkylammonio)alkanamidoaroyl]aryloxyalkanamido, which may be substituted by halogen; heterocycliccarbonylaryloxyalkanamido, which may be substituted by halogen;

aralkylaminoalkylaryloxyalkanamido, which may be substituted by at least one substituent of alkoxy, carboxy-alkoxy or carboxy;

(heterocyclicthioalkanamidoaroyl)aryloxyalkanamido; heterocyclicaryloxyalkanamido, in which heterocyclic ring may be substituted by at least one substituent of alkyl, aryl, haloaryl, halogen and amino;

(diaryloxy)alkanamido, which may be substituted by at least one substituent of halogen, amino and nitro;

arylthioalkanamido, which may be substituted by carboxy;

heterocyclicalkanamido;
bi-heterocyclicalkanamido;
heterocyclicthioalkanamido, which may be substituted by at least one substituent of hydroxy, amino, alkyl and aminoalkyl;

(aralkanamido)alkanamido, which alkane moiety and/or aryl ring may be substituted by at least one substituent of amino, halogen and carboxy;

arenesulfinylalkanamido, which may be substituted by carboxy;

arenesulfonyloxyalkanamido;
(N-aryl-N-arenesulfonamido)alkanamido;
heterocycliccarbonylamino, which may be substituted by halo-substituted aryl;
arylglyoxyloxylamino;
alkoxyalkylmino
N'-aralkyloxamoylamino; N'-aryloxamoylamino, which may be substituted by nitro;
N'-arylureido; guanidinocarbonylamino;
arenesulfonamido or alkane sulfonamido, which may have at least one suitable substituent of hydroxy, carboxy and halogen;
N'-aroylureido;
(N-aryloxyalkanoyl)aminooxy, (N-alkyliden)aminooxy, (N-heterocyclicalkylidene)aminooxy or (N-aralkylidene)aminooxy, which may have at least one substituent of carboxy and alkoxy;

$R_b{}^{10}$ is hydrogen or alkyl; and A is hydrogen or a group represented by the formula;

in which $R^X$, $R^Y$ and $R^Z$ are the same as defined in the definition for the compound (I), with a proviso as stipulated above in the definition of the compound (I).

With respect to the above definition for the preferred compound (I'), the following points are to be understood.

The carboxy, amino and hydroxy group as defined in the definition of the compound (I') include the corresponding equivalents, respectively.

As the equivalents of the carboxy, there may be the derivative of carboxy, the detail of which is explained hereinabove in the explanation of the definition for the compound (I) and suitable examples of which are the same as those illustrated in the explanation of the derivative of the carboxy for "$R^Z$" of the compound (I).

As the equivalents of the amino and hydroxy, there may be the protected amino and protected hydroxy, respectively. Suitable protective group of amino and protective group of hydroxy are the same as those illustrated in the explanation of the protective group for Y of the compound (IV).

It is to be noted the derivative of carboxy, the protected amino and the protected hydroxy are to be included within the scope of the compound as equivalets of the carboxy, the amino and the hydroxy in the definition of compound (I'), respectively.

With respect to various definitions for $R_b{}^2$, $R_b{}^3$, $R_b{}^4$, $R_b{}^5$, $R_b{}^6$, $R_b{}^7$, $R_b{}^8$, $R_b{}^9$ and $R_b{}^{10}$:

Suitable examples of halogen moiety may include the same examples as illustrated for $X_2$;

Suitable ones of alkyl or alkane moieties may include the same examples as illustrated in the explanation for A;

Suitable ones of dialkyl may include dimethyl, diethyl, dipropyl and the like;

Suitable ones of alkenyl or alkene moiety may include the same examples as illustrated in the explanation for $R_1$;

Suitable ones of cycloalkyl may include the same examples as illustrated in the explanation for $R_1$;

Suitable ones of aryl or arene moieties may include the same examples as illustrated for $R_{15}$;

Suitable ones of aralkyl or aralkane moieties may include the same examples as illustrated for $R_{17}$;

Suitable ones of alkanoyl may include the same examples as illustrated for $R_2$;

Suitable ones of alkoxy may include the same examples as illustrated for $R_{27}$;

Suitable ones of aralkoxy may include the same examples as illustrated for A;

Suitable ones of aralkanoyl may include the same examples as illustrated for $R_{14}$;

Suitable ones of aroyl may include the same examples as illustrated for $R_2$;

Suitable ones of t-alkyl may include t-butyl, t-pentyl, t-hexyl and the like; and Suitable ones of heterocyclic group or heterocyclic moieties may include the same examples as illustrated in the explanation for $R_1$.

The processes of this invention are explained in details hereinafter.

In this invention, as key starting compounds, there are employed FR-1923 substance, 3-amino-1-(α-carboxy-4-hydroxybenzyl)-2-azetidinone (a), 1-substituted-3-amino-2-azetidinone (b) and 3-amino-2-azetidinone (c).

Such starting compounds can be prepared, for example, by processes as shown in the following scheme.

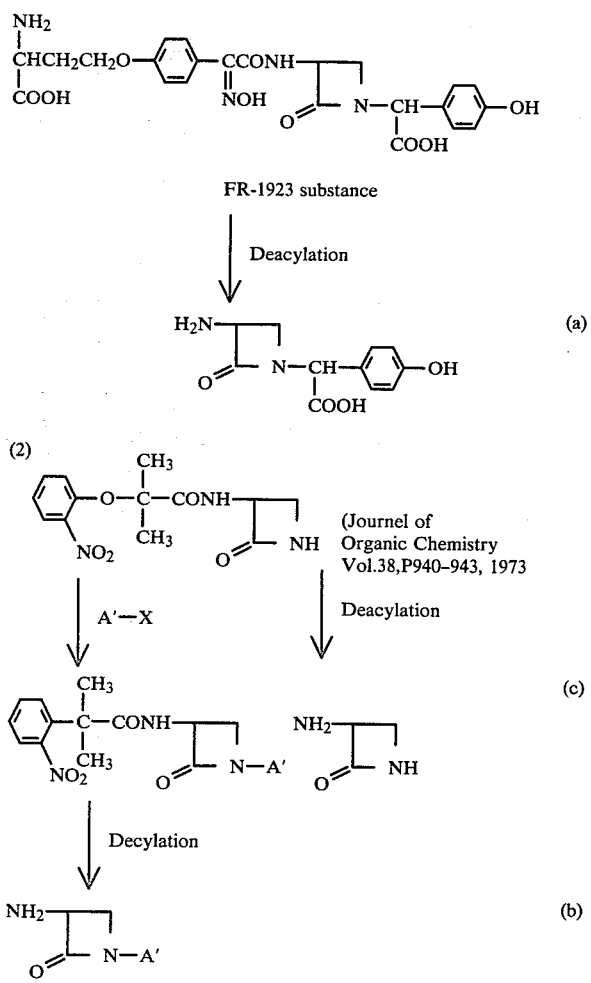

wherein X is an acid residue and A' is as defined above.

(1) Process 1: (II)→(I)

In this process, the object compound (I) can be prepared by reacting the compound (II) or its reactive derivative at the amino with an acylating agent.

As acylating agents to be used in the present reaction, there may be exemplified an organic carboxylic acid, an organic sulfonic acid and the corresponding thio-, or imido-acid, and more particularly, an aliphatic acid, an aromatic or heterocyclic carboxylic acid, and the corresponding sulfonic acid, carbamic acid, carbonic acid and thio-acid, and their reactive derivative.

As the reactive derivatives, there may be exemplified an acid anhydride, an activated amide, an activated ester, an isocyanate and an isothiocyanate, etc.

Examples of such reactive derivatives are illustrated by an acid azide;

an mixed acid anhydride with an acid such as dialkylphosphoric acid, phenylphosphoric acid; diphenylphosphoric acid, dibenzylphosphoric acid, halogenated phosphoric acid, dialkylphosphorous acid, sulfurous acid, thiosulfuric acid, hydrohalogenic acid (e.g., hydrochloric acid, hydrobromic acid, etc.), sulfuric acid, monoalkyl carbonic acid, aliphatic carboxylic acid (e.g., acetic acid, pivalic acid, pentanoic acid, isopentanoic acid, 2-ethylbutyric acid or trichloroacetic acid), aromatic carboxylic acid (e.g., benzoic acid), or symmetrical acid anhydride;

an acid amide with pyrazole, imidazole, 4-substituted imidazole, dimethylpyrazole, triazole or tetrazole; and an ester (e.g., cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or ester with N,N-dimethylhydroxylamine, 1-hydroxy-2-(1H)-pyridone, N-hydroxysuccinimide or N-hydroxyphthalimide) and the like.

The above reactive derivatives are selected according to the kind of the acid to be used. In the reaction, when free acid is used as an acylating agent, the reaction may be preferably conducted in the presence of a condensing agent such as N,N-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonyldi-(2-methylimidazole), pentamethyleneketene-N-cyclohexylimide, diphenylketene-N-cyclohexylimine, alkoxyacetylene, 1-alkoxyl-1-chloroethylene, trialkyl phosphite, ethyl polyphosphate, isopropyl polyphosphate, phosphorus oxychloride, phosphorus trichloride, thionylchloride, oxalyl chloride, triphenylphosphine, 2-ethyl-7-hydroxybenzisoxazolium salt, 2-ethyl-5-(m-sulfophenyl)isoxazolium hydroxide(chloromethylene)-dimethylammonium chloride, 2,2,4,4,6,6-hexachloro-2,2,4,4,6,6-hexahydro-1,3,5,2,4,6-triazatriphosphorine, or a mixed condensing agent such as triphenylphosphine and a carbon tetrahalide (e.g., carbon tetrachloride, carbon tetrabromide, etc.) and the like.

The example of an acyl group to be introduced into the amino group in the compound (I) by the above acylating agent may be a dehydroxylated group of an aliphatic, aromatic and heterocyclic carboxylic acid, and the corresponding sulfonic acid, carbonic acid, carbamic acid and thio acid, etc., and more particular acyl group may be the same acyl group as illustrated in the explanation of the acyl group in the acylamino group for $R_1$.

As the reactive derivative at the amino at the 3rd position of the compound (II), there may be exemplified shiff's base, salt with acid (e.g. hydrochloric acid) and the conventional reactive derivative.

The acylation in the present process is conducted in a conventional manner known skilled in the art, for example, the acylation of 6-aminopenicillanic acid or 7-aminocephalosporanic acid to provide the corresponding 6-acylamino penicillin or 7-acylaminocephalosporin compounds.

That is, the present reaction is conducted by reacting the compound (II) or its reactive derivative at the amino with an acylating agent usually in a solvent which does not give bad influence to the reaction, for example, water, acetone, dioxane, acetonitrile, chloroform, methylene chloride, dichloroethane, tetrahydrofuran, ethyl acetate, dimethylformamide, pyridine, etc., and the hydrophilic solvent as mentioned above can be used in a mixture with water.

The present reaction can also be carried out in the presence of a base such as inorganic base (e.g., alkali metal bicarbonate, etc.) and an organic base such as trialkylamine (e.g., trimethylamine, triethylamine, tributylamine, etc.), N-methylmorpholine, N-methylpiperidine, N,N-dialkylaniline (e.g., N,N-dimethylaniline, N,N-diethylaniline, etc.), N,N-dialkylbenzylamine (e.g., N,N-diethylbenzylamine, etc.), pyridine, picoline, lutidine, 1,5-diazabicyclo[4,3,0]non-5-ene, 1,4-diazabicyclo[2,2,2]octane, 1,8-diazabicyclo[5,4,0]undecene-7, etc.

In the present reaction, a liquid base or liquid condensing agent also can be used as a solvent for the reaction.

There is no particular limitation to the present reaction temperature, and the present reaction can be preferrably carried out under cooling or at ambient temperature.

(2) Process 2: (III)→(I'')

In this process, the object compound (I'') can be prepared by reacting the compound (III) with a reagent of the formula: A'—X' wherein A' is as defined above and X' is an acid residue.

In the reagent of the formula: A'—X', examples of the definitions for A' are the same as illustrated in the explanation of the definitions for A excepting hydrogen. As examples of the acid residue for X', there may be exemplified an acid residue of an inorganic acid (e.g. hydrochloric acid, hydrobronic acid, hydroiodic acid, sulfuric acid, etc.); an acid residue of an organic acid such as organic sulfate (e.g. methyl sulfate, ethyl sulfate, etc.), organic sulfonic acid (e.g. methane sulfonic acid, benzene sulfonic acid, toluene sulfonic acid, etc.) and organic carbamic acid (e.g. dimethylcarbamic acid, diethylcarbamic acid, etc.) and the like.

The reaction is usually conducted in a solvent. Suitable examples of the solvents are water, acetone, dioxane, acetonitrile, methylene chloride, chloroform, dichloroethane, tetrahydrofuran, ethyl acetate, dimethylformamide, pydridine, etc., among which hydrophilic solvent can be used in a mixture with water. Any other solvent which does not give bad influence to the reaction also may be used.

There is no particular limitation to the reaction temperature, and the reaction is usually conducted at ambient temperature or under cooling.

In case that the compound (I'') thus produced has the derivative of carboxy or the protected carboxy as substituent, the compound (I'') may be subjected to elimination reaction, whereby said derivative of carboxy or protective group is transformed into the corresponding carboxy group, whose reaction is also included within the scope of the present invention.

The elimination reaction is conducted by a conventional method, that is substantially the same methods as those explained in the elimination reaction for the hereinafter mentioned Process 3, e.g. solvolysis, reduction, etc.

(3) Process 3: (I')→(II)

In this process, the object compound (II) can be prepared by eliminating the acyl group of compound (I') in a conventional manner.

A suitable method to be used in the elimination reaction of the acyl moiety in acylamino may include solvolysis such as hydrolysis using an acid or a base; aminolysis; reduction such as chemical reduction or catalytic reduction; and combined method comprising iminohalogenation, imino-etherification and solvolysis.

In the above reaction, suitable examples of reagents to be used are as follows.

For solvolysis:

Solvolysis is preferably conducted in the presence of an acid or base.

Suitable acids are an inorganic acid (e.g. hydrochloric acid, sulfuric acid, etc.), an organic acid (e.g., formic acid, acetic acid, trifluoroacetic acid, propionic acid, benzenesulfonic acid, p-toluenesulfonic acid, etc.), an acidic ion exchange resin and the like.

Suitable bases are an inorganic base such as a hydroxide, carbonate or bicarbonate or an alkali metal (e.g., sodium, potassium, etc.), an alkaline earth metal (e.g., magnesium, calcium, etc.), and the like, an organic base such as an alkoxide of the above metal, a tertiary amine such as trialkylamine (e.g., trimethylamine, triethylamine, etc.), a disubstituted arylamine (e.g., N,N-dimethylamine, etc.) or a heterocyclic amine (e.g., N-methylmorpholine, N-methylpiperidine, N,N-dimethylpiperazine, pyridine, etc.), a basic ion exchange resin and the like.

For reduction:

Reduction is conducted with a conventional chemical reducing agent or by conventional catalytic reduction.

Suitable reducing agents are a metal (e.g., tin, zinc, iron, etc.) or a combination of metalic compound (e.g., chromium chloride, chromium acetate, etc.) and an organic or an inorganic acid (e.g., acetic acid, propionic acid, hydrochloric acid, etc.).

Suitable catalysts used in catalytic reduction are conventional ones such as platinum catalysts (e.g., platinum plate, spongy platinum, platinum black, colloidal platinum, platinum oxide or platinum wire), palladium catalysts (e.g., spongy palladium, palladium black, palladium oxide, palladium on carbon, colloidal palladium, palladium on barium sulfate or palladium on barium carbonate), nickel catalysts (e.g., reduced nickel, nickel oxide or Raney nickel), cobalt catalysts (e.g., reduced cobalt or Raney cobalt), iron catalysts (e.g., reduced iron or Raney iron) copper catalysts (e.g., reduced copper, Raney copper or Ullman copper), or other conventional catalysts.

For aminolysis:

Aminolysis is conducted with a conventional amine.

Suitable examples of amine to be used in the aminolysis include substituted or unsubstituted primary amine such as methylamine, ethylamine, propylamine, isopropylamine, butylamine, N,N-dimethyl-1,3-proanediamine and the like, and hydrozine such as hydrazine, methylhydrazine, ethylhydrazine and the like.

For combine method:

Iminohalogenation, iminoetherification, and solvolysis are conducted with a conventional iminohalogenating agent and conventional iminoetherizing agent, and then by conventional solvolysis:

Suitable iminohalogenating agents are a phosphorus compound such as phosphorus trichloride, phosphorus pentachloride, phosphorus tribromide, phosphorus pentabromide, phosphorus oxychloride, and their reaction equivalents such as thionyl chloride, phosgen, etc.

Suitable iminoetherifying agents used in the reaction with the resultant product in the foregoing iminohalogenation of the acylamino compound (I') are an alcohol such as an alkanol (e.g., methanol, ethanol, propanol, isopropanol, butanol, tert-butanol, etc.) or the corresponding alkanol having alkoxy (e.g., methoxy, ethoxy, propoxy, isopropoxy, buthoxy, etc.) as substituent(s) at the alkyl moiety thereof, and an alkoxide of such metal as mentioned above (e.g., sodium alkoxide, potassium alkoxide, calcium alkoxide, barium alkoxide, etc.), each of which is derived from said alcohol. Thus obtained reaction product is, if necessary, solvolyzed in a conventional manner.

The elimination reactions, i.e. solvolysis, aminolysis reduction and combined method comprising iminohalogenation, iminoetherification and solvolysis are conventional ones employed for the elimination of acyl group in acylamino group of penicillin and cephalosporin compounds, and said reactions may be conducted in the similar conditions to that of the elimination reaction in the penicillin and cephalosporin cases.

For example, the iminohalogenation and iminoetherification reactions are preferably conducted at ambient temperature or under cooling, and the solvolysis proceeds simply pouring the reaction mixture to water or a mixture of a hydrophilic solvent such as alcohol (e.g. methanol, ethanol, etc.) and water, and if necessary, with addition of an acid or base as exemplified above thereto.

The object compound (II) prepared in the above elimination reaction is also used as a key intermediate for the compound (I) of the present invention. That is, the introduction fo an acyl group different from that of the compound (I') to 1-substituted-3-amino-2-azetizinone (II) can produce a new 1-substituted-3-acylamino-2-azetizinone (I) having different antimicrobial activity spectrum from that of the compound (I').

(4) Process 4: (IV)→(III)

The object compound (III) can be prepared by subjecting the compound (IV) to degradative elimination reaction.

Suitable methods to be used in this elimination reaction are a conventional solvolysis such as hydrolysis (e.g., an acidic or a basic hydrolysis.) and a reduction (e.g., chemical or catalytic, reduction.), which may be optionally selected depending on a kind of a starting compound (IV).

Solvolysis such as hydrolysis is conducted preferably in the presence of an acid or a base in a conventional manner, the examples of which are the same as those illustrated in the explanation of Process 3 and to be referred to them.

Suitable examples of reducing agents for chemical reduction and catalysts for catalytic reduction are also the same as those illustrated in the explanation of Process 3, and to be referred to them.

The degradative reduction is usually conducted by reducing the compound (IV) with a reducing agent in a solvent in a conventional manner. The reaction conditions, for example, the solvent to be used and the reaction temperature are selected in accordance with the reduction method used and/or the kind of the compounds (IV) and/or (III). Generally, in the catalytic reduction method, it is preferable to employ a solvent such as methanol, ethanol, propanol, isopropanol, ethyl acetate or the like. In the method using a combination of a metalic compound and an acid, said acid is generally used as a solvent, but if necessary, there is employed a solvent such as water, acetone and the like.

The reaction temperature is not especially limited, and the reaction is usually conducted under cooling, at ambient temperature or at an elevated temperature.

The object compound (III) as prepared above is also used as a key intermediate for the compound (I') of this invention.

(5) Process 5: (V)→(VI)

In this process, the object compound (VI) is prepared by hydrolyzing the compound (V) or its derivative at carboxy. Examples of the derivative of carboxy of the starting compound is the same as illustrated in the explanation of the derivative of the carboxy for "$R^Z$" of compound (I).

The hydrolysis is conducted in a conventional manner.

That is, a suitable method to be used in this hydrolysis is conducted in the presence of an acid or base, example of which is the same one as that illustrated in the hydrolysis in the explanation for Process 3.

Though there is no particular limitation to the reaction temperature, it may be suitably selected according to the hydrolyzing condition to be used in the reaction, and the reaction is preferably conducted at ambient temperature or at somewhat elevated temperature in accordance with the kind of the solvent and other reagent used.

(6) Process 6: (VII)→(VIII)

In this process, the object compound (VIII) can be prepared by reducing the compound (VII) or its derivative at carboxy.

Example of the derivative at carboxy of the starting compound (VII) are the same as those illustrated in the explanation of the derivative of carboxy for "$R^Z$" of the compound (I).

In this reduction, the reaction is conducted by a conventional method such as a catalytic reduction; a reduction using a combination of a metal such as iron, tin or zinc and an acid such as an inorganic acid (hydrochloric acid, sulfuric acid or the like) or an organic acid (acetic acid or the like); a combination of an alloy (e.g., sodium amalgam, aluminum amalgam, etc.) a metal (e.g., zinc, tin, iron, etc.), or a salt thereof (e.g., zinc chloride, stannous chloride, ferric or ferrous chloride, etc.) and water, an alkali solution or an alcohol (e.g., methanol, ethanol, propanol or butanol); a hydrazine compound (e.g., phenyl hydrazine or hydrazine); a combination of titanium chloride and hydrochloric acid; an alkali borohydride such as sodium borohydride, and potassium borohydride; diborane; or an electrolytic reduction.

Suitable examples of catalysts for the catalytic reduction are the same one as those illustrated in the explanation of the catalyst for Process 3.

The reaction conditions for this reduction, for example, the solvent to be used and the reaction temperature may optionally be selected in accordance with the reduction method to be used. In general, it is preferable to employ a solvent such as water, an alcohol as mentioned above, dioxane, acetonitrile, tetrahydrofuran, dimethylformamide, pyridine and the like, and further the acid as mentioned above may also be used as a solvent.

The reaction temperature is not particularly limited, and the reaction is usually conducted under cooling, at ambient temperature or at an elevated temperature.

(7) Process 7: (IX)→(X)

In this process, the object compound (X) can be prepared by reacting the compound (IX) or its derivative at carboxy with an acylating agent.

Example of the derivative at carboxy of the starting compound are the same as those illustrated in the explanation of the derivative of the carboxy for "$R^Z$" of the compound (I).

As acylating agents in the present reaction, there may be exemplified the same examples as those illustrated in the explanation of the acylating agents for Process 1.

The reaction conditions, for example, the solvent to be used and the reaction temperature are also substantially the same as those explained in the acylation for Process 1.

The present acylation may include, within its scope, the case that when the starting compound (IX) has group(s) of free hydroxy and hydroxyimino, it (they) is also occasionally acylated.

(8) Process 8: (XI)→(XII)

In this process, the object compound (XII) can be prepared by reacting the compound (XI) or its reactive derivative at carboxy with a nucleophile of the formula: $R_{11}$—H wherein $R_{11}$ is residue of nucleophile, or its salt.

The nucleophile of the formula: $R_{11}$—H wherein $R_{11}$ is as defined above to be used as a reagent may include an amine such as a primary and secondary amine, a thiol compound and a hydroxy compound, respectively.

Examples of the residue of nucleophile are aliphatic hydrocarbon amino (e.g. alkylamino, alkenylamino, etc.), di-aliphatic hydrocarbon amino (e.g. dialkylamino, etc.), aromatic amino (phenylamino, tolylamino, naphthylamino, etc.), heterocyclic amino (thienylamino, thiadiazolylthio, triazolthio, etc.), and aliphatic hydrocarbon substituted by such aromatic or heterocyclic group; and aliphatic hydrocarbon thio (or oxy), aromatic thio (or oxy), heterocyclic thio (or oxy), and aliphatic hydrocarbon thio (or oxy) substituted by such aromatic or heterocyclic group; in which aliphatic hydrocarbon moiety may be saturated or unsaturated and branched or partially cyclized, and such aliphatic hydrocarbon moiety, aromatic ring and heterocyclic ring may be substituted by at least one possible substituent.

Suitable examples of aliphatic hydrocarbon residue, aromatic group, a heterocyclic group, aliphatic hydrocarbon residue substituted by aromatic or heterocyclic group may include the same ones as illustrated in the explanation of the definitions for $R_1$.

More suitable examples of the residue of nucleophile are illustrated in the explanation for the compound (XII).

In the present process, there may be employed the nucleophile for above thiol or phenolic hydroxy compound in a form of a salt such as an alkali metal (e.g., sodium, potassium, etc.) salt and an alkaline earth metal (e.g., magnesium, calcium, etc.) salt. In the case that the thiol compound has a free amino as substituent, said amino substituted thiol compound may be employed in the form of the salt of amino with an acid such as are an inorganic acid (e.g., hydrochloric acid, hydrobromic acid, etc.) and an organic acid (formic acid, p-toluenesulfonic acid, etc.).

The reaction is usually conducted in a solvent. Suitable examples of the solvents include any solvent which does not give bad influence to the reaction, and are water, acetone, methanol, ethanol, tetrahydrofuran, dioxane, dimethylformamide, methylene chloride, chloroform, carbon tetrachloride, etc., in which a hydrophilic solvent may be employed in a mixture with water.

The present reaction is preferably conducted in the presence of a base such as an alkalimetal hydroxide (e.g., sodium hydroxide, potassium hydroxide, etc.), an alkaline earth metal hydroxide (e.g., magnesium hydroxide, calcium hydroxide, etc.), an alkali metal carbonate (e.g., sodium carbonate, etc.), an alkaline earth metal carbonate (e.g., calcium carbonate, etc.), an alkali metal alkoxide (e.g., sodium alkoxide, potassium alkoxide, etc.), an alkaline earth metal alkoxide (e.g., calcium alkoxide, barium alkoxide, etc.), an organic amine (e.g., trimethylamine, etc.), a basic ionexchange resin, etc.

There is no particular limitation to the present reaction temperature, and the reaction is usually carried out under cooling, at ambient temperature or at an elevated temperature.

(9) Process 9: (XIII)→(XIV)

In this process, the object compound (XIV) can be prepared by removing the protective group at the terminal amino, hydroxy and/or carboxy group in the acylamino group at the 3rd position of the compound (XIII) or its derivative at carboxy.

Examples of protective groups at the terminal amino, hydroxy and carboxy are the same as those illustrated in the explation of a protective group for the compound (IV), including the examples of ester of the carboxy group (i.e., esterified carboxy) as illustrated in the explanation of the derivative of the carboxy for $R^Z$ of the compound (I).

Suitable methods to be used in the present reaction are conventional ones, including a conventional solvolysis, a conventional reduction, a conventional method using a heavy metal and the like, which are selected depending on a kind of a starting compound (XIII).

A solvolysis and reduction may be conducted in substantially the same manner illustrated in the explanation of the degradative elimination process for Process 4.

Suitable examples of heavy metal in the method using a heavy metal are copper, zinc, etc.

Although there is no particular limitation to the reaction temperature and a preferable temperature are employed depending on a kind of the protecting group to be removed and the method to be used, the reaction is usually carried out under cooling, at ambient temperature or at somewhat elevated temperature.

By the present reaction, the protective group at the terminal amino, hydroxy and/or carboxy group in the acylamino group at the 3rd position of the starting compound (XIII) are removed to transform the corresponding amino, hydroxy and/or carboxy, respectively, and when the derivative at carboxy in the substituent at the 1st position of the starting compound (XIII) are the ester, said ester is also transformed into the corresponding carboxy, all these cases are also included within the scope of the present process.

(10) Process 10: (XV)→(XVI)

In this process, the object compound (XVI) can be prepared by reacting the compound (XV) or its derivative at carboxy with a halogenating agent.

Examples of the derivative at carboxy of the starting compound (XV) are the same as those illustrated in the explanation of the derivative of the carboxy for $R^Z$ of the compound (II).

Suitable examples of halogenating agents may include halogen such as chlorine bromine, etc.; hypohalogenous acid of its alkyl ester such as hypochlorous acid, tert-butylhypochlorite, etc., N-halamide such as N-bromoacetamide, N-iodoacetamide, N-bromosuccinamide, N-chlorosuccinimide, N-chlorophthalimide, etc.; a cuprous halogenide such as cuprous chloride, cuprous bromide, etc.; and, pyridinium hydrobromide, perbromide, dioxane dibromide, etc., and the like.

The reaction is usually carried out in an inert solvent.

A suitable solvent to be used in this reaction may include any solvent which have not adverse influence on the reaction, for example, water, methanol, ethanol, acetic acid, chloroform, methylene chloride, carbon tetrachloride, dioxane, acetonitrile, tetrahydrofuran, dimethylformamide and the like.

There is no particular limitation to the present reaction temperature, and the reaction is usually conducted under cooling, at amibient temperature or at somewhat elevated temperature.

(11) Process 11: (XVII)→(XVIII)

In this process, the object compound (XVIII) can be prepared by reacting the compound (XVII) or its derivative at carboxy with an acylating agent. The derivative at carboxy of the starting compound (XVII) are the same as those illustrated in the explanation of the derivative of carboxy for $R^Z$ of the compound (I).

Acylating agents to be used in the present reaction may include the same example as those illustrated in the explanation of the acylating agents for Process 1.

The acylation of the present process is conducted in a conventional manner, and the reaction conditions, for example, the solvent to be used and the reaction temperature are substantially the same as those explained in the acylation for Process 1.

(12) Process 12: (XIX)→(XX)

In this process, the object compound (XX) can be prepared by oxidizing the compound (XIX) or its derivative at carboxy.

The derivative at carboxy of the starting compound (XIX) are the same as those illustrated in the explanation of the derivative of the carboxy for $R^Z$ of the compound (I).

Oxidation in the present reaction is conducted in a conventional manner with a conventional oxidizing agent which can oxidize a —S— group into

group.

Suitable examples of such oxidizing agent are inorganic peracid or its salt (e.g., periodic acid, persulfuric acid, etc. or the sodium or potassium salt thereof); an organic peracid or its salt (e.g., perbenzoic acid, m-chloroperbenzoic acid, performic acid, peracetic acid, chloroperacetic acid, trifluoroperacetic acid, etc. or the sodium or potassium salt thereof etc.); ozone, hydrogen peroxide, urea-hydrogen peroxide and the like.

The present reaction is preferably conducted in the presence of a compound comprising a Group Vb or VIb metal in the Periodic Table, for example, tungstic acid, molybdic acid, vanadic acid, etc. or their salt with an alkali metal (e.g., sodium, potassium, etc.), an alkaline earth metal (e.g., calcium, magnesium, etc.) or ammonium, etc., or vanadium pentoxide.

The present oxidation is usually conducted in a solvent such as water, acetic acid, chloroform, methylene chloride, alcohol (e.g., methanol, ethanol, etc.), tetrahydrofuran, dioxane, dimethylformamide or any other solvent which does not give bad influence to the present reaction.

There is no particular limitation to the reaction temperature, and the present reaction is usually conducted at ambient temperature or under cooling.

(13) Process 13: (XXI)→(XXII)

In this process, the object compound (XXII) can be prepared by reacting the compound (XXI) or its derivative at carboxy with an aryl halide of the formula; R'-X', wherein R' is aryl substituted by at least one substituent nitro and esterified carboxy and X' is halogen.

The derivative at carboxy of the starting compound (XXI) is the same as those illustrated in the explanation of the derivative of the carboxy for $R^Z$ of the compound (I).

Suitable examples of aryl in the aryl substituted by at least one substituent of nitro and esterified carboxy for R' are the same as illustrated in the explanation of the definitions of $R_{21}$ and $R_{22}$ for the compound (XXII), and suitable examples of halogen are chlorine, bromine, etc. Further, examples of the ester in the esterified carboxy may include the same as those illustrated in the explanation of the ester in the reactive derivative of carboxy for $R^Z$ of the compound (I).

The present reaction is usually conducted in a solvent such as water, methanol, ethanol, propanol, tetrahydrofuran, dioxane, acetone, N,N-dimethylformamide, methylenechloride, chloroform, carbon tetrachloride or any other solvent which does not give bad influence to the present reaction.

The present reaction is preferably conducted in a base such as an inorganic or an organic base, for example, alkali metal hydroxide (e.g., sodium hydroxide, potassium hydroxide, etc.), an alkaline earth metal hydroxide (e.g., magnesium hydroxide, calcium hydroxide, etc.), an alkali metal carbonate (e.g., sodium carbonate, etc.), an alkaline earth metal carbonate (e.g., calcium carbonate, etc.), an alkali metal alkoxide (e.g., sodium alkoxide, potassium alkoxide, etc.), an alkaline metal alkoxide (e.g., calcium alkoxide, barium alkoxide, etc.), an organic amine (e.g., trimethylamine, etc.), a basic ionexchange resin, etc.

There is no particular limitation to the reaction temperature, and the present reaction is usually conducted under cooling, at ambient temperature or at an elevated temperature.

(14) Process 14: (XXIII)→(XXIV)

In this process, the object compound (XXIV) can be prepared by reacting the compound (XXIII) or its derivative at carboxy with a carbonyl compound of the formula

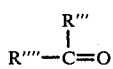

or its acetal or ketal, wherein R''' and R'''' are same or different hydrogen, alkyl, aryl or aralkyl, and then reducing the resulting product.

The derivative at carboxy of the starting compound (XXIII) are the same as those illustrated in the explanation of the derivative of the carboxy for $R^Z$ of the compound (I).

Examples of alkyl, aryl and aralkyl in the carbonyl compound, are methyl, ethyl, propyl, butyl, isobutyl, pentyl, etc. as alkyl; phenyl, tolyl, etc. as aryl; and benzyl, phenethyl, phenylpropyl, naphthylmethyl, etc. as aralkyl whose alkyl and the aryl moiety may be substituted at least one substituent of carboxy; alkoxy carbonyl, and halogen (chlorine, bromine, etc.).

Suitable examples of such carbonyl compound may include an aldehyde such as alkane aldehyde (e.g., formaldehyde, acetaldehyde, propionaldehyde, butylaldehyde, isobutylaldehyde, valeraldehyde, etc.), arene aldehyde (e.g., benzaldehyde, etc.) and aralkane aldehyde (e.g., benzaldehyde), and a ketone (e.g., acetone, methylethylketone, diethylketone, methylpropylketone, methylphenylketone, methyltolylketone, methylbenzylketone etc.).

The resulting product which is produced by reacting the compound (XXIII) or its derivative at carboxy with the carbonyl compound can be subjected to the following reduction with isolation or without isolation thereof.

In the following reaction, the reduction is conducted in a conventional manner including the substantially same methods and reaction condition (solvent, temperature, etc.) as illustrated in the explanation for the reduction in the Process 6.

The first step of this reaction is usually conducted in solvent which does not give bad influence to the reaction such as water, dioxane, methanol, ethanol, N,N-dimethylformamide or the like. A liquid carbonyl compound may also be used as a solvent.

There is no particular limitation to the reaction temperature, which is selected depending on a kind of the carbonyl compound to be used and the reducing agent to be used, and the reaction is usually conducted under cooling or at ambient or somewhat elevated temperature.

In the course of this reaction or post-treatment, the derivative at carboxy may be transformed into the corresponding carboxy, the functional group of

may be reduced to transform a group of

and a substituent, such as halogen may be replaced by hydrogen, in some occasion.

These cases as above are included within the scope of the present invention.

(15) Process 15: (XXV)→(XXVI)

In this process, the compound (XXVI) can be prepared by reducing the compound (XXV) or its derivative at carboxy.

Examples of the derivative at carboxy of the starting compound (XXV) are the same as those illustrated in the explanation of the derivative of the carboxy for $R^Z$ of the compound (I).

In this reaction, the reduction is conducted in a conventional manner, and examples of the reducing agents and the reduction conditions are substantially the same as illustrated in the explanation of the reduction for Process 6.

(16) Process 16: (XXVII)→(XXVIII)

In this process, the compound (XXVIII) can be prepaed by reacting the compound (XXVII) or its derivative at carboxy with an amine compound of the formula; $R_{27}-NH_2$ wherein $R_{27}$ is as defined above.

Examples of the derivative at carboxy of the starting compound (XXVII) may include same ones as illustrated in the explanation of the derivative of the carboxy for $R^Z$ of the compound (I).

Examples of alkoxy group and alkanoyl moiety of the alkanoylamino in the definitions for $R_{27}$ in the amine compound are the same as illustrated in the above explanation for the compound (XXVII).

In the reaction, the amine compound ($R_{27}-NH_2$) may be used in the form of its salt with an acid such as inorganic acid (e.g., hydrochloric acid, sulfuric acid, etc.) and organic acid (e.g. formic acid, acetic acid, etc.), and in this case the reaction may be preferably conducted under alkaline condition, for example, in the presence of alkali metal hydroxide (e.g., sodium hydroxide, potassium hydroxide), alkaline earth metal hydroxide (e.g., calcium hydroxide, etc.), and the like.

The reaction is usually conducted in solvent. Suitable examples of the solvent are water and a hydrophilic solvent such as methanol, ethanol, propanol, and N,N-dimethyl formamide, and any other solvent which does not give bad influence to the present reaction.

There is no particular limitation to the reaction temperature, and the present reaction is usually conducted under cooling at ambient temperature or at somewhat elevated temperature.

(17) Process 17: (XXIX)→(XXX)

In this process, the object compound (XXX) can be prepared by acylating the compound (XXIX) or its derivative at carboxy with an acylating agent.

Examples of the derivative at carboxy of the starting compound are the same as those illustrated in the explanation of the derivative of the carboxy for $R^Z$ of the compound (I).

Examples of acylating agent and acyl group in acylamino for $R_{29}$ may include the examples as those illustrated in the explanation for Process 1, respectively.

This process is conducted in a conventional manner, and may be conducted in substantially the same conditions (e.g., solvent, reaction temperature, etc.) as those mentioned in the explanation for Process 1.

(18) Process 18: (XXXI)→(XXXII)

In this process, the object compound (XXXII) can be prepared by reacting the compound (XXXI) or its derivative at carboxy with a hydroxyalkane sulfonic acid of the formula;

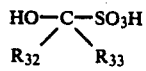

or the salt thereof, wherein $R_{32}$ and $R_{33}$ are each as defined above.

Examples of the derivative at carboxy of the starting compound (XXXI) are the same as those illustrated in the explanation of the derivative of the carboxy for $R^Z$ of the compound (I).

Examples of alkyl in the definitions of $R_{32}$ and $R_{33}$ for above hydroxyalkane sulfonic acid are the same as illustrated in the explanation for the compound (XXXII). As an example of the salts of said hydroxyalkane sulfonic acid, there may be illustrated salt with metal such as alkali metal (e.g., sodium, potassium, etc.), alkaline earth metal (e.g., calcium, magnesium, etc.) and the like.

The hydroxyalkanesulfonic acid can be prepared by reacting a carbonyl compound of the formula

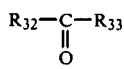

(wherein $R_{32}$ and $R_{33}$ are each as defined above) with sulfurous acid or the salt thereof (e.g. alkali or alkaline earth metal salt). Then, the object compound (XXXII) may be also prepared by reacting the compound (XXXI) with the above carbonyl compound and thereafter with the sulfurous acid or the salt thereof, the case of which is included within the scope of the present process.

The reaction is usually conducted in a solvent. As the suitable solvents, there may be illustrated water, hydrophilic solvent such as methanol, ethanol, propanol, tetrahydrofuran, dioxane, N,N-dimethylformamide, etc., and the mixture thereof, and any other solvent which does not give bad influence to the present reaction.

There is no particular limitation to the reaction temperature, and the present reaction is usually conducted under cooling, at ambient temperature or at an elevated temperature.

In the course of the reaction, amino group of the compound (XXXI) may occasionally react with the hydroxyalkanesulfonic acid or its above mentioned equivalent to be transformed into the corresponding mono- or di-substituted amino group

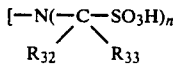

in which n is 1 or 2, or the salt thereof], these cases are also included within the scope of the present process.

When the hydroxyalkanesulfonic acid is used as a reagent, the reaction is preferably conducted in the presence of alkali or alkaline earth metal.

(19) Process 19: (XXXIII)→(XXXIV)

In this process, the compound (XXXIV) having esterified carboxy group (—$COOR_{39}$ and —$COOR_{41}$ wherein $R_{39}$ and $R_{41}$ are a group which is derived from an esterifying agent) can be prepared by reacting the compound (XXXIII) with a conventional esterifying agent.

Examples of esterified carboxy of the object compound may include the same as those illustrated in the explanation of the ester for the derivative of the carboxy for $R^Z$ of the compound (I) including silyl ester, aliphatic ester, ester containing aromatic or heterocyclic ring.

Esterifying agent may include any conventional agent which can esterify a carboxy group to provide an esterified carboxy group.

Suitable esterifying agents may include a halide compound such as alkyl halide (e.g., methyliodide, ethylbromide, ethyliodide, propylbromide, etc.), an alkenyl or alkynyl halide (e.g., allylbromide, methallylbromide, propargylbromide, etc.); substituted alkylhalide such as alkanoyloxy alkylhalide (e.g., acetoxymethylchloride, acetoxyethylchloride, acetoxypropylbromide, etc.), aroylalkylhalide (e.g., phenacylbromide, etc.), an aralkylhalide (e.g., benzylchloride, diphenylmethylchloride, phenethylchloride etc.) and the like;

a dialkyl sulfate (e.g., dimethyl sulfate, diethyl sulfate, dipropyl sulfate, etc.);

an alkyl sulfonate (e.g., methyl benzenesulfonate, methyl p-toluenesulfonate, ethyl 4-bromobenzenesulfonate, etc.);

a holoformate such as alkyl haloformate (e.g., methyl chloroformate, ethyl chloroformate, propyl chloroformate, etc.), alkenyl or alkynyl haloformate (e.g., allyl chloroformate, propynyl chloroformate, etc.);

a diazoalkane (e.g., diazomethane, diazoethane, etc.) and;

a hydroxy compound such as alcohol, for example, an alkanol (e.g., methanol, ethanol, propanol, 2-chloroethanol, 2,2,2-trichloroethanol, butanol, 1-cyclopropylethanol, etc.), a cycloalkanol (e.g., cyclopropanol, cyclopentanol, cyclohexanol, borneol, adamantanol, etc.) and an aralkanol (e.g., benzylalcohol, diphenylmethanol, phenethylalcohol, etc.); and the like.

In case that the hydroxy compound is used as a esterifying agent in this process, the reaction may be preferably conducted in the presence of a condensing agent such as those illustrated for the condensing agent in the Process 1.

In the course of the present reaction, the hydroxy group of the starting compound (XXXIII) may occasionally reacted with the esterifying agent to form a ether group, for example, alkoxy, aralkoxy, etc. Such cases as mentioned above are included within the scope of the present process.

The reaction is usually conducted in a solvent such as water, dioxane, acetone, pyridene, N-N-dimethylformamide, ether, and the like.

There is no particular limitation to the reaction temperature, and the reaction is usually conducted under cooling at ambient temperature or an elevated temperature.

(20) Process 20: (XXXV)→(XXXVI)

In this process, the object compound (XXXVI) can be prepared by oxidizing the compound (XXXV) or its derivative at carboxy. Examples of the derivative at carboxy of the starting compound (XXXV) are the same as those illustrated in the explanation of the derivative of the carboxy for $R^Z$ of the compound (I).

The present oxidation are conducted in a conventional manner.

Examples of the oxidizing agents are the same as those illustrated in Process 12 and the reaction is also conducted under substantially the same conditions (e.g. solvent, reaction temperature, etc.) as mentioned in the explanation of Process 12.

(21) Process 21: (XXXVII)→(XXXVIII)

In this process, the object compound (XXXVIII) can be prepared by reacting the compound (XXXVII) or its derivative at carboxy with a diazotizating agent and then solvolyzing the resulting diazonium salt.

The examples of derivative at carboxy of the starting compound (XXXVII) are the same as those illustrated in the explanation of the derivative of the carboxy for $R^z$ of the compound (I).

Suitable examples of diazotizating agent may include dinitrogen trioxide; nitrous acid or its derivative such as alkyl ester (e.g., methyl nitrite, ethyl nitrite, amyl nitrite, etc.), alkali metal salt (e.g., sodium nitrite, potassium nitrite, etc.); and mixed anhydride (e.g., nitrosyl chloride, nitrosyl bromide, notrisylsulfuric acid, nitrosylacetic acid, etc.).

The diazatization is usually conducted in a solvent such as water, methanol, ethanol, acetic acid, formic acid, N,N-dimethylformamide, dimethylsulfoxide or any other solvent which does not give bad influence to the reaction.

The resulting diazonium salt which is produced from the compound (XXXVII) or its derivative at carboxy by above reaction is then preferably solvolyzed by treating the reaction mixture per se or the isolated diazonium salt under acidic condition in the presence of an acid such as an inorganic acid (e.g., hydrochloric acid, sulfuric acid, phosphoric acid, nitric acid, etc.) and an organic acid (e.g., formic acid, acetic acid, propionic acid, butiric acid, p-toluenesulfonic acid, etc.).

There is no particular limitation to the present reaction temperature and the reaction is usually carried out under cooling, at ambient temperature, or at an elevated temperature.

In the present reaction, the amino group in the starting compound (XXXVII) is first diazotized and then solvolyzed to the corresponding hydroxy group. Then, depending upon a kind of the diazotizating agent and or the reaction condition to be used, the object compound (XXXVIII) or its derivative at carboxy can be prepared from the compound (XXXVII) or its derivative at carboxy by one-batch process such as by diazotization of the compound (XXXVII) under acidic condition, i.e. in an acidic solvent selected from a liquid inorganic or organic acid as stated above and a mixture of the inorganic or organic acid and the solvent as mentioned above, whereby the object compound (XXXVIII) are obtained without any specific solvolysis treatment.

(22) Process 22: (XXXIX)→(XXXX)

In this process, the object compound (XXXX) can be prepared by reacting the compound (XXXIX) or its derivative at carboxy with an aryl halide of the formula; R″X′ wherein R″ is aryl which may be substituted by at least one substituent of nitro, esterified carboxy and heterocyclic group, and X′ is halogen.

Examples of the derivative at carboxy of the starting compound (XXXIX) are the same as those illustrated in the explanation of the derivative of the carboxy for $R^z$ of the compound (I).

Suitable examples of aryl in the aryl which may be substituted by at least one substituent of nitro, esterified carboxy and heterocyclic group for $R_{43}$ which correspond to those for R″ are the same as those illustrated in the explanation for Process 13 (to be referred to the explanation of the compound (XXII)).

Further, examples of the ester in the esterified carboxy may include the same as those illustrated in the explanation of the ester in the derivative of the carboxy for $R^z$ of the compound (I).

The reaction is conducted under substantially the same conditions (solvent, reaction temperature, etc.) as those explained in the explanation of the reaction for the Process 13.

(23) Process 23: (XXXXI)→(XXXXII)

In this reaction, the object compound (XXXXII) can be prepared by reacting the compound (XXXXI) with an alkylating agent.

Suitable alkylating agents may include, for example, alkanol (e.g., methanol, ethanol, propanol, isopropyl alcohol, butanol, etc.), diazoalkane (e.g., diazomethane, diazoethane, etc.), dialkyl sulfate (e.g., dimethyl sulfate, diethyl sulfate, dipropyl sulfate, etc.), alkyl tosylate (e.g., methyl tosylate, ethyl tosylate, etc.) and the like.

The present reaction is usually conducted in a solvent such as methanol, ethanol, acetone, ether, dimethylformamide and any other solvent which does not give bad influence to the reaction.

In the present reaction, in case that diazoalkane, dialkyl sulfate or alkyl tosylate is used as an alkylating agent, hydroxy group of the compound (XXXXI) may be occasionally alkylated together with the objective carboxy group, but in case that alkanol is used as an alkylating agent, only the carboxy group of the compound (XXXXI) is usually selectively alkylated.

When dialkyl sulfate, alkyl tosylate is employed as an alkylating agent in the present reaction, the reaction may be preferably conducted in the presence of a base such as an inorganic base (e.g., sodium hydroxide, potassium hydroxide, sodium carbonate, potassium carbonate, sodium bicarbonate, potassium bicarbonate, etc.) and an organic base (e.g., trimethylamine, triethylamine, pyridine, picoline, etc.), and when alkanol is employed as an alkylating agent in the present reaction, the reaction is preferably conducted in the presence of a conventional condensing agent such as 1-[4-chlorobenzenesulfonyloxy)-6-chloro-1H-benzotriazole, etc.

There is no particular limitation to the present reaction temperature, and it may be suitably selected in accordance with kinds of the compound (XXXXI) and, an alkylating agent to be used. For example, when diazoalkane is employed in the present reaction, the reaction may proceed under cooling or at ambient temperature.

(24) Process 24: (XXXXIII)→(XXXXIV)

In this process, the object compound (XXXXIV) can be prepared by subjecting the compound (XXXXIII) to elimination reaction of the protective group of protected amino.

The present elimination reaction is conducted in a conventional manner, that is under substantially the similar conditions as those described in the elimination reaction of the protective group of protected amino of the compound (XIII) in Process 9.

Examples of the protective group may include the same as those illustrated in the explanation with respect to the compound (IV).

In this reaction, in case that the starting compound (XXXIII) has the other protected amino, protected hydroxy and/or protected carboxy group in its molecule, such protective groups may be occasionally eliminated to be transformed into the corresponding amino, hydroxy and/or carboxy group, whose reaction is also included within the scope of the present process.

(25) Process 25: (XXXXV)→(XXXXVI)

In this process, the object compound (XXXXVI) can be prepared by reacting the compound (XXXXV) with a reagent selected from hydrazine, hydroxyalkylamine and aralkylamine or the salt thereof.

Suitable examples of hydroxyalkylamine may include hydroxyethylamine, hydroxypropylamine and the like, and suitable examples of aralkylamine may include benzylamine, phenethylamine and the like.

Suitable examples of the salts of hydrazine, hydroxyalkylamine or aralkylamine may include an organic acid salt (e.g., acetate, maleate, tartrate, benzenesulfonate, toluenesulfonate, etc.) and an inorganic acid salt (e.g., hydrochloride, sulfate, phosphate, etc.).

This reaction can be conducted under substantially the similar conditions as those described in the acylation of the compound (II) in Process 1.

(26) Process 26: (XXXXVII)→(XXXXVIII)

In this process, the object compound (XXXXVIII) can be prepared by reacting the compound (XXXXVII) with an esterified alkene carboxylic acid.

Examples of alkene moiety in the esterified alkene carboxylic acid may include an alkenyl which may be branched, such as 1-propenyl, 1-butenyl, 1-pentenyl, isopropenyl, methylpropenyl, methylbutenyl, methylpentenyl, ethylpropenyl, ethylbutenyl, etc., and examples of ester moiety therein may include the same ones as illustrated for the ester in the derivative of the carboxy for $R^z$ of the compound (I).

This reaction is usually conducted in a solvent which does not give bad influence to the reaction such as water, methanol, ethanol, acetone, chloroform, dimethylformamide and the like, and can be preferably conducted in the presence of a base such as an inorganic base (e.g., sodium hydroxide, potassium hydroxide, sodium carbonate, potassium carbonate, sodium bicarbonate, potassium bicarbonate, etc.) and an organic base (e.g., trimethylamine, triethylamine, pyridine, picoline, etc.).

There is no particular limitation to this reaction temperature, and the reaction may proceed under cooling or warming.

(27) Process 27: (XXXXVII)→(XXXXIX)

The object compound (XXXXIX) can be prepared by reacting the compound (XXXXVII) or its salt with an esterified aliphatic β-ketocarboxylic acid.

Examples of the esterified β-ketocarboxylic acid may include esterified alkanoylacetic acid such as ethylacetoacetate, ethylpropinoylacetate, t-butylbutyrylacetate, etc.

Suitable salt of the compound (XXXXVII) may include an organic acid salt (e.g., acetate, maleate, tartrate, benzenesulfonate, toluenesulfonate, etc.) and an inorganic acid salt (e.g., hydrochloride, sulfate, phosphate, etc.).

This reaction can be conducted with or without solvent. Suitable solvents may include methanol, ethanol, propanol, ether, acetone, benzene, toluene and any other solvent which does not give bad influence to the reaction. This reaction can be preferably conducted in the presence of a base such as an inorganic base (e.g., sodium hydroxide, potassium hydroxide, sodium carbonate, potassium carbonate, sodium bicarbonate, potassium bicarbonate, etc.) and an organic base (e.g., trimethylamine, triethylamine, pyridine, picoline, etc.).

There is no particular limitation to the present reaction temperature, and the present reaction are usually conducted under warming or heating.

Thus obtained object compound (XXXIX) may include an tautomeric isomer at the alkenylamino moiety of $R_{53}$, i.e. an alkylideneamino moiety.

(28) Process 28: (XXXXXII)→(XXXXVII)

In this process, the object compound (XXXXVII) can be prepared by reducing the compound (XXXXXII).

The reduction is conducted in a conventional manner by which nitro and azido group can be reduced to amino group, including the reduction methods as those described in the Process 15.

Suitable reduction applicable to the reaction may include a chemical reduction using a metal (e.g., tin, zinc, iron, etc.) and an acid (e.g., acetic acid, hydrochloric acid, etc.) or a catalytic reduction in the presence of a metallic catalyst such as palladium carbon, Raney-nickel, platinum oxide and other conventional catalysts.

The reaction is conducted in a solvent such as methanol, ethanol, propanol and the like.

There is no particular limitation to the present reaction temperature, and it may suitably selected in accordance with kinds of the compound (XXXXXII) and reduction methods.

(29)-(a) Process 29-(a): (XXXXXIII)→(XXXXXIV)

In this process, the object compound (XXXXXIV) can be prepared by reducing the compound (XXXXXIII).

The reduction is conducted in a conventional manner. Suitable method applicable to this reduction may be, for example, reduction using an alkali metal borohydride (e.g., sodium borohydride, lithium borohydride, etc.).

The present reaction is usually conducted in a solvent which does not give bad influence to the reaction such as water, methanol, ethanol, benzene, toluene and the like.

There is no particular limitation to the present reaction temperature, and it may be suitably selected in accordance with kinds of the compound (XXXXXIII) and reduction methods.

(29)-(b) Process 29-(b): (XXXXXV)→(XXXXXVI)

In this process, the object compound (XXXXXVI) can be prepared by reacting the compound (XXXXXV) or its derivative at carboxy with an aralkylamine under reductive condition.

Suitable examples of aralkylamine are benzylamine, phenethylamine and the like, whose benzene ring may be substituted by at least one suitable substituent.

Examples of the derivative at carboxy of the starting compound (XXXXXV) are the same as illustrated in the explanation of the derivative of the carboxy for "$R^Z$" of the compound (I).

The present reaction is conducted under reductive conditions, that is by reacting the starting compound (XXXXXV) with an aralkylamine in the presence of a conventional reducing agent or by reacting the starting compound (XXXXXV) with an aralkylamine and then reducing the resulting product with a conventional reducing agent.

Suitable examples of the reducing agents are, an alkali metal borohydride (e.g., sodium borohydride, potassium borohydride, etc.), and other conventional reducing agent and methods as illustrated in Process 6 can be used.

In case that the reaction is conducted by reacting the compound (XXXXXV) with an aralkylamine and then reducing the resulting product, the reaction of the compound (XXXXXV) with an aralkylamine can be preferably conducted in the presence of base such as an inorganic base (e.g., sodium hydroxide, potassium hydroxide, sodium carbonate, potassium carbonate, sodium bicarbonate, potassium bicarbonate, etc.) and an organic base (e.g., trimethylamine, triethylamine, pyridine, picoline, etc.).

The present reaction is usually carried out in a solvent which does not give bad influence to the reaction such as methanol, ethanol, benzene, toluene and the like.

There is no particular limitation to the present reaction temperature, and it may be suitably selected in accordance with kinds of the compound (XXXXXV), aralkylamine and reduction conditions or reduction methods.

(30) Process 30: (XXXXXVII)→(XXXXXVIII)

In this process, the object compound (XXXXXVIII) can be prepared by reacting the compound (XXXXXVII) or its derivative at carboxy with a trialkylamine.

Examples of the derivative at carboxy are the same as illustrated in the explanation of the derivative of the carboxy for "$R^Z$" of the compound (I).

Suitable trialkylamines may include trimethylamine, triethylamine, tripropylamine and the like.

The present reaction is usually conducted in a solvent which does not give bad influence to the reaction such as methanol, ethanol, acetone, ether, dimethylformamide and the like.

There is no particular limitation to the present reaction temperature, and the reaction is usually conducted at ambient temperature or under warming.

(31): Process 31: (XXXXX)→(XXXXXI)

In this process, the object compound (XXXXXI) can be prepared by reacting the compound (XXXXX) or its derivative at carboxy with an acylating agent.

The derivative at carboxy of the starting compound (XXXXX) are the same as illustrated in the explanation of the derivative of the carboxy for "$R^Z$" of the compound (I).

The acylation is conducted in a conventional manner, and the reaction is conducted under substantially the same condition (solvent, reaction temperature, etc.) as illustrated in the acylation for Process 1.

Examples of acylating agents may include the same ones as those illustrated in the Process 1.

(32) Process 32: (XXXXXII)→(XXXXXIII)

In this process, the object compound (XXXXXIII) can be prepared by reducing the compound (XXXXXII) or its derivative at the carboxy group.

Examples of the derivative at the carboxy group are the same as illustrated in the explanation of the derivative of the carboxy for "$R^Z$" of the compound (I).

The reduction is conducted by a conventional method such as chemical reduction and catalytic reduction as mentioned in the Process 3.

Suitable examples of the reduction may include a catalytic reduction using Raney nickel, Raney cobalt and the like.

The reduction is usually conducted in a solvent.

Suitable examples of the solvent include water, methanol, ethanol, propanol, dioxane and the mixture thereof, and any other solvent which has not adverse influence on the reaction.

The reduction is usually carried out at atmospheric or medium pressure.

There is no particular limitation to the reaction temperature, and the reaction is usually carried out at ambient temperature.

(33) Process 33: (XXXXXIV)→(XXXXXV)

In this process, the object compound (XXXXXV) can be prepared by reacting the compound (XXXXXIV) or its derivative at the carboxy group with an acylating agent.

Examples of the derivative at the carboxy group of the starting compound (XXXXXIV) are the same as those illustrated in the explanation of the derivative of the carboxy for "$R^Z$" of the compound (I).

Examples of the acylating agent include the same examples as illustrated in the Process 1.

The acylation is conducted in a conventional manner, and in substantially the same conditions (e.g., solvent, reaction temperature, etc.) as those mentioned in the Process 1.

(34) Process 34: (XXXXXVI)→(XXXXXVII)

In this process, the object compound (XXXXXVII) can be prepared by reacting the compound (XXXXXVI) or its derivative at the carboxy group with an aralkylating agent of the formula: $R_{69}$—X'''' (wherein $R_{69}$ is as defined above and X'''' is acid residue).

Examples of the derivative at the carboxy group of the starting compound (XXXXXVI) are the same as those illustrated in the explanation of the derivative of the carboxy for "$R^Z$" of the compound (I).

Suitable examples of the acid residue for X'''' are the same as those illustrated for $X_1$ of the compound (XI).

This reaction is usually conducted in a solvent, suitable examples of which are methylene chloride, chloroform, dichloroethane, N,N-dimethylformamide and the like.

This reaction is preferably conducted in the presence of a base as mentioned in the explanation of Process 1.

There is no particular limitation to the present reaction temperature, and the reaction is usually conducted under cooling or at ambient temperature.

(35) Process 35: (XXXXXVIII)→(I)

In this process, the object compound (I) can be prepared by subjecting the compound (XXXXXVIII) to desulfuration.

The desulfuration is usually conducted by reducing the starting compound (XXXXXVIII). For this reduction, a preferred examples of the reducing agent are Raney nickel, Raney cobalt and the like.

The reaction is usually conducted in a solvent such as ether, dioxane, methanol, ethanol, propanol, tetrahydrofuran, ethyl acetate and the like.

There is no particular limitation to this reaction, and the reaction is usually carried out at ambient or somewhat elevated temperature.

(36) Process 36: (XXXXXIX)→(XXXXXX)

In this process, the object compound (XXXXXX) can be prepared by subjecting the compound (XXXXXIX) or its reactive derivative at carboxy group to intramolecular cyclization.

Suitable examples of the reactive derivative at the carboxy group of the starting compound (XXXXXIX) may include acid anhydride, an activated amide, an activated ester and acid azid as mentioned in the explanation of Process 1, and concrete examples of such reactive derivatives may include the same as those illustrated in the explanation of Process 1.

The starting compound (XXXXXIX) includes a salt of imino group (—NH—) thereof, and suitable examples of the salt may include salts with inorganic acid such as hydrochloric acid, hydrobromic acid, sulfuric acid, phosphoric acid and the like, and organic acid such as formic acid, acetic acid, trifluoroacetic acid, benzenesulfonic acid and the like.

The reaction is usually conducted in a solvent such as methylene chloride, chloroform, diethylether, ethyl acetate, N,N-dimethylformamide and the like.

The intramolecular cyclization is usually conducted by reacting the starting compound (XXXXXIX) in the presence of a base and/or a condensing agent. Examples of the base are the same as those illustrated in the explanation of Process 1, and examples of the condensing agent are acetic anhydride, and Grignard's reagent such as methylmagnesium chloride, ethylmagnesium bromide and the like.

There is no particular limitation to this reaction, and this reaction is usually conducted under cooling or at ambient temperature.

(37) Process 37: (XXXXXXI)→(XXXXXXII)

In this process, the object compound (XXXXXXII) can be prepared by subjecting the compound (XXXXXXI) to elimination reaction of a protective group at the carboxy group.

A method for this reaction to be used may include solvolysis and reduction as mentioned in the explanation of Process 3, and the other reaction conditions for this reaction are the same as those illustrated for Process 3.

(38) Process 38: (XXXXXXIV)→(XXXXXXV)

In this process, the object compound (XXXXXXV) can be prepared by reacting the compound (XXXXXXIV) with hydrazoic acid or its derivative.

Suitable examples of a derivative of hydrazoic acid may include, sodium azide, potassium azide, calcium azide, diphenylphosphoryl azide and the like.

This reaction is usually conducted in a solvent such as tetrahydrofuran, methylene chloride, ether and the like.

There is no particular limitation to this reaction and the reaction is usually conducted under cooling or at ambient temperature.

(39) Process 39: (XXXXXXV)→(XXXXXXVI)→(XXXXXXVII)

In this process, as the first step, the compound (XXXXXXV) is heated in a solvent such as benzene, toluene and the like, to provide the compound (XXXXXXVI), and as the second step said resultant compound (XXXXXXVI) is reacted with an alcohol of the formula: $R_{74}$—OH in a solvent such as tetrahydrofuran, methylene chloride, ether and the like under cooling or somewhat elevated temperature to provide the compound (XXXXXXVII). In the above reactions, the compound (XXXXXXVI) produced in the first step can be used with or without isolation thereof as a starting compound for the second step and is subjected to the reaction of the second step to provide the compound (XXXXXXVII). The object compound (XXXXXXVII) can also be prepared more preferably from the compound (XXXXXXIV) throughout the foregoing Process 38 and successively followed by this process in one bath system.

(40) Process 40: (XXXXXXIV)→(XXXXXXVIII)

In this process, the object compound (XXXXXXVIII) can be prepared by reacting the compound (XXXXXXIV) with an oxidizing agent of the formula: $P_b(OCOR_{75})_4$.

This reaction is usually conducted in a solvent such as benzene, acetic acid, ethyl acetate methylene chloride, chloroform, ether and the like.

The reaction is also preferably conducted in the presence of a radical initiator such as cupric acetate, or under ultraviolet irradiation.

The reaction is preferably conducted under heating.

(41) Process 41: (V)→(XXXXXXIX)

In this process, the object compound (XXXXXXIX) can be prepared by reacting the compound (V) or its derivative at the carboxy group with a compound of the formula: $R_{76}$—$NH_2$.

Suitable examples of the derivative at the carboxy group of the starting compound (V) are the same as those illustrated in the explanation of the derivative of the carboxy for "$R^Z$" of the compound (I).

This reaction is conducted in substantially the same manner as mentioned in Process 16.

(42) Process 42: (XV)→(XXXXXXX)

In this process, the object compound (XXXXXXX) can be prepared by reacting the compound (XV) or its derivative at the carboxy group with a compound of the formula: $R_{77}$—X''''' (wherein $R_{77}$ is as defined above and X''''' is acid residue).

Suitable examples of the derivative at the carboxy group of the starting compound (XV) are the same as those illustrated in the explanation of the derivative of the carboxy "$R^Z$" of the compound (I).

Suitable examples of the acid residue for X''''' are the same as those illustrated in the explanation for $X_1$ of the compound (XI).

This reaction is carried out in substantially the same manner as described in the Process 34.

(43) Process 43: (XXXXXXXI)→(XXXXXXXII)

In this process, the object compound (XXXXXXXII) can be prepared by reating the compound (XXXXXXXI) or its derivative at carboxy group with an acylating agent.

Suitable examples of the derivative at the carboxy group of the starting compound (XXXXXXXI) are the same as those illustrated in the explanation of the derivative of the carboxy for "$R_Z$" of the compound (I).

Suitable examples of the acylating agent are the same as those illustrated in the Process 1.

This acylation is carried out in substantially the same manner as described in the explanation of Process 1.

(44) Process 44: (XXXXXXXIII)→(XXXXXXXIV)

This reaction is carried out in substantially the same manner as described in Process 9.

(45) Process 45: (XXXXXXXV)→(XXXXXXXVI)

This reaction is carried out in substantially the same manner as described in Process 41.

(46) Process 46: (XXXXXXXVII)→(XXXXXXXVIII)

This reaction is carried out in substantially the same manner as described in Process 43.

(47) Process 47: (XXXXXXXIX)→(XXXXXXXX)

This reaction is carried out in substantially the same manner as described in Process 9.

(48) Process 48: (XXXXXXXXI)→(XXXXXXXXII)

This reaction is carried out in substantially the same manner as described in Process 1.

(49) Process 49: (XXXXXXXXIII)→(XXXXXXXXIV)

This reaction is carried out in substantially the same manner as described in Process 9.

According to kinds of the reactions to be used in the afore-mentioned Processes, each of the alternative carboxy or corresponding derivatives at carboxy of every starting or objective compounds may occationally be transformed into each other in the course of the respective reactions or the post treatment therefor.

In the same manner, protective group(s) of the protected carboxy, protected amino and/or protected hydroxy, may be converted into the corresponding carboxy, amino and/or hydroxy group(s), respectively. Such cases of the reactions as mentioned above also include within the scope of the Processes as concerned in this invention.

The object compounds (I) of the present invention have antimicrobial activities against various pathogenic micro-organisms and may be useful for treatment of diseases infected by such micro-organisms in human being and animals.

With regard to the representative object compounds of the present invention, their antimicrobial activities against pathogenic micro-organisms are illustrated in M.I.C. (Minimum Inhibitory Concentration) value determined in a conventional manner as followed. In the following, M.I.C. value is shown as microgram per ml.

An object compound of Example 631, *Bacillus subtilis* (15); an object compound of Example 665, *Proteus vulgaris* (16), *Escherichia coli* (2.0), *Pseudomonas aeruginosa* (16);.

The following examples are given for the purpose of illustrating the present invention.

EXAMPLE 1

3-Amino-1-(α-carboxy-4-hydroxybenzyl)-2-azetidinone (hereinafter referred to 3-aminolactacillanic acid) (0.94 g.) was suspended in water (10 ml.), whereafter to the suspension was added sodium bicarbonate (0.80 g.). To the solution was added acetone (10 ml.) and then the solution was cooled to $-7°$ C., whereafter acetone (5 ml.) containing 2-phenylacetyl chloride (0.80 g.) was added to the solution. The reaction mixture was stirred at the same temperature for 2 hrs, and then the acetone was distilled off under reduced pressure. The remaining aqueous layer was washed with ether, and then adjusted to pH 2 with 10% hydrochloric acid, whereafter twice extractions were carried out with ethyl acetate (15 ml.). The extracts obtained were combined, and washed with water and a sodium chloride-saturated-aqueous solution, respectively, whereafter it was dried over anhydrous magnesium sulfate. The solvent was distilled off from the extract and the residue obtained was treated with a small amount of a mixture of ethyl acetate and ether to give 3-(2-phenylacetamido)lactacillanic acid (0.53 g.). Mp 134° to 141° C.

The following compounds were obtained in substantially the similar manner as described above.

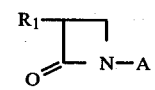
(I)

| Example | $R_1$ (note 1) | A | mp (°C.) (dec.) |
|---|---|---|---|
| 17 | ⟨phenyl⟩—CH$_2$CONH— | —CH$_2$COOH | 144–145 |
| 55 | ⟨phenyl⟩—CH$_2$CONH— | —H | 178–181 |

EXAMPLE 57

N-Phenylglycyl chloride hydrochloride (492 mg.) was suspended in methylene chloride (10 ml.), and the suspension was cooled to $-15°$ C. To the suspension were added all at once a solution prepared by dissolving 3-aminolactacillanic acid (472 mg.) and, N,O-bis(trimethylsilyl)acetamide (2.03 g.) in methylene chloride (17 ml.). The mixture was stirred for 1 hour, keeping the reaction temperature of the mixture at 0° to $-10°$ C., and then stirred for 1.5 hrs. after removing the cooling bath. The methylene chloride was distilled off from the reaction mixture, and the residue obtained was dissolved in ethyl acetate. The solution was washed with water and a sodium chloride-saturated-aqueous solution respectively, and dried. The solvent was distilled off from the solution, and to the residue was added a small amount of acetone to give crystals of 3-(N-phenylglycinamido)lactacillanic acid (116 mg.). Mp 194° to 194.5° C. The filtrate was allowed to stand under cooling to give crystals of the same object compound (60 mg.). Mp 193° to 194.5° C. Total yield was 176 mg.

The following compounds were obtained in substantially the similar manner as described above.

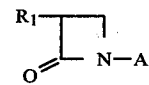
(I)

| Example | $R_1$ (note 1) | A | mp (°C.) (dec.) (note 2) |
|---|---|---|---|
| 66 | ⟨phenyl⟩—CH$_2$CONH— | —CH$_2$COOC$_2$H$_5$ | 104–105 |

| Example | R₁ (note 1) | A | mp (°C.) (dec.) (note 2) |
|---|---|---|---|
| 69 | " | —CH₂CN | 175–179 |

EXAMPLE 120

A solution containing 2-phenyl-N-(2,2,2-trichloroethoxycarbonyl)glycine (1.42 g.) and thionyl chloride (15 ml.) was heated for 1 hour under reflux. The excess of the thionyl chloride was distilled off from the solution under reduced pressure, and the residue obtained was dissolved in acetone. To the solution was added dropwise a solution containing 3-aminolactacillanic acid (1.0 g.), sodium bicarbonate (0.9 g.), water (40 ml.) and acetone (40 ml.) under cooling at 0° to 5° C. The acetone was distilled off from the reaction mixture under reduced pressure, and the remaining solution was washed with ethyl acetate. The solution was adjusted to pH 1 to 2 with 10% hydrochloric acid, and then extracted with ethyl acetate. The ethyl acetate layer was separated out and dried over anhydrous magnesium sulfate. The solvent was distilled off from the ethyl acetate solution, and the residue (2.1 g.) obtained was dissolved in ether. The ether solution was concentrated to give a residue. The residue was washed with diisopropyl ether to give crystals of 3-[2-phenyl-N-(2,2,2-trichloroethoxycarbonylglycinamido]lactacillanic acid (1.69 g.). Mp 130° to 132° C. (dec.).

The following compounds were obtained in substantially the similar manner as described above.

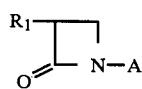
 (I)

| Example | R₁ | A | mp (°C.) (dec.) |
|---|---|---|---|
| 129 | ⟨phenyl⟩—OCH₂CONH— | —C(CH₃)=C(CH₃)—COOCH₃ | 155.5–156.5 |

EXAMPLE 192

1-(1-Methoxycarbonyl-2-methyl-1-propenyl)-3-phenoxyacetamido-2-azetidinone (1.0 g.) was dissolved in methylene chloride (40 ml.). To the solution was added N,N-dimethylaniline (0.55 g.), and the solution was cooled to −35° to −30° C. Phosphorus pentachloride (0.94 g.) was added to the solution all at once under stirring, and then the reaction mixture was stirred for 1.5 hrs. at the same temperature. Methanol (0.9 g.) was added to the reaction mixture, and then the solution was stirred for an hour at the same temperature. Elevating the reaction temperature to 0° to 5° C., water (0.6 ml.) was added to the solution, and the solution was stirred for an hour. The reaction mixture was extracted with water three times (total volume: 10 ml.), and these aqueous extracts were combined and adjusted to about pH 7 with sodium bicarbonate. The aqueous solution was washed with ethyl acetate (10 ml.) and ethyl acetate (5 ml.) respectively.

The aqueous layer was salted out with sodium chloride and then extracted with chloroform (8 ml.) seven times. These chloroform extracts were combined and dried over anhydrous magnesium sulfate, and the solvent was distilled off from the solution to give crystals of 3-amino-1-(1-methoxycarbonyl-2-methyl-1-propenyl)-2-azetidinone (0.34 g.). A part of this product was treated with p-toluenesulfonic acid in a conventional manner to give p-toluenesulfonic acid salt of a object compound. Mp 169° to 171° C. (dec.).

EXAMPLE 206

3-(2-Phenylacetamido)-2-azetidinone (816 mg.) and benzyl 2-bromo-2-phenylacetate (1.22 g.) were dissolved in N,N-dimethylformamide (20 ml.), and to the solution was added sodium hydride (50% oily) (210 mg.) in nitrogen atmosphere under ice-cooling while stirring, and then the reaction mixture was stirred for an hour at the same temperature. Ethyl acetate (150 ml.) was added to the reaction mixture, and the solution was washed with water, a sodium bicarbonate-saturated-aqueous solution and water respectively, and then dried over anhydrous magnesium sulfate. The solution was evaporated to dryness under reduced pressure to give the yellow oily material (1.7 g.). The material was subjected to column chromatography using silica-gel (developer: chloroform) to give two isomers of 1-(α-benzyloxycarbonylbenzyl)-3-(2-phenyl)acetamido-2-azetidinone. Yield of the isomer A is 26 mg. and it of the isomer B is 65 mg.

Physical constant of isomer A: Oil; Mass spectrum, m/e=428 (M+).

I.R. absorption spectrum, νcm⁻¹(CHCl₃): 1760, 1740 (shoulder), 1678.

N.M.R. absorption spectrum, δ$_{ppm}$(CDCl₃): 3.46 (2H, m), 3.55 (2H, s), 4.96 (1H, m), 5.15 (2H, s), 5.61 (1H, s), 6.37 (1H, d, J=8 Hz), 6.90–7.60 (15H, m).

Physical constant of isomer B: Mp: 96° to 98° C.; Mass Spectrum, m/e=428 (M+).

I.R. absorption spectrum, νcm⁻¹ (Nujol): 1750, 1732, 1680.

N.M.R. absorption spectrum: δ$_{ppm}$(CDCl₃): 3.03 (1H, d,d, J=3 Hz, 5 Hz), 3.53 (2H, s), 3.85 (1H,d,d, J=5 Hz, 5 Hz), 4.88 (1H, m), 5.17 (2H,s), 5.62 (1H,s), 6.05 (1H,d, J=8 Hz), 7.00–7.60 (15H, m).

The following compounds were obtained in substantially the similar manner as described above.

 (I″)

| Example | R₁ | A' | mp (°C.) (dec.) (Note 2) |
|---|---|---|---|
| 212 | ⟨phenyl⟩—CH₂CONH— | —CH₂COOC₂H₅ | 104–105 |
| 213 | " | —CH₂COOCH₂—⟨phenyl⟩ | 114–115 |

EXAMPLE 219

3-(2-Phenylacetamido)-2-azetidinone (408 mg.) and 2-chloroacetonitrile (152 mg.) was dissolved in N,N-dimethylformamide (15 ml.), and to the solution was added sodium hydride (50% oily) (105 mg.) under stirring at ambient temperature, whereafter the reaction mixture was stirred for an hour at room temperature, and ethyl acetate (100 ml.) was added to the reaction mixture. The ethyl acetate layer was washed with water and dried over anhydrous magnesium sulfate, and then the solvent was distilled off from the solution under reduced pressure. The oily residue (0.25 g.) obtained was subjected to column chromatography using silica gel. 1-Cyanomethyl-3-(2-phenylacetamido)-2-azetidinone (56.3 mg.) was obtained from fractions eluted with chloroform. Mp 108° to 109° C. (dec.).

EXAMPLE 221

An isomer B of 1-(α-benzyloxycarbonylbenzyl)-3-(2-phenylacetamido)-2-azetidinone (63 mg.) obtained in Example 206 was dissolved in isopropyl alcohol (12 ml.), and to the solution was added 10% palladium.carbon (10 mg.). The mixture was reacted in hydrogen atmosphere at ordinary temperature and ordinary atm. until the absorption of hydrogen gas was completed. The catalyst was filtered off, and the solvent was distilled off from the filtrate, and then ether was added to the residue obtained to give crystals of 1-(α-carboxybenzyl)-3-(2-phenyl-acetamido)-2-azetidinone (27 mg.), which was recrystallized from a mixture of methanol and ether to give the purified object compound. Mp 174° to 175° C. (dec.).

EXAMPLE 222

1-Carboxymethyl-3-(2-phenylacetamido)-2-azetidinone was obtained by treating 1-Benzyloxycarbonylmethyl-3-(2-phenylacetamido)-2-azetidinone in substantially the similar manner as described in Example 221. Mp 144° to 145° C.

EXAMPLE 412

Sodium methylate (15 mg.) and absolute methanol (20 ml.) were added to 1-methoxalyl-3-(2-phenoxyacetamido)-2-azetidinone (1.1 g.), and the mixture was heated under reflux for 30 minutes. The solvent was distilled off from the reaction mixture under reduced pressure, and the residue was dissolved in acetone, and then the insoluble material was filtered off. The filtrate was concentrated and allowed to stand cool, and then the precipitated crystals were collected by filtration. The crystals were washed with acetone and dried to give 3-(2-phenoxyacetamido)-2-azetidinone (456 mg.). Furthermore, the same compound (109 mg.) was recovered from the mother liquor. Total yield was 565 mg. Mp 153° to 155° C.

EXAMPLE 413

1-Methoxalyl-3-benzyloxycarbonylamino-2-azetidinone (240 mg.) was dissolved in methanol (10 ml.), and sodium methylate (6 mg.) was added to said solution, and then the mixture was heated under reflux for 45 minutes. The methanol was distilled off from the reaction mixture, and the residue was washed with ether to give crude 3-benzyloxycarbonylamino-2-azetidinone (126 mg.). Furthermore, this product was recrystallized from acetone to give the purified compound (50 mg.). And, the purified same compound (54 mg.) was recovered from the mother liquor. Total yield was 104 mg. Mp 164° to 165° C.

EXAMPLE 414

1-(1-Acetoxy-2-methylpropyl)-3-(2-phenylacetamido)-2-azetidinone (13.8 g.) was dissolved in a solution of methanol (100 ml.) and water (100 ml.). Potassium carbonate (6 g.) and sodium borohydride (1.65 g.) were added to said solution under ice-cooling, and the mixture was subjected to reaction at 20° C. for an hour. The precipitated crystals were collected by filtration, washed with water and dried to give 3-(2-phenylacetamido)-2-azetidinone (5.15 g.). Furthermore, the same compound (1.35 g.) was recovered from the filtrate. Total yield was 6.5 g. Mp 191° to 193° C.

EXAMPLE 415

1-[1-(2,2,2-Trichloroethoxycarbonylamino)-2-methylpropyl]-3-(2-phenylacetamido)-2-azetidinone (1.13 g.) was dissolved in a 90% acetic acid aqueous solution (20 ml.), and the solution was cooled to 5° C. Zinc powder (1.62 g.) was added dropwise to said solution in 5 minutes, and the mixture was stirred for 30 minutes. Furthermore, zinc powder (1.62 g.) was added to said mixture, and the mixture was stirred for 2 days. The reaction mixture was neutralized with a sodium bicarbonate aqueous solution, and extracted with methylene chloride. The extract was washed with water and dried over anhydrous magnesium sulfate, and then the solvent was distilled off from the solution. The residue (0.65 g.) was subjected to preparative thin layer chromatography using silica gel [developing solvent; a mixed solvent of ethyl acetate, ethyl methyl ketone, water and formic acid (volume ratio 5:3:1:1)], isolated and purified to give 3-(2-phenylacetamido)-2-azetidinone (0.3 g.). Mp 190° to 192° C.

EXAMPLE 544

Benzyl chloroformate (7.9 g.) was dissolved in methylene chloride (50 ml.). A methylene chloride (20 ml.) solution containing 3-amino-1-(1-methoxycarbonyl-2-methyl-1-propenyl)-2-azetidinone (2.42 g.) and triethylamine (3.7 g.) was added dropwise to the solution at −15° to −10° C. in the course of 1.33 hours with stirring, whereafter the mixture was stirred at the same temperature for 1.25 hours. The reaction mixture was evaporated to dryness under reduced pressure to give a residue, which was dissolved in ethyl acetate (150 ml.). The solution was washed three times with 5% hydrochloric acid and once with an aqueous sodium chloride, and then dried over magnesium sulfate. The solvent was removed by distillation and a residue (7.3 g.) was treated with n-hexane to give crude object compound, 3-benzyloxycarbonylamino-1-(1-methoxycarbonyl-2-methyl-1-propenyl)-2-azetidinone (3.27 g.). The compound (3.71 g.) thus obtained was subjected to column chromatography on silica gel (60 g.), and elution was carried out with chloroform and a mixture of chloroform and methanol (volume ratio; 10:1). The fractions containing the desired compound were collected and the solvent was distilled off from the eluate under reduced pressure to give the purified object compound (3.05 g.).

M.p. 135° to 137° C.

EXAMPLE 551

3-Amino-1-(2-methoxycarbonyl-1-phenylethyl)-2-azetidinone (1.3 g.) was added to methylene chloride (30 ml.), and then bis(trimethylsilyl)acetamide (3.05 g.) was added thereto. To the solution, there was dropwise added methylene chloride (30 ml.) solution containing 2-(2,2-dichloroacetoxyimino)-2-phenylacetic acid (1.9 g.) and phosphorus pentachloride (1.7 g.) at −40° to −35° C. in the course of 5 minutes. The mixture was stirred at the same temperature for 15 minutes and additionally stirred at 5° C. for 15 minutes. An aqueous sodium bicarbonate was added to the reaction mixture and the mixture was stirred at ambient temperature for 5 minutes. The methylene chloride layer was separated from the mixture, washed with dilute hydrochloric acid, an aqueous sodium bicarbonate and water in turn, and then dried over magnesium sulfate. The solvent was removed by distillation under reduce pressure to give a residue, which was subjected to column chromatography on silica gel (100 g.). Elution was carried out with chloroform and the fractions containing a desired compound were collected. The solvent was distilled off from the eluate under reduced pressure to give crystals of 3-(2-hydroxyimino-2-phenylacetamido)-1-(2-methoxycarbonyl-1-phenylethyl)-2-azetidinone (0.74 g.).

M.p. 161° to 163° C.

I.R. absorption spectrum: $\nu cm^{-1}$ (Nujol): 3220, 1730, 1720, 1620.

EXAMPLE 553

2-(2-Thienyl)-N-(2,2,2-trichloroethoxycarbonyl)glycine (1.66 g.) and thionyl chloride (150 ml.) were dissolved in a dried acetone (10 ml.), and the solution was refluxed under heating for 2 hours. The unreacted thionyl chloride was removed under reduced pressure to give a residue, which was dissolved in a dried acetone (10 ml.) to give an acetone solution. On the other hand, 3-amino-1-(1-carboxy-2-methylpropyl)-2-azetidinone (0.75 g.) was suspended in a mixture of water (15 ml.) and acetone (15 ml.), and sodium bicarbonate (0.76 g.) was added thereto. To this solution, there was dropwise added the above acetone solution at 3° to 5° C. in the course of half an hour, whereafter the mixture was stirred at the same temperature for 2 hours. The acetone was removed from the reaction mixture under reduced pressure and the remaining aqueous solution was washed with ethyl acetate. The aqueous solution was adjusted to pH 2 with dilute hydrochloric acid and then extracted with ethyl acetate. The extract was washed with water and then dried over magnesium sulfate. The solvent was removed by distillation from the solution under reduced pressure and the residue obtained was powdered with diethyl ether to give 3-[2-(2-thienyl)-N-(2,2,2-trichloroethoxycarbonyl)glycinamido]-1-(1-carboxy-2-methylpropyl)-2-azetidinone (1.70 g.).

I.R. absorption spectrum: $\nu cm^{-1}$ (KBr): 3300 to 3200, 1735, 1715, 1700, 1660.

EXAMPLE 559

3-Phthalimido-1-(2-methoxycarbonyl-1-phenylethyl)-2-azetidinone (1.90 g.) and N,N-dimethyl-1,3-propanediamine (1.14 g.) were added to a mixture of methanol (20 ml.) and chloroform (5 ml.), whereafter the mixture was stirred at ambient temperature for 17 hours. The reaction mixture was evaporated to dryness under reduced pressure to give a residue, which was dissolved in ethyl acetate (20 ml.). The solution was extracted with three portions of an aqueous solution consisting of 1N hydrochloric acid (5.3 ml.) and water (11.3 ml.), and then the combined extract was washed with ethyl acetate. The aqueous solution was adjusted to pH 8 with sodium bicarbonate under ice-cooling and then extracted with three 10 ml. portions of chloroform. The extracts were washed with water and then dried over magnesium sulfate. The solvent was removed by distillation from the solution under reduced pressure to give oily 3-amino-1-(2-methoxycarbonyl-1-phenylethyl)-2-azetidinone (1.030 g.).

I.R. absorption spectrum: $\nu cm^{-1}$ (liquid film): 3400, 1755, 1740, 1715.

EXAMPLE 570

3-[2-(2-Thienyl)-N-(2,2,2-trichloroethoxycarbonyl)-glycinamido]-1-(1-carboxy-2-methylpropyl)-2-azetidinone (1.0 g.) was dissolved in N,N-dimethylformamide (5 ml.), and acetic acid (3 ml.) was added thereto. To the solution, there was added zinc powder (1.2 g.) at 15° C. in the course of about half an hour, whereafter the mixture was stirred at 15° to 20° C. for 3 hours. The unreacted zinc powder was filtered off and washed with a small amount of N,N-dimethylformamide, and then this washings and the filtrate were combined. Diethyl ether (about 80 ml.) was added to the combined solution and the precipitating materials were collected by filtration, washed with diethyl ether and then dried to give 3-[2-(2-thienyl)glycinamido]-1-(1-carboxy-2-methylpropyl)-2-azetidinone (690 mg.).

I.R. absorption spectrum: $\nu cm^{-1}$ (Nujol): 1740, 1660, 1610 to 1600.

EXAMPLE 574

3-[2-(2-Thienyl)glycinamido]-1-(1-carboxy-2-methylpropyl)-2-azetidinone (690 mg.) was suspended in a mixture of acetone (10 ml.) and water (10 ml.), and to the suspension, there was added sodium bicarbonate (220 mg.). A dried acetone (7 ml.) solution containing 2-(2-nitro-4-chlorophenoxy)acetyl chloride (550 mg.) was added dropwise to the solution obtained above at 0° to 5° C. in the course of 45 minutes, whereafter the mixture was stirred at the same temperature for 2 hours. The acetone was removed from the reaction mixture under reduced pressure on a water bath and the remaining aqueous solution was washed with ethyl acetate. This aqueous solution was adjusted to pH 2 with dilute hydrochloric acid and then extracted with ethyl acetate. The extract was washed with water and then dried over magnesium sulfate. The solvent was removed by distillation from the solution under reduced pressure to give a residue, which was dissolved in acetone. An acetone (2 ml.) solution containing sodium 2-ethylhexanoate (100 mg.) was added to the acetone solution, and additionally diethyl ether was added thereto until the precipitating materials were not produced. The materials were collected by filtration and then dried to give sodium salt of 3-[2-(2-thienyl)-2-{2-(2-nitro-4-chlorophenoxy)acetamido}acetamido]-1-(1-carboxy-2-methylpropyl)-2-azetidinone (700 mg.).

I.R. absorption spectrum: $\nu cm^{-1}$ (Nujol): 3400, 3300, 1740, 1670, 1610.

EXAMPLE 585

4-(3-tert-Butoxycarbonylamino-3-methoxycarbonylpropoxy)phenylglyoxylic acid (1.15 g), trimethylamine (0.31 g) and N,N-dimethylbenzylamine (two drops) were dissolved in methylene chloride (10 ml), whereafter a methylene chloride (5 ml) solution containing ethylchloroformate (0.33 g) was added dropwise to the solution at −60° C. in the course of a few minutes with stirring. The reaction temperature was elevated gradually to −40° C. in the course of an hour to prepare the mixed acid anhydride solution. On the other hand, 3-aminolactacillanic acid (0.71 g) was suspended in a mixture of methylene chloride (15 ml) and N,N-dimethylformamide (0.5 ml), and to the suspension, there was added bis(trimethylsilyl)acetamide (1.83 g), whereafter the mixture was stirred at ambient temperature for an hour to dissolve it. To this solution, there was all at once added the mixed acid anhydride solution prepared above at −70° C., whereafter the mixture was stirred at the same temperature for half an hour. The stirring was continued at −50° C. for an hour and then the reaction temperature was gradually elevated to −20° C. in the course of half an hour with stirring. The reaction mixture was poured into ice-water and the resulting mixture was adjusted to pH 8 with sodium bicarbonate. The aqueous layer was separated from the mixture, adjusted to pH 2 with dilute hydrochloric acid and then extracted with ethyl acetate (200 ml). The extract was washed with water and dried over magnesium sulfate. The solvent was removed by distillation from the solution under reduced pressure to give a residue, which was powdered with diisopropyl ether to give a powdery 3-[4-(3-tert-butoxycarbonylamino-3-methoxycarbonylpropoxy)phenylglyoxyloylamino]lactacillanic acid (1.54 g).

I.R. absorption spectrum: $\nu cm^{-1}$ (Nujol): 1740, 1680, 1660.

N.M.R. absorption spectrum $\delta$ ppm ($D_2O$+NaHCO$_3$): 1.26 (9H, s), 2.14 (2H, m), 3.06 (1H, q, J=5 Hz, 2 Hz), 3.4 to 4.4 (4H, m), 3.60 (3H, s), 5.04 (1H, q, J=5 Hz, 2 Hz), 5.34 (1H, s), 6.89, 7.24 (4H, AB-q, J=8 Hz), 6.82, 7.86 (4H, AB-q, J=8 Hz).

EXAMPLE 587

3-Benzyloxycarbonylamino-1-(α-carboxy-4-benzyloxycarbonyloxybenzyl)-2-azetidinone (1.55 g) was obtained by 3-aminolactacillanic acid (1.20 g) and benzyl chloroformate (2.50 g) in substantially the same manner as described in Example 585, mp 138° to 141° C. (dec.).

I.R. absorption spectrum: $\nu cm^{-1}$ (Nujol): 3300, 1760, 1740, 1720, 1703.

EXAMPLE 590

3-Benzyloxycarbonylamino-2-azetidinone (770 mg) and acetic acid (250 mg) were dissolved in ethanol (70 ml), and to the solution, there was added 10% palladium on carbon (350 mg). The mixture was subjected to catalytic reduction in a stream of hydrogen gas at ordinary temperature and ordinary atmospheric pressure. After a calculated volume of the hydrogen gas was absorbed into the mixture, the catalyst was removed by filtration. The filtrate was evaporated to dryness under reduced pressure to give a residue, which was washed with diethyl ether. The residue (380 mg) was dissolved in hot ethyl acetate (60 ml), whereafter the solution was concentrated to a volume of about 3 ml. The precipitating crystals were collected by filtration to give acetic acid salt of 3-amino-2-azetidinone (286 mg), mp 130 to 131.5 (dec.).

EXAMPLE 592

Sodium 3-[2-{4-(3-amino-3-carboxypropoxy)-phenyl}-2-hydroxyiminoacetamido]lactacillanate (1.0 g) was dissolved in water (10 ml) and to the solution, there was dropwise added acetic anhydride (2 ml) under ice-cooling in the course of an hour. In the same time, the reaction mixture was adjusted to pH 8 to 10 with 10% aqueous sodium hydroxide. The reaction mixture was adjusted to pH 2 with 10% hydrochloric acid, and the precipitating materials were collected and washed with water to give powdery 3-[2-{4-(3-acetamido-3-carboxypropoxy)phenyl}-2-acetoxyiminoacetamido]-1-(α-carboxy-4-acetoxybenzyl)-2-azetidinone (0.66 g).

I.R. absorption spectrum: $\nu cm^{-1}$ (Nujol): 3250(broad), 1735(broad), 1650.

N.M.R. absorption spectrum: (internal standard: tetramethylsilane) $\delta$ ppm [($CD_3$)$_2$CO]: 1.96 (3H, s), 2.08 (3H, s), 2.24 (3H, s), 3.20 (2H, m), 3.37 (1H, d,d, J=6 Hz, 2 Hz), 3.9 to 4.3 (3H, m), 4.70 (1H, q, J=7 Hz), 5.20 (1H, m), 5.65 (1H, s), 6.8 to 7.8 (8H, m).

EXAMPLE 594

3-[2-{4-(3-tert-Butoxycarbonylamino-3-carboxypropoxy)phenyl}-2-hydroxyiminoacetamido]-1-(α-carboxy-4-benzyloxybenzyl)-2-azetidinone (240 mg) was suspended in benzene (2 ml), and to the suspension, there was added 2,2,2-trifluoroacetic acid (0.5 ml) at 7° C. with stirring. The mixture was stirred at the same temperature for 2 hours, and diethyl ether (about 25 ml) was added to the reaction mixture, and then the precipitating crystals were collected by filtration. The crystals were suspended in ethyl acetate and then the suspension was stirred at ambient temperature for half an hour. The crystals were collected by filtration and washed with diethyl ether to give 3-[2-{4-(3-amino-3-carboxypropoxy)phenyl}-2-hydroxyiminoacetamido]-1-(α-carboxy-4-benzyloxybenzyl)-2-azetidinone (180 mg), mp 164° to 167.5° C.

I.R. absorption spectrum; $\nu cm^{-1}$ (Nujol): 3400 to 3250, 1740, 1660, 1610.

EXAMPLE 596

3-[4-(3-Amino-3-carboxypropoxy)phenylglyoxyloylamino]-1-(α-carboxy-4-benzoyloxybenzyl)-2-azetidinone (110 mg) was obtained by reacting 3-[4-(3-tert-butoxycarbonylamino-3-carboxypropoxy)phenylglyoxyloylamino]-1-(α-carboxy-4-benzoyloxybenzyl)-2-azetidinone (650 mg) with 2,2,2-trifluoro acetic acid (4 ml) in substantially the same manner as described in Example 594, mp 181.5° to 184° C. (dec.).

I.R. absorption spectrum: $\nu cm^{-1}$ (Nujol): 3500, 3300, 1740, 1720, 1700 1660, 1600.

EXAMPLE 597

3-[4-(3-Amino-3-carboxypropoxy)phenylglyoxyloylamino]-1-(α-carboxy-4-benzyloxycarbonyloxybenzyl)-2-azetidinone (100 mg) was obtained by reacting 3-[4-(3-tert-butoxycarbonylamino-3-carboxypropoxy)phenylglyoxyloylamino]-1-(α-carboxy-4-benzyloxycarbonyloxybenzyl)-2-azetidinone (650 mg) with 2,2,2-trifluoroacetic acid (4 ml) in substantially the same manner as described in Example 594, mp 133° to 139° C. (dec.).

I.R. absorption spectrum: $\nu cm^{-1}$ (Nujol): 3500, 3300 to 3200, 1760, 1720, 1680, 1660, 1600.

EXAMPLE 602

A diethyl ether solution containing diazomethane was added dropwise to a methanol solution (10 ml) containing 3-[2-{4-(3-acetamido-3-carboxypropoxy)-phenyl}-2-acetoxyiminoacetamido]-1-(α-carboxy-4-acetoxybenzyl)-2-azetidinone (0.40 g) under ice-cooling until a color of the diazomethane was appeared, whereafter the mixture was stirred at the same temperature for 2 hours. The reaction mixture was evaporated to dryness under reduced pressure to give a residue, which was subjected to column chromatography on silica gel (50 mg). Elution was carried out with a mixture of chloroform and methanol (volume ratio, 10:1) and the fractions containing a desired compound were collected. The solvent was removed by distillation from the solution under reduced pressure to give 3-[2-{4-(3-acetamido-3-methoxycarbonylpropoxy)phenyl}-2-acetoxyiminoacetamido]-1-($\alpha$-methoxycarbonyl-4-acetoxybenzyl)-2-azetidinone (150 mg), mp 120° to 123° C. (dec.).

I.R. absorption spectrum: $\nu cm^{-1}$ (Nujol): 3300, 1740(broad), 1655.

EXAMPLE 607

3-(2-Hydroxyimino-2-phenylacetamido)lactacillanic acid (383 mg) was suspended in water (10 ml), and to the suspension, there were added 1N aqueous sodium hydroxide (1 ml) and acetone (10 ml) at 0° to 5° C. to dissolve it. A dried acetone solution (10 ml) containing benzoyl chloride (335 mg) was added dropwise to the solution obtained above in the course of half an hour at 0° to 5° C. with stirring, while ajusting to pH 7.5 to 8.0 by gradually adding 1N aqueous sodium hydroxide (2.2 ml) thereto. The stirring was continued at the same temperature for additional 1.5 hours. The acetone was removed by distillation from the reaction mixture under reduced pressure to give an aqueous solution, which was washed with ethyl acetate and adjusted to pH 1 to 2 with dilute hydrochloric acid. The resultant aqueous solution was extracted with ethyl acetate, and the extract was washed with water and then dried over magnesium sulfate. The solution was evaporated to dryness under reduced pressure to give an oily residue, which was dissolved in a small amount of diethyl ether. Cyclohexane was added to the etheral solution, until the precipitates were not produced, and the precipitates were collected by filtration and treated with cyclohexane to give 1-(4-benzoyloxy-$\alpha$-carboxybenzyl)-3-(2-benzoyloxyimino-2-phenylacetamido)-2-azetidinone (430 mg), mp 119° to 123° C.

I.R. absorption spectrum: $\nu cm^{-1}$ (Nujol): 3300, 1760, 1740, 1680.

EXAMPLE 611

3-Phthalimido-1-(2-methyl-1-methoxycarbonyl-1-propenyl)-2-azetidinone (14.6 g) was obtained by reacting 3-phthalimido-1-(2-methyl-1-methoxycarbonyl-1-propenyl)-4-(2-benzothiazolyldithio)-2-azetidinone (47 g) with Raney nickel (470 ml) in substantially the same manner as described in Example 585, mp 127° to 128° C.

I.R. absorption spectrum: $\nu cm^{-1}$ (Nujol): 1767, 1758, 1730, 1715.

N.M.R. absorption spectrum: (internal standard: tetramethylsilane) $\delta$ ppm (CD$_3$OD): 2.14 (3H, s), 2.24 (3H, s), 3.8 (3H, s), 3.96 (2H, d, J=5 Hz), 5.64 (1H, t, J=6 Hz), 7.86 (4H, s).

EXAMPLE 612

3-(2-Phenoxyacetamido)-1-(2-methyl-1-methoxycarbonyl-1-propenyl)-2-azetidinone (3.09 g) was obtained by reacting 3-(2-phenoxyacetamido)-1-(2-methyl-1-methoxycarbonyl-1-propenyl)-4-(2-benzothiazolyldithio)-2-azetidinone (13 g) with Raney nickel (75 g) in substantially the same manner as described in Example 585, mp 154° to 155° C.

I.R. absorption spectrum: $\nu cm^{-1}$ (Nujol): 3320, 1745, 1710, 1685.

N.M.R. absorption spectrum: (internal standard: tetramethylsilane) $\delta$ ppm (CDCl$_3$): 2.02 (3H, s), 2.23 (3H, s), 3.57 (1H, d,d, J=3 Hz, 5 Hz), 3.85 (1H, t, J=5 Hz, 5 Hz), 4.54 (2H, s), 5.07 (1H, m), 6.86 to 7.42 (5H, m).

EXAMPLE 613

3-Phthalimido-1-(1-carboxy-2-methyl-1-propenyl)-2-azetidinone (240 mg) was obtained by reacting sodium salt of 3-phthalimido-1-(1-carboxy-2-methyl-1-propenyl)-4-(2-benzothiazolyldithio)-2-azetidinone (2.0 g) with Raney nickel (20 ml) in substantially the same manner as described in Example 585.

I.R. absorption spectrum: $\nu cm^{-1}$ (Nujol): 1780, 1770, 1760, 1720.

N.M.R. absorption spectrum: (internal standard: tetramethylsilane) $\delta$ ppm (CD$_3$OD): 2.40 (3H, s), 2.80 (3H, s), 4.00 to 4.18 (2H, m), 5.67, 5.83 (1H, d,d, J=7 Hz), 8.13 (4H, s).

EXAMPLE 614

Crude 3-(2-phenoxyacetamido)-1-(1-methoxycarbonyl-2-methyl-1-propenyl)-2-azetidinone (45 mg) was obtained by reacting 3-(2-phenoxyacetamido)-1-(1-methoxycarbonyl-2-methyl-1-propenyl)-4-[1-(1-methoxycarbonyl-2-methyl-1-propenyl)-2-oxo-3-(2-phenoxyacetamido)-4-azetidinyldithio]-2-azetidinone (50 mg) with Raney nickel (1 ml) in substantially the same manner as described in Example 585.

I.R. absorption spectrum: $\nu cm^{-1}$ (Nujol): 3320, 1745, 1710, 1685.

EXAMPLE 616

1-($\alpha$-Methoxycarbonyl-4-hydroxybenzyl)-3-(2-phenylacetamido)-2-azetidinone (40 mg) was dissolved in acetone (5 ml), and to the solution, there was added 0.1N aqueous sodium hydroxide (3 ml) under ice-cooling. The mixture was stirred at the same temperature for 10 minutes. The acetone was removed by distillation under reduced pressure to give an aqueous solution, which was washed with ethyl acetate. The aqueous solution was adjusted to pH 2 with 1N hydrochloric acid and extracted with ethyl acetate. The extract was washed with water and then dried over magnesium sulfate. The solvent was removed by distillation from the solution under reduced pressure to give a residue, which was crystallized from acetone to give 3-(2-phenylacetamido)lactacillanic acid (20 mg), mp 134° to 141° C.

EXAMPLE 617

1-(2-Carboxy-1-phenylethyl)-3-(2-hydroxyimino-2-phenylacetamido)-2-azetidinone (0.31 g) was obtained by reacting 1-(2p-methoxycarbonyl-1-phenylethyl)-3-(2-hydroxyimino-2-phenylacetamido)-2-azetidinone (0.49 g) with 1N aqueous sodium hydroxide (3 ml) in substantially the same manner as described in Example 616, mp 157° to 158° C.

I.R. absorption spectrum $\nu cm^{-1}$ (Nujol): 3180, 1720, 1710, 1635.

EXAMPLE 621

A tetrahydrofuran solution (5 ml) containing triethylamine (1.02 g) was added to a tetrahydrofuran solution (40 ml) containing 1-(1-carboxy-2-methylpropyl)-3-(2-phenylacetamido)-2-azetidinone (3.04 g) at −20° C. with stirring. To this solution, there was dropwise added a tetrahydrofuran solution (5 ml) containing ethyl chloroformate (1.14 g) at −10° C. in the course of 5 minutes, whereafter the mixture was stirred at −10° to 0° C. for 2 hours. To the resultant mixture, there was all at once added water (8 ml), in which sodium azide (1.23 g) was dissolved at the same temperature, and the stirring was continued for additional half an hour. The reaction mixture was poured into ice-water (200 ml) and the resultant mixture was extracted with three portions of 100 ml methylene chloride. The extracts were washed with three portions of 100 ml water and dried over calcium chloride. The solution was evaporated to dryness under reduced pressure to give oily 1-(1-azidocarbonyl-2-methylpropyl)-3-(2-phenylacetamido)-2-azetidinone (3.0 g).

I.R. absorption spectrum: $v cm^{-1}$ (Nujol): 3300, 2250, 1700, 1650.

EXAMPLE 622

1-(1-Azidocarbonyl-2-methylpropyl)-3-(2-phenylacetamido)-2-azetidinone (2.6 g) was dissolved in absolute toluene (50 ml) and the solution was refluxed under heating for 20 minutes. Insoluble materials were removed by filtration to give a filtrate, to which 1-methylimidazole (0.1 ml) and 2,2,2-trichloroethanol (1.45 g) were added. After the mixture was heated at 80° C. for an hour, the solvent was removed by distillation from the reaction mixture under reduced pressure to give a viscous oily residue, which was adsorbed to silica gel (8 g). This silica gel was subjected to column chromatography on additional silica gel (30 g) for isolation and purification to give 1-[1-(2,2,2-trichloroethoxycarbonylamino)-2-methylpropyl]-3-(2-phenylacetamido)-2-azetidinone (2.66 g).

I.R. absorption spectrum: $v cm^{-1}$ (Nujol): 3300, 1765, 1740(shoulder), 1650.

EXAMPLE 623

A mixture of 1-(1-carboxy-2-methylpropyl)-3-(2-phenylacetamido)-2-azetidinone (1.50 g), triethylamine (0.51 g), diphenylphosphoryl azide (1.4 g) and tert-butyl alcohol (30 ml) was heated gradually, and refluxed under heating for 5 hours. After the reaction, the tert-butyl alcohol was removed by distillation from the reaction mixture under reduced pressure to give a residue, which was subjected to column chromatography on silica gel. Elution was carried out with a mixture of benzene and ethyl acetate, and the fractions containing a desired compound were collected. The eluate was evaporated to dryness under reduced pressure to give 1-(1-tert-butoxycarbonylamino-2-methylpropyl)-3-(2-phenylacetamido)-2-azetidinone (1.1 g), mp 64° to 66° C.

EXAMPLE 624

Copper acetate (one hydrate, 199 mg) was added to an ethyl acetate solution (200 ml) containing 1-(1-carboxy-2-methylpropyl)-3-(2-phenylacetamido)-2-azetidinone (3.04 g) with stirring. To the resultant mixture, there was added lead tetraacetate (4.9 g) at ambient temperature in the course of 5 minutes, whereafter the mixture was refluxed under heating for half an hour with stirring. The insoluble materials were removed by filtration to give a filtrate, which was washed with water, an aqueous sodium chloride and an aqueous sodium bicarbonate and then washed with an aqueous sodium chloride twice in turn, whereafter dried over magnesium sulfate. The ethyl acetate was removed by distillation from the solution under reduced pressure to give oily 1-(1-acetoxy-2-methylpropyl)-3-(2-phenylacetamido)-2-azetidinone (2.7 g).

I.R. absorption spectrum: $v cm^{-1}$ (film): 1760, 1735(shoulder), 1665.

EXAMPLE 631

3-[2-(2-Thienyl)acetamido]lactacillanic acid (480 mg) was suspended in water (10 ml), and to the suspension, there was added sodium bicarbonate (520 mg) to dissolve it. Acetone (10 ml) was added to the solution, whereafter a dried acetone solution (5 ml) containing benzoyl chloride (560 mg) was added dropwise thereto under ice-cooling with stirring. The stirring was continued at the same temperature for about 4.2 hours and then at ambient temperature for additional 5 hours. The acetone was removed by distillation from the reaction mixture under reduced pressure to give an aqueous solution, which was washed with ethyl acetate. The aqueous solution was adjusted to pH 1 to 2 with dilute hydrochloric acid and extracted with ethyl acetate. The extract was washed with water and then dried over magnesium sulfate. The solution was evaporated to dryness under reduced pressure to give a residue, which was subjected to column chromatography on silica gel (20 g). Elution was carried out with ethyl acetate and the fractions containing a desired compound were collected. The solvent was removed by distillation from the solution under reduced pressure to give a residue, which was crystallized from ethyl acetate to give 1-(4-benzoyloxy-α-carboxybenzyl)-3-[2-(2-thienyl)acetamido]-2-azetidinone (240 mg), mp 129° to 131° C.

EXAMPLE 632

Sodium salt of 1-(α-carboxy-4-benzyloxycarbonyloxybenzyl)-3-[2-(2-thienyl)acetamido]-2-azetidinone (310 mg) was obtained by reacting 3-[2-(2-thienyl)acetamido]lactacillanic acid (360 mg) with benzyl chloroformate (0.221 g) in substantially the same manner as described in Example 631, mp 128° to 130° C.

EXAMPLE 633

3-[4-(3-tert-Butoxycarbonylamino-3-carboxypropoxy)phenylglyoxyloylamino]-1-(α-carboxy-4-benzyloxycarbonyloxybenzyl)-2-azetidinone (1.2 g) was obtained by reacting 3-[4-(3-tert-butoxycarbonylamino-3-carboxypropoxy)phenylglyoxyloylamino]lactacillanic acid (1.17 g) with benzyl chloroformate (0.450 g) in substantially the same manner as described in Example 631.

I.R. absorption spectrum: $v cm^{-1}$ (Nujol): 3400 to 3300, 1750, 1730 to 1710, 1690, 1670.

N.M.R. absorption spectrum: (internal standard: tetramethylsilane) δ ppm [(CD$_3$)$_2$CO]: 1.39 (3H, s), 2.20 to 2.44 (2H, m), 3.37, 3.43 (1H, d,d, J=2 Hz, 5 Hz), 3.81 (1H, t, J=5 Hz), 4.25 (2H, t, J=6 Hz), 5.12 to 5.26 (1H, m), 5.28 (2H, s), 5.64 (1H, s), 6.24 (1H, d, J=8 Hz), 7.00 to 7.60 (11H, m), 8.20 (1H, d, J=8 Hz), 8.68 (1H, d, J=8 Hz).

EXAMPLE 634

3-[4-(3-tert-Butoxycarbonylamino-3-carboxypropoxy)phenylglyoxyloylamino]-1-(α-carboxy-4-benzoyloxybenzyl)-2-azetidinone (1.10 g) was obtained by reacting 3-[4-(3-tert-butoxycarbonylamino-3-carboxypropoxy)phenylglyoxyloylamino]lactacillanic acid (960 mg) with benzoyl chloride (281 mg) in substantially the same manner as described in Example 631.

I.R. absorption spectrum: νcm$^{-1}$ (Nujol): 3400 to 3200, 1740, 1720 to 1710, 1680, 1670.

N.M.R. absorption spectrum: (internal standard: tetramethylsilane) δ ppm [(CD$_3$)$_2$CO]: 1.38 (3H, s), 2.26 to 2.44 (2H, m), 3.39, 3.45 (1H, d,d, J=2 Hz, 5 Hz), 4.00 (2H, t, J=5 Hz), 4.24 (2H, t, J=6 Hz), 4.38 (1H, m), 5.06 to 5.30 (1H, m), 5.68 (1H, s), 6.24 (1H, d, J=8 Hz), 7.00 to 8.24 (13H, m), 8.72 (1H, d, J=8 Hz).

EXAMPLE 635

3-[4-(3-tert-Butoxycarbonylamino-3-carboxypropoxy)phenylglyoxyloylamino]-1-[α-carboxy-4-{N-(2,2,2-trichloroacetyl)carbamoyloxy}benzyl]-2-azetidinone (610 mg) was obtained by reacting 3-[4-(3-tert-butoxycarbonylamino-3-carboxypropoxy)phenylglyoxyloylamino]lactacillanic acid (585 mg) with 2,2,2-trichloroacetic isocyanic anhydride (1.0 g) in substantially the same manner as described in Example 631.

I.R. absorption spectrum: νcm$^{-1}$ (Nujol): 3350 to 3250, 1780, 1740, 1720, 1660.

N.M.R. absorption spectrum: (internal standard: tetramethylsilane) δ ppm [(CD$_3$)$_2$CO]: 1.55 (3H, s), 2.36 to 2.62 (2H, m), 3.38, 3.44 (1H, d,d, J=2 Hz, 5 Hz), 3.99 (1H, t, J=5 Hz), 4.20 to 4.42 (3H, m), 5.10 to 5.30 (1H, m), 5.64 (1H, s), 6.96 to 7.60 (6H, m), 8.16 (2H, d, J=8 Hz), 8.68 (1H, d, J=8 Hz).

EXAMPLE 646

3-Aminolactacillanic acid was suspended (0.236 g.) in dried dichloromethane (15 ml.), and to the suspension there was added N,O-bis(trimethylsilyl)acetamide (1.0 g.), whereafter the mixture was stirred at ambient temperature for 5 hours. Thionyl chloride (180 mg.) was added to dimethylformamide (80 ml.) and the mixture was heated to 40°–50° C. for 30 minutes and then thionyl chloride was removed therefrom under reduced pressure to give a white crystal. Ethyl acetate (20 ml.) was added to the crystal and then 2-methoxyimino-2-[2-(2,2,2-trifluoroacetamido)-4-thiazolyl]acetic acid (265 mg.) was added to the mixture at 0°–5° C. while stirring. The stirring was continued at the same temperature for 40 minutes, thereafter the mixture was cooled at −30° C. To this solution was added the above 3-aminolactacillanic acid-solution and then the mixture was stirred at −30° C. for 2.5 hours. The mixture was warmed to 0°–5° C. and reacted at the same temperature. The reaction mixture was further warmed to ambient temperature and then allowed to stand overnight. The mixture was evaporated to dryness under reduced pressure to give a residue, which was dissolved into ethyl acetate. The solution was washed with water and then concentrated under reduced pressure to give an oil (0.450 g.). The oil was subjected to column chromatography on silica gel and elution was carried out with ethyl acetate to give 3-[2-methoxyimino-2-{2-(2,2,2-trifluoroacetamido)-4-thiazolyl}acetamido]lactacillanic acid (280 mg.)

NMR: δ ppm[(CD$_3$)$_2$CO]: 3.24, 3.32 (1H, d,d, J=2, 5 Hz), 3.84 (3H, s), 3.98 (1H, t, J=5 Hz), 5.14 to 5.32 (1H, m), 5.52 (1H, s), 6.82 (2H, d, J=8 Hz), 7.22 (2H, d, J=8 Hz), 7.96 (1H, s), 8.20 (1H, broad s), 8.44 (1H, d, J=8 Hz).

The following compounds (Examples 647 to 656) were obtained in substantially the same manner as described in Example 646.

EXAMPLE 652

Ethyl 3-phenyl-2-[3-(2-phenylacetamido)-2-oxo-1-azetidinyl]acrylate.

NMR: δ ppm (CDCl$_3$): 1.28 (3H, t, J=6 Hz), 3.53 (2H, s), 4.24 (2H, q, J=6 Hz), 3.40, 3.44 (1H, d, d, J=2, 4 Hz), 3.73 (1H, t, J=4 Hz), 4.96 to 5.12 (1H, m), 6.92 (1H, d, J=8 Hz), 7.26 to 7.52 (11H, m).

EXAMPLE 653

3-Phenyl-2-[3-(2-phenylacetamido)-2-oxo-1-azetidinyl]acrylic acid.

NMR: δ ppm (CD$_3$OD): 3.42, 3.46 (1H, d,d, J=2, 4 Hz), 3.54 (2H, s), 3.68 (1H, t), 7.20 to 7.53 (11H, m).

EXAMPLE 654

Methyl 2-[3-{4-(3-tert-butoxycarbonylamino-3-methoxycarbonylpropoxy)phenylglyoxyloylamino}-2-oxo-1-azetidinyl]-3-methyl-2-butenoate.

NMR: δ ppm (CDCl$_3$): 1.42 (9H, s), 2.04 (3H, s), 2.24 (3H, s), 2.20 to 2.37 (2H, m), 3.72 (3H, s), 3.76 (3H, s), 3.63, 3.70 (1H, q, J=2, 5 Hz), 3.88 (1H, t, J=5 Hz), 4.14 (2H, t, J=6 Hz), 4.40 to 4.60 (1H, m), 5.02 to 5.20 (1H, m), 5.28 (1H, d, J=8 Hz), 6.93 (2H, d, J=9 Hz), 7.82 (1H, d, J=8 Hz), 8.37 (2H, d, J=9 Hz).

EXAMPLE 655

Benzyl 2-[3-{2-(2-thienyl)acetamido}-2-oxo-1-azetidinyl]acetate.

NMR: δ ppm (CDCl$_3$): 3.26, 3.31 (2H, d,d, J=2 Hz, 5 Hz), 3.73 (1H, t, J=6 Hz), 3.78 (2H, s), 4.04 (2H, s), 5.16-4.07 (1H, m), 5.17 (2H, s), 7.26-6.81 (9H, m).

EXAMPLE 657

3-[3-(3-t-butoxycarbonylamino-3-carboxypropoxy)-phenylglyoxyloylamino]lactacillanic acid (1.38 g) was suspended in a mixture of benzene (15 ml.) and anisole (1 ml.) and then 2,2,2-trifluoroacetic acid (5 ml.) was added to the suspension under cooling while stirring. The stirring was continued for 1.5 hours, and then acetone (20 ml.) was added thereto, followed by stirring vigorously for 20 minutes to give a powder. The powder was washed with ether to give a crude object compound, 3-[3-(3-amino-3-carboxypropoxy)phenylglyoxyloylamino]lactacillanic acid (1.10 g.).

The crude object compound (300 mg.) was dissolved in water (5 ml.) and the solution was adjusted to pH 3.0 with sodium bicarbonate aqueous solution to give an oil. The oil was subjected to column chromatography on Amberlite XAD-4 (trade mark, made by Rohn & Haas Co.) and elution was carried out with methanol. Eluate was crystallized with acetone to give a purified object compound, 3-[3-(3-amino-3-carboxypropoxy)phenylglyoxyloylamino]lactacillanic acid (160 mg.), mp 182° to 183° C.

The following compounds (Examples 658 to 664) were obtained by reacting the corresponding 3-acylamino-2-azetidinone compounds having t-butoxy carbonylamino group with 2,2,2-trifluoroacetic acid in substantially the same manner as described in Example 657.

EXAMPLE 660

2-[3-[2-{4-(3-Amino-3-carboxypropoxy)phenyl}-2-hydroxyiminoacetamido]-2-oxo-1-azetidinyl]-3-methyl-2-butenoic acid.

NMR: δ ppm (D$_2$O+N$_a$HCO$_3$): 1.84 (3H, s), 1.96 (3H, s), 2.08 to 2.40 (2H, m), 3.68, 3.75 (1H, q, J=2,5

Hz), 3.88 (1H, t, J=5 Hz), 4.12 (2H, t, J=5 Hz), 5.09, 5.16 (1H, q, J=2,5 Hz), 6.98 (2H, d, J=8 Hz), 7.50 (2H, d, J=8 Hz).

EXAMPLE 661

2-[3-{4-(3-Amino-3-carboxypropoxy)phenylglyoxyloylamino}-2-oxo-1-azetidinyl]-2-(4-carbamoyloxyphenyl)acetic acid.

IR $v$cm$^{-1}$ (Nujol): 3500 to 3200, 1730, 1720, 1660, 1600.

EXAMPLE 665

2-[4-(2-Phenylacetoxy)phenyl]-2-[3-[2-{4-(3-carboxy-3-tritylaminopropoxy)phenyl}-2-hydroxyiminoacetamido]-2-oxo-1-azetidinyl]acetic acid (0.5 g.) was dissolved in 80% acetic acid (10 ml.) and the mixture was stirred for 45 minutes. Insoluble materials were filtered off from the reaction mixture and the filtrate was evaporated to dryness under reduced pressure. The residue obtained was triturated with ethyl acetate to give a powder (0.27 g.). This powder (0.2 g.) was dissolved in an aqueous sodium bicarbonate and the solution was adjusted to pH 3 with 10% hydrochloric acid to give crystals of 2-[3-[2-{4-(3-amino-3-carboxypropoxy)phenyl}-2-hydroxyiminoacetamido]-2-oxo-1-azetidinyl]-2-[4-(2-phenylacetoxy)phenyl]acetic acid (0.14 g.).

IR $v$cm$^{-1}$ (Nujol): 3250, 1750, 1730, 1670.

EXAMPLE 673

3-[4-(3-t-Butoxycarbonylamino-3-carboxypropoxy)-3-chlorophenylglyoxylamino]lactacillanic acid (760 mg.) was suspended in water (10 ml.), and to the suspension was added hydroxylamine hydrochloride (330 mg.). The mixture was adjusted to pH 7 with sodium bicarbonate, whereafter the resultant mixture was stirred at 55° C. for 2 hours. The aqueous layer was washed with ethyl acetate and then adjusted to pH 2 with 10% hydrochloric acid and extraction was carried out twice with ethyl acetate. The ethyl acetate layer was washed with water and dried over magnesium sulfate and then concentrated under reduced pressure to give 3-[2-{4-(3-tert-butoxycarbonylamino-3-carboxypropoxy)-3-chlorophenyl}-2-hydroxyiminoacetamido]lactacillanic acid (0.51 g.).

IR $v$cm$^{-1}$ (Nujol): 3350, 1740, 1700, 1640.

The following compounds (Examples 674 to 678) were obtained by reacting a compound having a carbonyl group with hydroxylamine hydrochloride in substantially the same manner as described in Example 673.

EXAMPLE 676

2-[3-[2-{4-(3-tert-Butoxycarbonylamino-3-carboxypropoxy)phenyl}-2-hydroxyiminoacetamido]-2-oxo-1-azetidinyl]-3-methyl-2-butenic acid.

IR $v$cm$^{-1}$ (film): 3400 to 3300, 1760, 1720 to 1700, 1670 to 1650.

EXAMPLE 680

3-[2-{4-(3-carboxy-3-tritylaminopropoxy)phenyl}-2-hydroxyiminoacetamido]lactacillanic acid (0.75 g.) was dissolved in a mixture of water (20 ml.) and acetone (20 ml.), and 1N-sodium hydroxide (2 ml.) was added thereto under cooling. The solution was stirred for a few minute at 5° C., and 2-phenylacetyl chloride (0.16 g.) and 1N-sodium hydroxide (1 ml.) were added thereto, keeping the solution pH 9-11. The acetone was distilled off from the solution under reduced pressure to give a residue. The residue was adjusted to pH 5 with 50% acetic acid under cooling to give an oil, which was extracted twice with ethyl acetate. The ethyl acetate layer was washed with water and dried over magnesium sulfate. The ethyl acetate was distilled off to give a residue which was crystallized with ether to give 2-[3-[2-{4-(3-carboxy-3-tritylaminopropoxy)phenyl}-2-hydroxyiminoacetamido]-2-oxo-1-azetidinyl]-2-[4-(2-phenylacetoxy)phenyl]acetic acid (0.44 g.).

IR $v$cm$^{-1}$ (Nujol): 3240, 1750, 1730, 1655.

EXAMPLE 687

2-[3-{4-(3-tert-Butoxycarbonylamino-3-carboxypropoxy)phenylglyoxyloylamino}-2-oxo-1-azetidinyl]-2-[4-{N-(2,2,2-trichloroacetyl)carbamoyloxy}phenyl]acetic acid (550 mg.) was suspended in water (5 ml.), and to the suspension there were added sodium bicarbonate (250 mg.) and methanol (1 ml.). The mixture was stirred at ambient temperature for 7 hours. The reaction mixture was adjusted to pH 2 with dilute hydrochloric acid and the precipitating material was collected by filtration. The material was washed with water and then dried to give 2-[3-{4-(3-tert-butoxycarbonylamino-3-carboxypropoxy)phenylglyoxyloylamino}-2-oxo-1-azetidinyl]-2-(4-carbamoyloxyphenyl)acetic acid.

IR $v$cm$^{-1}$ (Nujol): 3300 to 3150, 1750, 1730, 1660.

EXAMPLE 688

2-(3-phthalimido-2-oxo-1-azetidinyl)acetate was dissolved in a mixture (5 ml) of chloroform and ethanol (1:1), and 1N ethanol solution of hydrozene monohydrate (1 ml.) was added thereto at ambient temperature while stirring. The stirring was continued for 72 hours. The reaction mixture was filtered and the filtrate was concentrated under reduced pressure. The residue thus obtained was dissolved in ethanol, and then ethanol solution (1 ml.) of p-toluenesulfonyl chloride mono hydrate (190 mg.) was added thereto. The mixture was concentrated under reduced pressure, and to the residue thus obtained there were added ethanol (1 ml.) and ethyl acetate (2 ml.) to give crystalline benzyl 2-(3-amino-2-oxo-1-azetidinyl)acetate p-toluenesulfonic acid salt, mp 147.5°-149° C.

What we claim is:

1. A compound of the formula or its acetic acid addition salt:

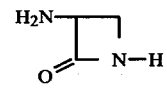

* * * * *